US011981896B2

(12) United States Patent
Pilpel et al.

(10) Patent No.: US 11,981,896 B2
(45) Date of Patent: May 14, 2024

(54) P21 mRNA TARGET AREAS FOR SILENCING

(71) Applicant: 1E Therapeutics Ltd., Rehovot (IL)

(72) Inventors: Noam Pilpel, Rehovot (IL); Yossi Ovadya, Rehovot (IL); Dina Raichlin, Rehovot (IL); Etti Katz-Kadosh, Rehovot (IL); Alaa Knany, Rehovot (IL); Ella Gillis, Rehovot (IL); Noam Borovsky, Rehovot (IL); Anastasia Shapiro, Rehovot (IL); Ido Bachelet, Rehovot (IL)

(73) Assignee: 1E Therapeutics Ltd., Rehovot (IL)

( * ) Notice: Subject to any disclaimer, the term of this patent is extended or adjusted under 35 U.S.C. 154(b) by 0 days.

(21) Appl. No.: 18/342,806

(22) Filed: Jun. 28, 2023

(65) Prior Publication Data

US 2023/0357771 A1  Nov. 9, 2023

Related U.S. Application Data

(63) Continuation of application No. PCT/IL2021/051545, filed on Dec. 28, 2021.

(60) Provisional application No. 63/130,936, filed on Dec. 28, 2020.

(51) Int. Cl.
*C12N 15/113* (2010.01)
*A61P 35/00* (2006.01)

(52) U.S. Cl.
CPC ............ *C12N 15/113* (2013.01); *A61P 35/00* (2018.01); *C12N 2310/14* (2013.01); *C12N 2310/32* (2013.01)

(58) Field of Classification Search
CPC ............ C12N 15/113; C12N 2310/14; C12N 2310/127; C12N 2310/315; C12N 2310/321; C12N 2310/322; C12N 2310/3525; A61K 48/00; A61P 35/00
USPC .................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 3,687,808 A | 8/1972 | Merigan et al. |
| 3,850,578 A | 1/1974 | Mcconnell |
| 3,791,932 A | 2/1974 | Schuurs et al. |
| 3,839,153 A | 10/1974 | Schuurs et al. |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,659,774 A | 4/1987 | Webb et al. |
| 4,666,828 A | 5/1987 | Gusella |
| 4,683,202 A | 7/1987 | Mullis |
| 4,801,531 A | 1/1989 | Frossard |
| 4,816,571 A | 3/1989 | Andrus et al. |
| 4,879,219 A | 11/1989 | Wands et al. |
| 4,959,463 A | 9/1990 | Foehler et al. |
| 5,011,771 A | 4/1991 | Bellet et al. |
| 5,141,813 A | 8/1992 | Nelson |
| 5,192,659 A | 3/1993 | Simons |
| 5,264,566 A | 11/1993 | Froehler et al. |
| 5,272,057 A | 12/1993 | Smulson et al. |
| 5,281,521 A | 1/1994 | Trojanowski et al. |
| 5,428,148 A | 6/1995 | Reddy et al. |
| 5,464,764 A | 11/1995 | Capecchi et al. |
| 5,487,992 A | 1/1996 | Capecchi et al. |
| 5,554,744 A | 9/1996 | Bhongle et al. |
| 5,574,146 A | 11/1996 | Reddy et al. |
| 5,602,244 A | 2/1997 | Caruthers et al. |
| 5,998,203 A | 12/1999 | Matulic-adamic et al. |
| 6,326,174 B1 | 12/2001 | Joyce et al. |
| 6,361,941 B1 | 3/2002 | Todd et al. |
| 8,686,128 B2 | 4/2014 | Khachigian |
| 10,023,597 B2 | 7/2018 | Minomi et al. |
| 2003/0125270 A1 | 7/2003 | Blatt et al. |
| 2004/0266734 A1 | 12/2004 | Dannenberg et al. |
| 2005/0064407 A1 | 3/2005 | Sun et al. |
| 2005/0222065 A1 | 10/2005 | Khachigian |
| 2010/0249216 A1 | 9/2010 | Sel et al. |
| 2011/0065772 A1 | 3/2011 | Khachigian |

(Continued)

FOREIGN PATENT DOCUMENTS

| | | |
|---|---|---|
| WO | WO 1993/015187 A1 | 8/1993 |
| WO | WO 1999/050452 A1 | 10/1999 |
| WO | WO 2002/081494 A1 | 10/2002 |

(Continued)

OTHER PUBLICATIONS

Roberts et al (Nature Rev., Drug Discovery, vol. 19, pp. 673-694 (2020)) (Year: 2020).*

(Continued)

*Primary Examiner* — Jane J Zara

(74) *Attorney, Agent, or Firm* — Mark S. Cohen; PEARL COHEN ZEDEK LATZER BARATZ LLP

(57) ABSTRACT

Compositions of matter comprising RNA silencing molecules capable of mediating cleavage of p21 mRNA are disclosed. Methods of eradicating senescent cells or cancer cells, as well as methods of treating senescence-associated diseases or disorders, cancer, and fibrotic diseases and disorders are also disclosed.

15 Claims, 8 Drawing Sheets

Specification includes a Sequence Listing.

(56) References Cited

U.S. PATENT DOCUMENTS

| | | |
|---|---|---|
| 2013/0237696 A1 | 9/2013 | Khachigian |
| 2020/0121620 A1 | 4/2020 | Gil et al. |

FOREIGN PATENT DOCUMENTS

| | | |
|---|---|---|
| WO | WO 2002/099090 A1 | 12/2002 |
| WO | WO 2005/0003331 A1 | 1/2005 |
| WO | WO 2009/003211 A1 | 1/2009 |
| WO | WO 2010/077366 A2 | 7/2010 |
| WO | WO 2012/087983 A1 | 6/2012 |
| WO | WO 2013/126963 A1 | 9/2013 |
| WO | WO 2014/107763 | 7/2014 |
| WO | WO 2014/174511 A1 | 10/2014 |
| WO | WO 2016/106402 A1 | 6/2016 |
| WO | WO 2016/135732 A1 | 9/2016 |
| WO | WO 2016/185481 A1 | 11/2016 |

OTHER PUBLICATIONS

Kobelt et al (Cancer Gene Therapy in Gene Therapy of Cancer: Methods and Protocols, Methods in Molecular Biology, vol. 2521, pp. 1-15 (Springer Nature 2022)) (Year: 2022).*

Osborn et al (Nucleic Acid Therapeutics, vol. 28, No. 3, pp. 128-136 (2018)) (Year: 2018).*

Damase et al (Frontiers in Bioengineering and Biotechnology, vol. 9, Article 628137, pp. 1-24 (2021)) (Year: 2021).*

Bost et al (ACS Nano, vol. 15, pp. 13993-14021 (2021)) (Year: 2021).*

Abbas et al. "p21 in cancer: intricate networks and multiple activities" Nature reviews. Cancer. Jun. 2009;9(6):400.

Ashcroft et al. "Simple method of estimating severity of pulmonary fibrosis on a numerical scale" Journal of Clinical Pathology. Apr. 1988;41(4):467.

Asseline et al. "Improved nuclear delivery of antisense 2'-Ome RNA by conjugation with the histidine-rich peptide H5WYG" The journal of gene medicine. 2014;16(7-8):157-65.

Asthana et al. (2014) "Mannosylated Chitosan Nanoparticles for Delivery of Antisense Oligonucleotides for Macrophage Targeting" BioMed Research International. 2014:Article #526391.

Bartel DP. "MicroRNAs: genomics, biogenesis, mechanism, and function" Cell. Jan. 23, 2004;116(2):281-97.

Breaker et al. "A DNA enzyme that cleaves RNA" Chemistry & biology. Dec. 1994;1(4):223-9.

Brennecke et al. "Principles of MicroRNA—Target Recognition" PLoS Biology. Mar. 2005;3(3):e85.

Campisi et al. "Cellular senescence: when bad things happen to good cells" Nature reviews. Molecular cell biology. Sep. 2007;8(9):729-40.

Coppé et al. "The Senescence-Associated Secretory Phenotype: The Dark Side of Tumor Suppression" Annual review of pathology. 2010;5:99-118.

Danenberg et al. "Systemic depletion of macrophages by liposomal bisphosphonates reduces neointimal formation following balloon-injury in the rat carotid artery" Journal of cardiovascular pharmacology. Nov. 1, 2003;42(5):671-9.

Danenberg et al. "Macrophage depletion by clodronate-containing liposomes reduces neointimal formation after balloon injury in rats and rabbits" Circulation. Jul. 30, 2002;106(5):599-605.

Danenberg et al. "Liposomal alendronate inhibits systemic innate immunity and reduces in-stent neointimal hyperplasia in rabbits" Circulation. Dec. 2, 2003;108(22):2798-804.

Deleavey et al. "Designing chemically modified oligonucleotides for targeted gene silencing" Chemistry & biology. Aug. 24, 2012;19(8):937-54.

De Mesmaeker et al. "Amides as a New Type of Backbone Modification in Oligonucleotides" Angew. Chem. Int. Ed. Engl. 1994, 33, No. 2., 1994, pp. 226-229.

Falzarano et al. "Nanoparticle Delivery of Antisense Oligonucleotides and Their Application in the Exon Skipping Strategy for Duchenne Muscular Dystrophy" Nucleic Acid Therapeutics. Feb. 2, 2014;24(1):87.

Feldman et al. "A new and efficient DNA enzyme for the sequence-specific cleavage of RNA" Journal of molecular biology. Oct. 19, 2001;313(2):283-94.

Fleury et al. "Exploiting interconnected synthetic lethal interactions between PARP inhibition and cancer cell reversible senescence" Nature Communications. 2019;10; 2556.

Gait MJ. "Peptide-mediated cellular delivery of antisense oligonucleotides and their analogues" Cellular and molecular life sciences. May 2003;60(5):844-53.

GeneBank Accession No. NM_001291549.3, version 3, Nov. 30, 2021.

GeneBank Accession No. NM_000389.5, version 5, Dec. 1, 2021.

GeneBank Accession No. NM_001220777.2, version 2, Nov. 30, 2021.

GeneBank Accession No. NM_001220778.2, version 2, Nov. 29, 2021.

GeneBank Accession No. NM_001374509.1, version 1, Nov. 29, 2021.

GeneBank Accession No. NM_001374510.1, version 1, Nov. 29, 2021.

GeneBank Accession No. NM_001374511.1, version 1, Nov. 29, 2021.

GeneBank Accession No. NM_001374512 1, version 1, Nov. 29, 2021.

GeneBank Accession No. NM_001374513.1, version 1, Nov. 29, 2021.

GeneBank Accession No. NM_078467.3, version 3, Nov. 29, 2021.

Gilboa E. "Transfer and expression of cloned genes using retroviral vectors" BioTechniques. 1986;4:504-12.

Grijalvo et al. "Oligonucleotide delivery: a patent review (2010-2013)" Expert opinion on therapeutic patents. Jul. 2014;24(7):801-19.

Hollenstein M. "DNA Catalysis: The Chemical Repertoire of DNAzymes" Molecules (Basel, Switzerland). Nov. 20, 2015;20(11):20777-804.

Huang et al. "Thioredoxin interacting protein (TXNIP) regulates tubular autophagy and mitophagy in diabetic nephropathy through the mTOR signaling pathway" Scientific reports. Jul. 6, 2016;6:29196.

Inoue et al. "Sorafenib attenuates p21 in kidney cancer cells and augments cell death in combination with DNA-damaging chemotherapy" Cancer Biology & Therapy. Nov. 11, 2011;12(9):827.

International Search Report for PCT Application No. PCT/IL2021/051546 dated Sep. 2, 2022.

International Search Report for PCT Application No. PCT/IL2021/051545 dated Jul. 25, 2022.

Jääskeläinen et al. "In vitro delivery of antisense oligonucleotides" Cellular & molecular biology letters. 2002;7(2):236-7.

Jiang et al. "Local and transient inhibition of p21 expression ameliorates age-related delayed wound healing" Wound repair and regeneration: official publication of the Wound Healing Society [and] the European Tissue Repair Society. Jan. 2020;28(1):49-60.

Kabanov et al. "A new class of antivirals: antisense oligonucleotides combined with a hydrophobic substituent effectively inhibit influenza virus reproduction and synthesis of virus-specific proteins in MDCK cells" FEBS letters. Jan. 1, 1990;259(2):327-30.

Khachigian LM. "Deoxyribozymes as Catalytic Nanotherapeutic Agents" Cancer research. Mar. 1, 2019;79(5):879-88.

Kirkland et al. "Clinical Strategies and Animal Models for Developing Senolytic Agents" Experimental gerontology. Aug. 2015;68:19.

Krek et al. "Combinatorial microRNA target predictions" Nature genetics. May 1, 2005;37(5):495-500.

Letsinger et al. "Cholesteryl-conjugated oligonucleotides: synthesis, properties, and activity as inhibitors of replication of human immunodeficiency virus in cell culture" Proceedings of the National Academy of Sciences of the United States of America. Sep. 1989;86(17):6553-6.

Lewis et al. "Conserved seed pairing, often flanked by adenosines, indicates that thousands of human genes are microRNA targets" Cell. Jan. 14, 2005;120(1):15-20.

(56) References Cited

OTHER PUBLICATIONS

Löfdahl et al. "Pulmonary fibrosis in vivo displays increased p21 expression reduced by 5-HT2B receptor antagonists in vitro—a potential pathway affecting proliferation" Scientific Reports. 2018;8:1927.
Martino et al. "Efficient siRNA Delivery by the Cationic Liposome DOTAP in Human Hematopoietic Stem Cells Differentiating into Dendritic Cells" Journal of Biomedicine and Biotechnology. 2009;2009:Article ID 410260.
Mokany et al. "MNAzymes, a Versatile New Class of Nucleic Acid Enzymes That Can Function as Biosensors and Molecular Switches" Journal of the American Chemical Society. Jan. 1, 2010;132(3):1051.
Oberhauser et al. "Effective incorporation of 2'-O-methyl-oligoribonucleotides into liposomes and enhanced cell association through modification with thiocholesterol" Nucleic acids research. Feb. 11, 1992;20(3):533-8.
Ovadya et al. "Strategies targeting cellular senescence" The Journal of Clinical Investigation. Apr. 4, 2018;128(4):1247.
Paddison et al. "Stable suppression of gene expression by RNAi in mammalian cells" Proceedings of the National Academy of Sciences of the United States of America. Feb. 5, 2002;99(3):1443-8.
Pandya et al. "Nanocomposites and IT's application—review" International Journal of Pharmaceutical Sciences and Research. 2013;4(1):19-28.
Park et al. "High throughput screening of a small molecule one-bead-one-compound combinatorial library to identify attenuators of p21 as chemotherapy sensitizers" Cancer biology & therapy. Dec. 2008;7(12):2015-22.
Prakash et al. "Targeted delivery of antisense oligonucleotides to hepatocytes using triantennary N-acetyl galactosamine improves potency 10-fold in mice" Nucleic acids research Jul. 2014;42(13):8796-807.
Roberts et al. "Advances in oligonucleotide drug delivery" Nature Reviews. Drug Discovery. 2020;19(10):673.
Sagiv et al. "p53 in Bronchial Club Cells Facilitates Chronic Lung Inflammation by Promoting Senescence" Cell reports. Mar. 27, 2018;22(13):3468-79.
Saison-Behmoaras et al. "Short modified antisense oligonucleotides directed against Ha-ras point mutation induce selective cleavage of the mRNA and inhibit T24 cells proliferation" The EMBO Journal. May 1991;10(5):1111.
Santoro in"A general purpose RNA-cleaving DNA enzyme" Proceedings of the National Academy of Sciences of the United States of America. Apr. 4, 1997;94(9):4262.
Sax et al. "The cyclin-dependent kinase inhibitor butyrolactone is a potent inhibitor of p21 (WAF1/CIP1 expression)" Cell cycle (Georgetown, Tex.). Jan. 2002;1(1):90-6.
Seluanov et al. "Establishing Primary Adult Fibroblast Cultures from Rodents" Journal of Visualized Experiments: JoVE Journal of Visualized Experiments 2010;(44)44. http://www.jove.com/details.php?id=2033.
Shea et al. "Synthesis, hybridization properties and antiviral activity of lipid-oligodeoxynucleotide conjugates" Nucleic acids research, Jul. 11, 1990;18(13):3777-83.
Shinagawa et al. "Generation of Ski-knockdown mice by expressing a long double-strand RNA from an RNA polymerase II promoter" Genes & Development. Jun. 6, 2003;17(11):1340.
Tran et al. "Control of specific gene expression in mammalian cells by co-expression of long complementary RNAs" FEBS letters. Aug. 27, 2004;573(1-3):127-34.
Tuschl T. "RNA Interference and small interfering RNAs" Chembiochem: a European journal of chemical biology. Apr. 2, 2001;2(4):239-45.
Wang et al. "DNA enzyme ED5 depletes egr-1 and inhibits neointimal hyperplasia in rats" Cardiology 2013;125(3):192-200.
Wettersten et al. "A novel p21 attenuator which is structurally related to sorafenib" Cancer Biology & Therapy. Mar. 3, 2013;14(3):278.
Xiang et al. "Downregulated expression of plasminogen activator inhibitor-1 augments myocardial neovascularization and reduces cardiomyocyte apoptosis after acute myocardial infarction" Journal of the American College of Cardiology. Aug. 2, 2005;46(3):536-41.
Xu et al. "Senolytics Improve Physical Function and Increase Lifespan in Old Age" Nature medicine. Aug. 2018;24(8):1246.
Yao et al. "Suppression of Transcription Factor Early Growth Response 1 Reduces Herpes Simplex Virus 1-Induced Corneal Disease in Mice" Journal of Virology. Aug. 2012;86(16):8559.
Yosef et al. "p21 maintains senescent cell viability under persistent DNA damage response by restraining JNK and caspase signaling" The EMBO Journal. Aug. 8, 2017;36(15):2280.
Zhou et al. "Theranostic dnazymes" Theranostics. 2017;7(4):1010.

* cited by examiner

FIG. 3

>NM_001291549.3 Homo sapiens cyclin dependent kinase inhibitor 1A (CDKN1A), transcript variant 3, mRNA ATGTGAGCTCTGGCATAGAAGAGGCTGGTGGCTATTTTGTCCTTGGGCTGCCTGTTTTCAGGTGAGGAAGGGATGTAGGAGAAGACAGGAGACCTCTA
AAGACCCCAGAAATAAAGGATGACAAGCAGAGAGGCCAAAGTCCTGTGTTCCAACTATAGTCATTTCTTGCTGCATGATCTGAG
TTAGGTCACCAGACTTCTCTGAGCTGTGGCAGTTTCCCCAGCAGTGTATACGGCCAGCAACTCACTCGTCAAATCCT
CCCCTTCCTGGCCAACAAAGCTGCTGCAACCACAGGGATTTCTGTTCAGGTCGCGAGTCAGAACCGGCTGGGATGTCCGTCAGAACCATGCGG
CAGCAAGGCCTGCCGCCGTCTTGCCGCCCCAGTGGGACACAGCAGCTGAGCCGCGACTGTGAGCCGCCTGAATGGCGGGTGCATCCAGGAGGCCCGTG
AGCGGATGGAACTTCGACTTTGTCACCGAGACAACCACTCCTGAGGAGGCAGGGTGACTTCGCCTGGGGCTGTGCCGCCTTGGCCCAAGCTCTACCTTCCC
ACGGGCCCCCCGGGGATGAGTGTTGGGATCTCTCTGCTCGCTCCATGGGTTGGGGCCTCTGAGGGCTGGTTGAGCGGATGGTCGGAAAGACCATGTGGA
CCTGTCACTGTCTTGTACCCTGTGCCCTCGCTGCCGCAACGCCGGCTGATTCTCCACCACCCAAAACGCCGGGCCTCTCCAGGTCGCTGAAAACGGCGGCAGA
CCAGCATGACAGATTTCTACCACTCCCAAAACGCCGGGCTGATCTCTCAGTTGTGTCTTAATTAAACAAAACTAGGCGGTTGAATGAGAGAGTTCCTGGACT
GGGCCCTCAAAGGCCCGCCTGCCCGCCCCCCTGTAAAGCTCCCCGCTGCCTCATCCTCGGAGGGTGTGGCCGGGTTATGAACCTTCATGCCCAGCTACTTCCTCC
ATTTTATGAATATAAAGCTATTTAAAGCCTCCCTGGGTGGGTACCCTGTGCCCTCCCATCCTCCCGTGTTCATCCCTGCTCGTCGTGCACCGAGTCCCCTCAC
TCCCCACTGTCGAATTCTTTTTCATTGAGAAGTAAACAGAGATGAACTCCCGAGTGGGCCATCATCCAATCTAAAAACTTTGAGCAAAACTTTGGAGTCCCCTCAC
CAGACCTGAATTCTTTTCATTGAGAAGTAAACAGAGATGAACTCCCGAGTGGGCCATCATCCAGTGATACCCTCGTCTTGATACCCCCTCTGTCT
CTCCTCTAAGGTTGGGCAGGGGAAGGGTGGGTCCCCGTACCTGACCTGGCGCCCTCATGGCCCGTGTCTCAGTGTTGAGC
TGTGAAGGCAGGGAAGGGTCCTCCTGGCCTTTTGAACCTTCAGCTACCCTCGAGGTTCCTTCTGCAATTCCCCTGGGCTGCAATTCAATGACTCAATGACTGACTGGAAGGGACA
CTTGTGTCCTTCCCTTCCTTTGCCCTTCAGCTACCCTCAGGTTCCTGCTACCTCCTCAAGCAGCCCAGCGCGCCCCTTCCTCAGTGTGGAGCGGACAG
CACAAGAAGAGGGCACCCCAGTTCTACCTTACCTGCTGCCAGGGTACCAGGATCTTTCTAGGAGGAGGACACATTTTAAGATGGTGCAGTAGAGGCTATGA
GCCCCCTTGAGGTGGGGTTATCTCGTGTTAGGGTATATGAATTGCACTTTGACTTCATTGGGGCTGGAACAAGAGTCAGAATGCAGTAGAGGCTATGGA
TTCCTCATCCATGACCATGCCACGTGGGGTCTGACCCCCAAAACACCTTCCAGGCCTGGACTGTTTTCTCTGCCCTGTAACATACTGGACTGTTTAGTACTTG
CAGGGGCATGGGAAGCGTCCCAAGGGGTAAACCCTGACTGTTAAACCTGACCCTCCTCCAACCCTTCACAGCAGCAGTGTGTCTCTCTGCCCTGTAACATACTGGACTGTTTAGTACTTG
CCACCTAGACTGTAAACTCTGAGGGCAGGACCACCACTGATAAGCTCTGAATATACAGGTCTGCGTCCTTTCACCCTGACTGATCACTTAGCCTGAGCTGGCAGTTGACAGCAGTGC
TCAATAAATGATTCTTAGTGACTTTA

SEQ ID NO: 1

P21 mRNA TARGET AREAS FOR SILENCING

CROSS-REFERENCE TO RELATED APPLICATIONS

This application is a Continuation application of International PCT Application No. PCT/IL2021/051545, International Filing Date 28 Dec. 2021, claiming the benefit of U.S. Patent Application No. 63/130,936, filed 28 Dec. 2020, which are hereby incorporated by reference in their entirety.

SEQUENCE LISTING STATEMENT

The instant application contains a Sequence Listing which has been submitted electronically in XML file format and is hereby incorporated by reference in its entirety. Said XML copy, created on Jul. 10, 2023, is named P-616659-US_SL.xml and is 209,224 bytes in size.

FIELD AND BACKGROUND OF THE INVENTION

The present invention, in some embodiments thereof, relates to p21 mRNA target areas for efficient silencing and, more particularly, but not exclusively, to RNA silencing molecules for use in targeting these areas.

Cellular Senescence

Cellular senescence is a stable form of cell-cycle arrest that limits the proliferative potential of cells. The senescence program is triggered in many cell types in response to various stresses and is associated with age-related diseases. Senescent cells typically accumulate in tissues and contribute to the establishment of a chronic inflammation that arises due to continuous secretion of pro-infSEQ lammatory cytokines via the senescence associated secretory phenotype (SASP).

Several approaches that focus on either clearance of senescent cells or prevention of their pro-inflammatory impact are in development for therapeutics. Efforts are largely invested in the discovery of pharmacological agents that can induce cell death in senescent cells. These compounds are generally termed "senolytic drugs" or "senolytics." Senolytics have emerged as promising agents for treatment of pulmonary fibrosis, atherosclerosis, osteoarthritis, type I and 2 diabetes mellitus, and neurocognitive decline [Ovadya, and Krizhanovsky, *The Journal of clinical investigation* (2018) 128(4): 1247-1254], for rejuvenation of aged hematopoietic and muscle stem cells and for extending the lifespan of naturally aged mice [Xu et al., *Nature medicine* (2018) 24(8): 1246-1256].

Cellular senescence has also been implicated as a major cause of morbidity in cancer. It is well established that chemotherapy may not completely eliminate cancer cells and that recurrent cancer is typically more aggressive and refractory to therapy. Therapy-induced-senescence (TIS) is thought to be an underlying cause of this phenomenon wherein certain populations of the cancer cells being exposed to sub-lethal chemotherapeutic DNA damaging agents, utilize senescence as a cellular escape mechanism thereby exacerbating the patient's condition e.g. via SASP. Senolytics may therefore improve the prognosis and treatment of cancer patients. An alternative treatment regime which has been suggested, referred to as the "one-two punch" [Fleury et al., *Nature communications* (2019) 10(1): 1-15] contemplates first applying chemotherapy at doses which do not eliminate the cancer cells (but rather induce them to senesce) followed by the second "punch" which consists of a senolytic agent to eliminate these cancer senescent cells.

p21

As illustrated in FIG. 1, cellular senescence is controlled by the p53 and p16-retinoblastoma protein (pRB) tumor suppressor pathways. Senescence-inducing signals, including those that trigger a DNA-damage response (DDR), as well as many other stresses, usually engage one of these two pathways. Some signals, such as oncogenic RAS, engage both pathways. p53 is negatively regulated by the E3 ubiquitin-protein ligase HDM2 (MDM2 in mice), which facilitates its degradation, and HDM2 is negatively regulated by the alternate-reading-frame protein (ARF). Active p53 establishes the senescence growth arrest in part by inducing the expression of p21, a cyclin-dependent kinase (CDK) inhibitor that, among other activities, suppresses the phosphorylation and, hence, the inactivation of pRB. Senescence signals that engage the p16-pRB pathway generally do so by inducing the expression of p16, another CDK inhibitor that prevents pRB phosphorylation and inactivation. pRB halts cell proliferation by suppressing the activity of E2F, a transcription factor that stimulates the expression of genes that are required for cell-cycle progression. E2F can also curtail proliferation by inducing ARF expression, which engages the p53 pathway. Accordingly, there is reciprocal regulation between the p53 and p16-pRB pathways and the senescence program is driven by a complex interplay of signaling pathways. To promote and support cell cycle arrest, p16INK4A (CDKN2A), accompanied by the p53 target p21 (CDKN1A, WAF1, CIP1), inhibits cyclin-dependent kinases (CDKs), thereby preventing phosphorylation of the retinoblastoma protein (pRb) and thus in turn suppressing the expression of proliferation-associated genes.

In normal cells, p21 maintains its genuine signature function as a cell cycle inhibitor and anti-proliferative effector. Upregulation of p21 enables senescent cells to maintain their viability after damage induction, and allows their retention within tissues [Yosef, R. et al., *The EMBO journal* (2017) 36(15), 2280-2295]. Increased expression of p21 was evident in various age-related conditions associated with cellular senescence [Coppe et al., *Annual Review of Pathological Mechanical Disease* (2010) 5: 99-118] and in a bleomycin induced pulmonary fibrosis model [Löfdahl et al., *Scientific reports* (2018) 8(1); 1-9]. Increased levels of p21 were evident in a Chronic Obstructive Pulmonary Disease (COPD) mouse model and senolytic treatment by ABT-737 reduced p21 levels [Sagiv et al., *Cell reports* (2018) 22(13): 3468-3479]. p21 levels were also augmented in non-healing chronic wounds and local and transient inhibition of p21 by siRNA ameliorated the delayed wound healing in aged mice [Jiang et al., *Wound Repair and Regeneration* (2020) 28(1): 49-60].

Small molecule inhibitors of p21 have been developed for cancer therapy including butyrolactone I (BL) [Sax et al., *Cell cycle* (Georgetown, Tex.) (2002) 1(1): 90-96], LLW10 [Park et al., *Cancer biology & therapy* (2008) 7(12): 2015-2022], sorafenib [Inoue et al., *Cancer biology & therapy* (2011) 12(9): 827-836], and UC2288 [Wettersten et al., *Cancer biology & therapy* (2013) 14(3): 278-285].

DNAzymes

DNAzymes are synthetic, catalytically-active DNA molecules that are able to specifically cleave target mRNA without requiring the involvement of cellular mechanisms such as the RNA-Induced Silencing Complex (RISC). DNAzymes have not been reported in nature and are typically generated by in-vitro selection. Moreover. DNAzymes are diverse structurally and mechanistically, and exhibit diverse secondary structures, metal ion dependencies, and catalysis kinetics.

Of the various classes of DNAzymes, the most studied in the therapeutic context has been the 10-23 class. The 10-23 DNAzymes cleave target RNA molecules, and are functionally classified as antisense, or silencing. DNAzymes. The 10-23 DNAzymes are driven by a central 15-nucleotide long catalytic core, flanked by two regions that are complementary to the target RNA (FIG. 2A). Hybridization of the DNAzyme to its target via the flanking regions enables the catalytic core to attack its target phosphodiester bond (FIG. 2B). Importantly, the mechanism of action of 10-23 DNAzymes makes them suitable for cleaving RNA targets inside living cells as illustrated in FIG. 2C.

The therapeutic potential of DNAzymes has been demonstrated in diverse settings including pre-clinically in a variety of cancer models [Khachigian *Cancer Res* (2019) 79(5): 879-888], in cardiovascular in-vivo models [Wang et al., *Cardiology* (2013) 125(3): 192-200], in viral infections [Yao et al. *J Virol* (2012) 86(16): 8559-8567], in kidney treatment [Huang et al., *Sci Rep* (2016) 6: 29196] and following myocardial infarction [Xiang et al., *J Am Coll Cardiol* (2005) 46(3): 536-541].

Additional background art includes:

PCT publication no. WO/2014/174511 provides methods of treating an inflammatory or fibrotic disease in a subject by administering a therapeutically effective amount of an agent (e.g. RNA silencing agent, such as a Ribozyme, DNAzyme or antisense) which down-regulates an activity and/or an amount of Bcl-xL and/or Bcl-w and/or p21, wherein the inflammatory disease is not cancer.

PCT publication no. WO/2016/185481 provides methods of targeting a pharmaceutical agent (e.g. cytotoxic agent such a DNAzyme) to a senescent cell for therapeutics or diagnostics.

PCT publication no. WO/2016/135732 provides methods of promoting hair growth by the down-regulation of genes encoding Bcl-2-family proteins and/or p21 (e.g. by utilizing RNA silencing agents, such as a Ribozyme. DNAzyme or antisense).

U.S. Pat. No. 10,023,597 provides compounds, compositions and methods for modulating the expression of human p21 using RNA interference. The RNA interference molecules (e.g. siRNA, miRNA, shRNA) can be used in methods for preventing or treating diseases such as malignant tumor.

SUMMARY OF THE INVENTION

According to an aspect of some embodiments of the present invention there is provided a composition of matter comprising an RNA silencing molecule capable of mediating cleavage of p21 mRNA in a region spanning nucleic acids 1947-2022 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 1455-1473 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 1089-1346 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 1524-1890 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 168-240 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 944-1065 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 475-683 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 797-933 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 290-372 corresponding to SEQ ID NO: 1.

According to an aspect of some embodiments of the present invention there is provided a composition of matter comprising an RNA silencing molecule capable of mediating cleavage of p21 mRNA in a region spanning nucleic acids 2233-2250 corresponding to SEQ ID NO: 1.

According to an aspect of some embodiments of the present invention there is provided a composition of matter comprising an RNA silencing molecule capable of mediating cleavage of a p21 mRNA sequence as set forth in any one of SEQ ID NOs: 3-12.

According to an aspect of some embodiments of the present invention there is provided a pharmaceutical composition comprising the composition of matter of some embodiments of the invention, and a pharmaceutically acceptable carrier.

According to an aspect of some embodiments of the present invention there is provided a method of eradicating a senescent cell or a cancer cell, the method comprising contacting the senescent cell or the cancer cell with the composition of matter of some embodiments of the invention, thereby eradicating the senescent cell or the cancer cell.

According to an aspect of some embodiments of the present invention there is provided a method of treating a senescence-associated disease or disorder in a subject in need thereof, the method comprising administering to the subject a therapeutically effective amount of the composition of matter of some embodiments of the invention, or the pharmaceutical composition of some embodiments of the invention, thereby treating the senescence-associated disease or disorder.

According to an aspect of some embodiments of the present invention there is provided a therapeutically effective amount of the composition of matter of some embodiments of the invention for use in treating a senescence-associated disease or disorder in a subject in need thereof.

According to an aspect of some embodiments of the present invention there is provided a method of treating a cancer in a subject in need thereof, the method comprising administering to the subject a therapeutically effective amount of the composition of matter of some embodiments of the invention, or the pharmaceutical composition of some embodiments of the invention, thereby treating the cancer.

According to an aspect of some embodiments of the present invention there is provided a therapeutically effective amount of the composition of matter of some embodiments of the invention for use in treating cancer in a subject in need thereof.

According to an aspect of some embodiments of the present invention there is provided a method of treating a fibrotic disease or disorder in a subject in need thereof, the method comprising administering to the subject a therapeutically effective amount of the composition of matter of some embodiments of the invention, or the pharmaceutical composition of some embodiments of the invention, thereby treating the fibrotic disease or disorder.

According to an aspect of some embodiments of the present invention there is provided a therapeutically effective amount of the composition of matter of some embodiments of the invention for use in treating a fibrotic disease or disorder in a subject in need thereof.

According to some embodiments of the invention, the RNA silencing molecule is selected from the group consisting of a DNAzyme, a ribozyme, an antisense oligonucleotide (ASO), a small interference RNA (siRNA), a microRNA (miRNA) and a short hairpin RNA (shRNA).

According to some embodiments of the invention, the RNA silencing molecule is a DNAzyme capable of mediating cleavage of p21 mRNA.

According to some embodiments of the invention, the RNA silencing molecule is a DNAzyme molecule comprising a nucleic acid sequence at least 80% identical to the nucleic acid sequence set forth in any one of SEQ ID NOs: 18, 19, 20, 21 or 22.

According to some embodiments of the invention, the RNA silencing molecule is a DNAzyme molecule comprising a nucleic acid sequence set forth in any one of SEQ ID NOs: 18, 19, 20, 21 or 22.

According to some embodiments of the invention, the DNAzyme molecule comprises no more than 70 nucleotides.

According to some embodiments of the invention, the DNAzyme molecule comprises a catalytic core of no more than 50 nucleotides.

According to some embodiments of the invention, the DNAzyme molecule is a 10-23 type DNAzyme molecule.

According to some embodiments of the invention, the DNAzyme molecule is a 8-17 type DNAzyme molecule.

According to some embodiments of the invention, the nucleic acid sequence of the RNA silencing molecule comprises at least one modification.

According to some embodiments of the invention, the modification comprises an insertion, a deletion, a substitution or a point mutation of at least one nucleic acid.

According to some embodiments of the invention, the modification comprises a modification that increases the stability or prevents degradation of the RNA silencing molecule.

According to some embodiments of the invention, the modification comprises an edge-blocker oligonucleotide.

According to some embodiments of the invention, the modification comprises an inverted deoxythymidine (dT) positioned in at least one terminal end of the RNA silencing molecule.

According to some embodiments of the invention, the modification comprises at least one protective group positioned in at least one terminal end of the RNA silencing molecule.

According to some embodiments of the invention, the modification comprises a base modification, a sugar modification and/or an internucleotide linkage modification.

According to some embodiments of the invention, the sugar modification is selected from the group consisting of a 2'-O-methyl (2'-O-Me), a 2'-O-methoxyethyl (2'-O-MOE), a 2'-fluoro (2'-F), a locked nucleic acid (LNA), and a 2'-Fluoroarabinooligonucleotides (FANA).

According to some embodiments of the invention, the internucleotide linkage modification is selected from the group consisting of a phosphorothioate, a chiral phosphorothioate, a phosphorodithioate, a phosphotriester, an aminoalkyl phosphotriester, a methyl phosphonate, an alkyl phosphonate, a chiral phosphonate, a phosphinate, a phosphoramidate, an aminoalkylphosphoramidate, a thionophosphoramidate, a thionoalkylphosphonate, a thionoalkylphosphotriester, a boranophosphate, a phosphodiester, a phosphonoacetate (PACE) and a peptide nucleic acid (PNA).

According to some embodiments of the invention, the RNA silencing molecule is attached to a heterologous moiety.

According to some embodiments of the invention, the heterologous moiety comprises a cell-targeting moiety or a cell-penetrating moiety.

According to some embodiments of the invention, the cell-targeting moiety is an affinity moiety.

According to some embodiments of the invention, the cell-targeting moiety binds to a senescent cell specific cell surface polypeptide.

According to some embodiments of the invention, the cell-targeting moiety binds to a cancer cell specific cell surface polypeptide.

According to some embodiments of the invention, the method is affected in vitro.

According to some embodiments of the invention, the method is affected in vivo.

According to some embodiments of the invention, the senescence-associated disease or disorder is selected from the group of an age-related disease or disorder, a neurological disease or disorder, a neurodegenerative disease or disorder, a cardiovascular disease or disorder, a pulmonary disease or disorder, an inflammatory disease or disorder, an autoimmune disease or disorder, a metabolic disease or disorder, a hepatic disease or disorder, a dermatological disease or disorder, an eye disease or disorder, a fibrotic disease or disorder, a cardiac disease or disorder, a vascular disease or disorder, a renal disease or disorder, and a cancer.

According to some embodiments of the invention, the cancer is a therapy-resistant cancer.

According to some embodiments of the invention, the composition is for systemic, intranasal, inhalation, intracerebroventricular, intrathecal, oral, local injection, intratumoral, or intravenous administration.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A: DNAzyme structure—composed of two recognition arms that bind the mRNA sequence and a catalytic core (also referred to as catalytic site) which cleaves the target mRNA. FIG. 2B: Mechanism of action—the DNAzyme binds to the target mRNA via base paring with the recognition arms and the catalytic core is then able to cleave the phosphodiester bond thereby preventing subsequent protein translation. DNAzyme molecules are able to release themselves from the target mRNA following cleavage and recycle to cleave additional mRNA molecules of the same target. FIG. 2C: Senolytic activity is achieved by degradation and silencing of key senescence survival regulator targets thereby causing senescent cell death.

FIG. 3 illustrates the mRNA sequence for human p21 (i.e. *Homo sapiens* cyclin dependent kinase inhibitor 1A (CDKN1A), transcript variant 3, mRNA, NM_001291549.3, as set forth in SEQ ID NO: 1), and the predicted hot areas (underlined).

FIG. 5A: Agarose gel electrophoresis of p21 mRNA incubated with several targeting DNAzymes. Scrambled DNAzymes controls are mutated in either the sequence recognition arms or cleavage loop (Scr A and B, respectively). DNAzyme numbers relate to their cleavage site position on the p21 mRNA. DNAzymes targeting high scoring areas are marked in bold/red and display a marked increase in cleavage compared to other areas marked in blue. FIG. 5B: DNAzyme cleavage of the p21 mRNA using DNAzyme 1991 targeting the high scoring area displayed a concentration and time dependence.

DESCRIPTION OF SPECIFIC EMBODIMENTS OF THE INVENTION

The present invention, in some embodiments thereof, relates to p21 mRNA target areas for efficient silencing and, more particularly, but not exclusively, to RNA silencing molecules for use in targeting these areas.

The principles and operation of the present invention may be better understood with reference to the drawings and accompanying descriptions.

Before explaining at least one embodiment of the invention in detail, it is to be understood that the invention is not necessarily limited in its application to the details set forth in the following to description or exemplified by the Examples. The invention is capable of other embodiments or of being practiced or carried out in various ways. Also, it is to be understood that the phraseology and terminology employed herein is for the purpose of description and should not be regarded as limiting.

Cellular senescence is a stable form of cell-cycle arrest that is associated with chronic inflammation and with various pathologies, including fibrosis, atherosclerosis, osteoarthritis, diabetes and cancer. Cellular senescence is typically controlled by the p53 and p16-retinoblastoma protein (pRB) tumor suppressor pathways. Active p53 establishes the senescence growth arrest in part by inducing the expression of p21, a cyclin-dependent kinase (CDK) inhibitor that, among other activities, suppresses the phosphorylation and, hence, the inactivation of pRB. In normal cells, p21 maintains its genuine signature function as a cell cycle inhibitor and anti-proliferative effector. However, upregulation of p21 enables senescent cells to maintain their viability after damage induction, and allows their retention within tissues. Increased expression of p21 is evident in various age-related conditions associated with cellular senescence. The p21 protein (and its mRNA) is therefore an attractive target for diseases such as cancer therapy and other cellular senescence related diseases.

While reducing the present invention to practice, the present inventors have uncovered "hot spot areas" of p21 mRNA which can be specifically targeted by RNA silencing molecules, e.g. DNAzymes, for mediating efficient and specific RNA interference. Accordingly, these RNA silencing molecules can be used in therapeutics of senescent-associated diseases and cancer.

Figure 1:
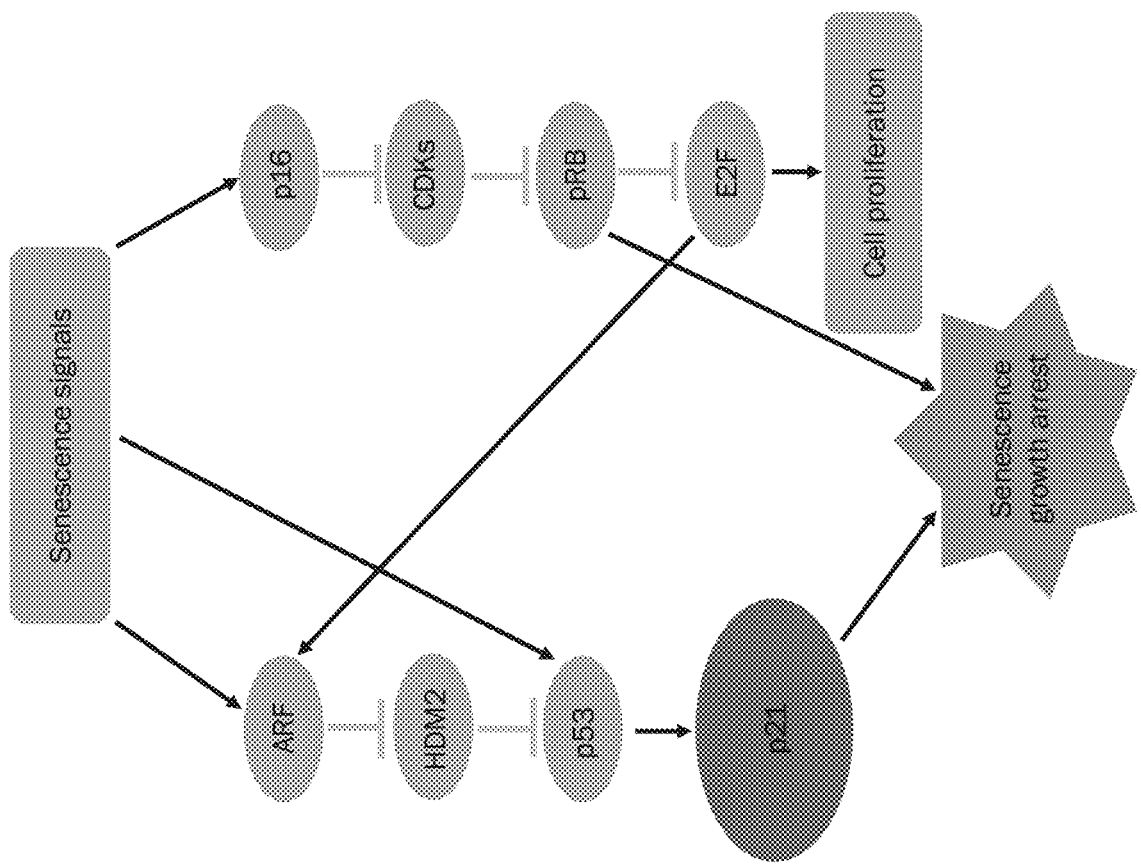
FIG. 1 is a schematic illustration of the p53- and p16-pRB pathways controlling cellular senescence [modified from Campisi, J. and Di Fagagna, FDA, *Nature reviews Molecular cell biology* (2007) 8(9), 729-740]. Abbreviations are as follows: alternate-reading-frame protein (ARF), HDM2 (an E3 ubiquitin ligase), cyclin-dependent kinases (CDKs), p16-retinoblastoma protein (pRB).
Figure 2A:
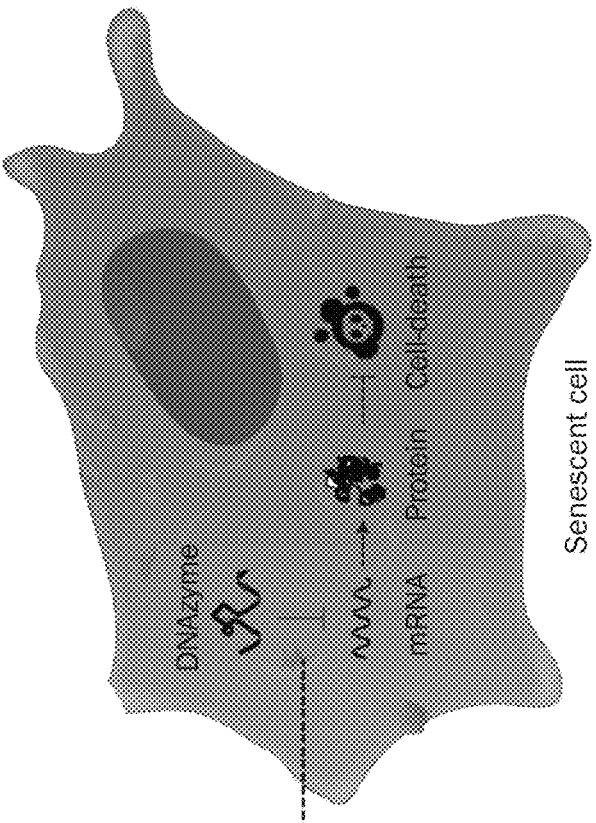
FIGS. 2A-C is a schematic illustration of DNAzyme-mediated senolytic activity.
Figure 2B:
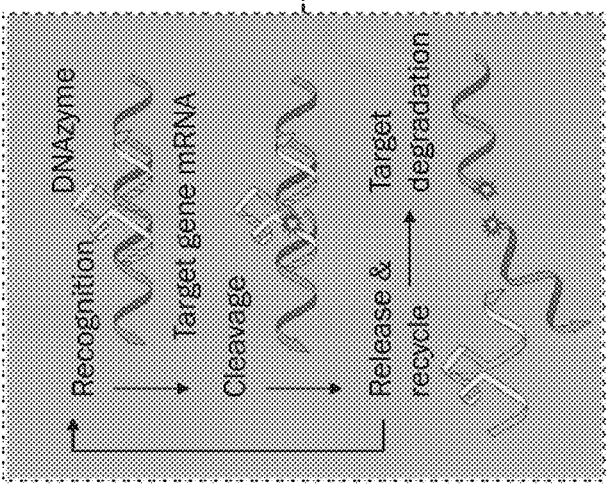
Figure 2C:
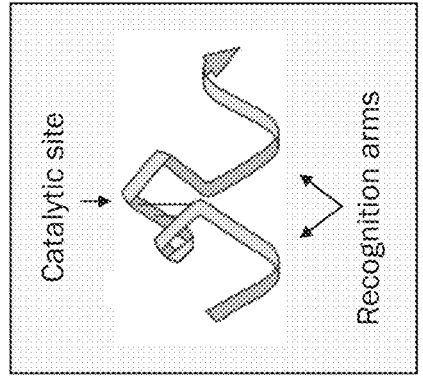
Figure 4:
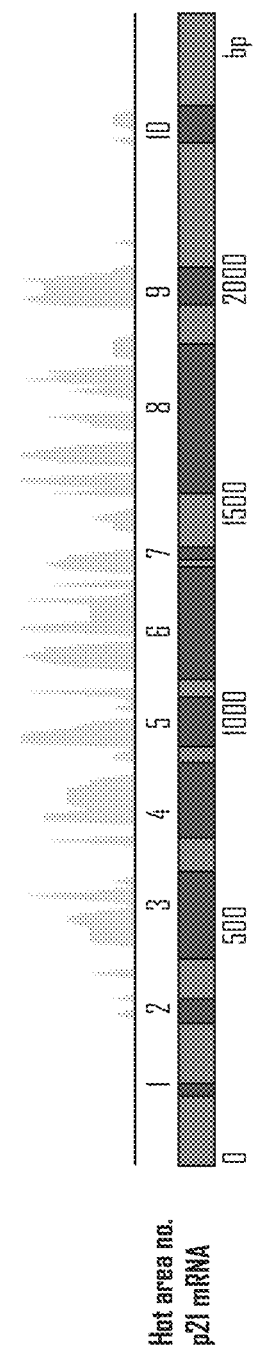
FIG. 4 illustrates an algorithm-based prediction of targetable areas along CDKN1A mRNA sequence. Provided is an in vitro cleavage screen validates hot areas for mRNA targeting. Hot areas are marked in red and numbered from 1 to 10 along the p21 mRNA sequence. The height of the gray peaks above the hot areas illustrates the cleavage efficiency in each area.
Figure 5A:
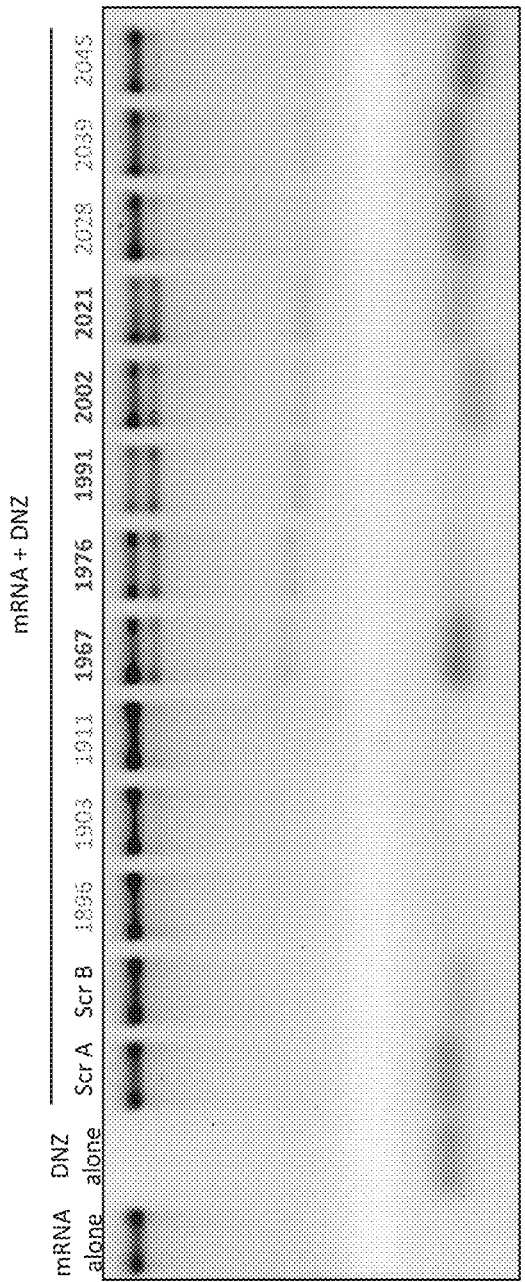
FIGS. 5A-B illustrate the specific in vitro cleavage of human p21 mRNA by DNAzymes.
Figure 5B:
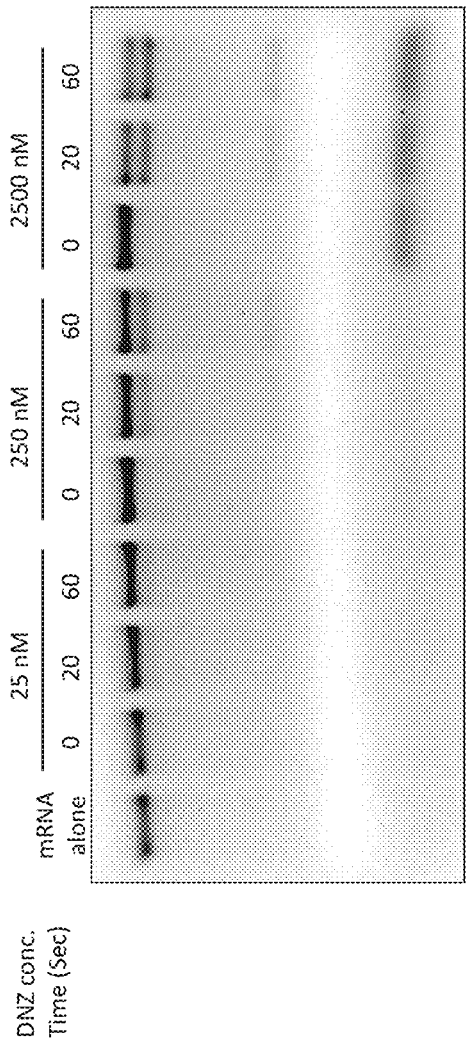
Figure 6:
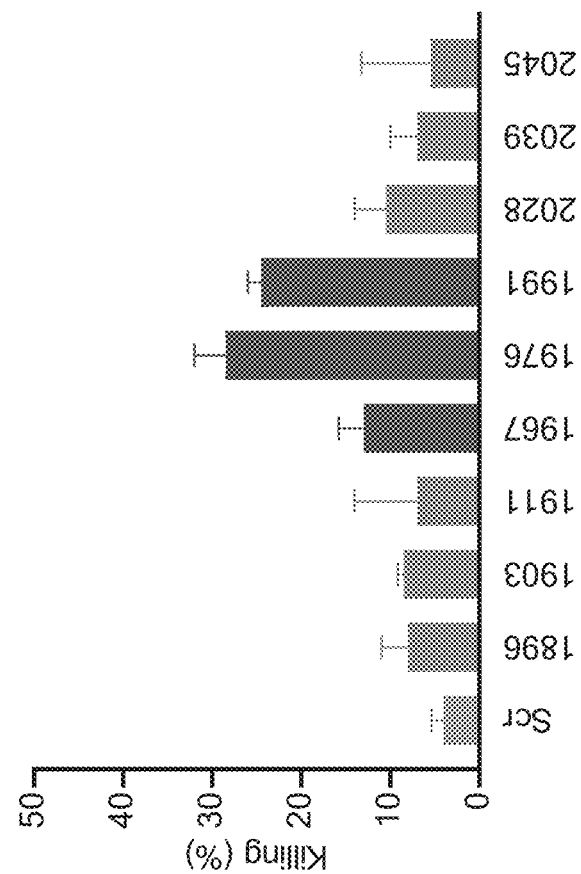
FIG. 6 illustrates that p21-targeting DNAzymes efficiently kill human IMR-90 fibroblast senescent cells. Killing of senescent IMR-90 cells by p21-targeting DNAzymes designed against different locations on CDKN1A mRNA sequence. Of note, scrambled (scr) shows no killing.
Figure 7:
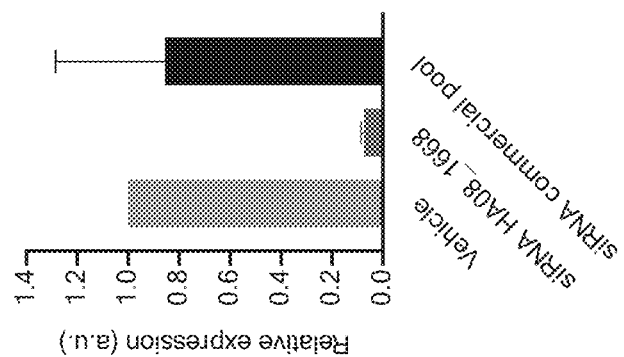
FIG. 7 illustrates a killing assay of senescent BJ cells following transfection with siRNAs targeting HA08 (as set forth in SEQ ID Nos: 141-142).
Figure 8:
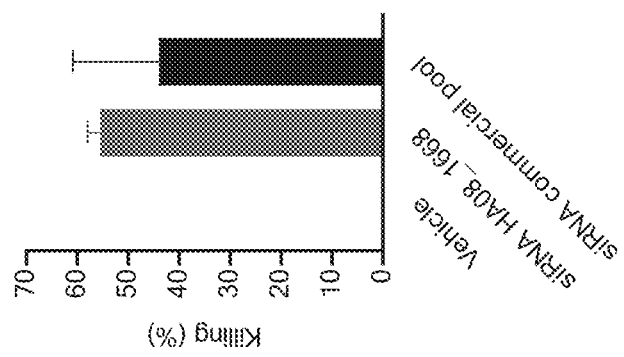
FIG. 8 illustrates relative p21 mRNA levels in senescent BJ cells following transfection with siRNAs targeting HA08 (as set forth in SEQ ID Nos: 141-142), as analyzed by RT-qPCR.
Figure 9:
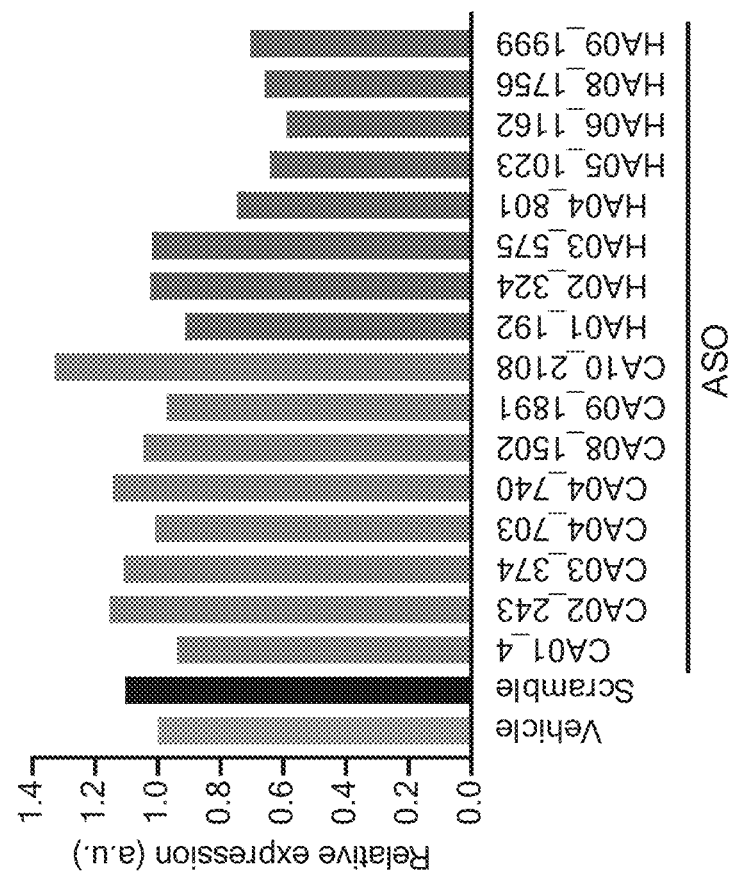
FIG. 9 illustrates relative p21 mRNA levels in senescent BJ cells following transfection with antisense oligonucleotides (ASOs, as set forth in SEQ ID Nos: 143-158 and presented in Table 4, below) directed against cold areas versus hot areas, analyzed by RT-qPCR.

Specifically, the present inventors have devised an algorithm that calculates the secondary and tertiary structure of an mRNA sequence target, determines which mRNA areas are "hot spot areas" for targeting by RNA silencing molecules (e.g. for DNAzyme attack), and designs optimal DNAzymes to cleave it. An algorithm-generated map of the p21 mRNA (as set forth in SEQ ID NO: 1) based on its structure was used to assign a score to areas (also referred to as mRNA regions or target regions) on the mRNA that indicated their accessibility to a silencing molecule of the size and/or structure of DNAzymes (FIG. 4). This map was used to generate a table of optimal potential cleavage areas (referred to as "hot spot areas" or "hot areas"—HA) for RNA silencing molecules, e.g. DNAzymes, and designated these as p21HAs (i.e. HA01-10, see Table 2, below). DNAzymes targeting different hot spot areas, such as "hot area 09", and those targeting areas outside of the hot spot areas, such as those outside of "hot area 09", were designed (see Tables 3A-B), synthesized and tested for cleavage of p21. As illustrated in FIG. 5A, DNAzymes designed to target "hot spot areas" were efficient in cleaving p21, whereas DNAzymes designed to cleave p21 mRNA in regions that are outside the "hot spot areas" showed minimal, if any, cleavage. Furthermore, the cleavage by DNAzymes could be controlled by the dosage and incubation time as shown in FIG. 5B. Moreover, incubation of senescent cells with p21 targeting DNAzymes designed against sequences located in "hot spot areas" displayed marked senolytic activity (FIG. 6). The present inventors further designed and tested the effectivity of other RNA silencing molecules in targeting hot spot areas as compared to areas outside of the hot spot areas (designated "cold areas"). As illustrated in FIGS. 8 and 7, siRNA targeting "hot area 08" significantly downregulated the expression of p21 mRNA in senescent cells and resulted in death of these cells, respectively. Furthermore, antisense oligonucleotides (ASOs) targeting hot spot areas were more efficient in downregulating the expression of p21 mRNA as compared to ASOs targeting areas outside of the hot areas, i.e. cold areas (FIG. 9). Taken together, these results emphasize the potential targeting of "hot spot areas" of p21 mRNA and using RNA silencing molecules to target these areas for therapy, such as senolytics.

Thus, according to one aspect of the present invention there is provided a composition of matter comprising an RNA silencing molecule capable of mediating cleavage of p21 mRNA in a region spanning nucleic acids 1947-2022 corresponding to SEQ ID NO: 1.

According to another aspect of the present invention there is provided a composition of matter comprising an RNA silencing molecule capable of mediating cleavage of p21 mRNA in a region spanning nucleic acids 1455-1473 corresponding to SEQ ID NO: 1.

According to another aspect of the present invention there is provided a composition of matter comprising an RNA silencing molecule capable of mediating cleavage of p21 mRNA in a region spanning nucleic acids 1089-1346 corresponding to SEQ ID NO: 1.

According to another aspect of the present invention there is provided a composition of matter comprising an RNA silencing molecule capable of mediating cleavage of p21 mRNA in a region spanning nucleic acids 1524-1890 corresponding to SEQ ID NO: 1.

According to another aspect of the present invention there is provided a composition of matter comprising an RNA silencing molecule capable of mediating cleavage of p21 mRNA in a region spanning nucleic acids 168-240 corresponding to SEQ ID NO: 1.

According to another aspect of the present invention there is provided a composition of matter comprising an RNA silencing molecule capable of mediating cleavage of p21 mRNA in a region spanning nucleic acids 944-1065 corresponding to SEQ ID NO: 1.

According to another aspect of the present invention there is provided a composition of matter comprising an RNA silencing molecule capable of mediating cleavage of p21 mRNA in a region spanning nucleic acids 475-683 corresponding to SEQ ID NO: 1.

According to another aspect of the present invention there is provided a composition of matter comprising an RNA silencing molecule capable of mediating cleavage of p21 mRNA in a region spanning nucleic acids 797-933 corresponding to SEQ ID NO: 1.

According to another aspect of the present invention there is provided a composition of matter comprising an RNA silencing molecule capable of mediating cleavage of p21 mRNA in a region spanning nucleic acids 290-372 corresponding to SEQ ID NO: 1.

According to another aspect of the present invention there is provided a composition of matter comprising an RNA silencing molecule capable of mediating cleavage of p21 mRNA in a region spanning nucleic acids 2233-2250 corresponding to SEQ ID NO: 1.

The term "p21" also known as "cyclin-dependent kinase inhibitor 1" refers to the mRNA product of the p21 gene (CDKN/A) having a sequence as set forth in SEQ ID NO: 1 (GeneBank Accession No. NM_001291549.3) and homologs, orthologs and variants thereof. Additional exemplary p21 mRNAs include, but are not limited to, those provided in GeneBank Accession Nos. NM_000389.5, NM_001220777.2, NM_001220778.2, NM_001374509.1, NM_001374510.1, NM_001374511.1, NM_001374512.1, NM_001374513.1 and NM_078467.3, or variants thereof.

As mentioned, the present inventors, have uncovered that specific areas within p21 mRNA are "hot spot areas" which can be effectively targeted by RNA silencing molecules, such as DNAzymes, for downregulation, also referred to herein as target regions or target RNA. The target regions of p21 were determined based on the secondary and tertiary structure of the p21 mRNA sequence and its accessibility to RNA silencing molecules (e.g. DNAzyme molecules).

As used herein, the phrase "target RNA" or "target region of an RNA" refers to an RNA molecule (e.g. an mRNA molecule encoding a p21 gene product) that is a target for downregulation. Similarly, the phrase "target site" refers to a sequence within a target RNA (e.g. within the p21 mRNA sequence) that is "targeted" for cleavage mediated by a RNA silencing molecule (e.g. DNAzyme molecule) that contains sequences within its substrate binding domains that are complementary to the target site (as discussed below).

The target regions of p21 mRNA may vary in size and may comprise, for example, 10400 nucleotides, 10-200 nucleotides, 10-100 nucleotides, 10-50 nucleotides, 10-25 nucleotides, 25-50 nucleotides, 50-75 nucleotides, 75-100 nucleotides, 100-150 nucleotides, 150-200 nucleotides, 200-250 nucleotides, 250-300 nucleotides, 300-350 nucleotides, or 350-400 nucleotides. According to a specific embodiment, the target regions of p21 mRNA may comprise, for example, 18 nucleotides, 19 nucleotides, 73 nucleotides, 74 nucleotides, 83 nucleotides, 122 nucleotides, 137 nucleotides, 209 nucleotides, 258 nucleotides, or 367 nucleotides.

According to one embodiment, the target region of p21 mRNA is a region spanning nucleic acids 1947-2022 corresponding to SEQ ID NO: 1 (also referred to as hot area HA09, e.g. comprising the sequence set forth in SEQ ID NO: 3).

According to one embodiment, the target region of p21 mRNA is a region spanning nucleic acids 1455-1473 corresponding to SEQ ID NO: 1 (also referred to as hot area HA07, e.g. comprising the sequence set forth in SEQ ID NO: 4).

According to one embodiment, the target region of p21 mRNA is a region spanning nucleic acids 1089-1346 corresponding to SEQ ID NO: 1 (also referred to as hot area HA06, e.g. comprising the sequence set forth in SEQ ID NO. 5).

According to one embodiment, the target region of p21 mRNA is a region spanning nucleic acids 1524-1890 corresponding to SEQ ID NO: 1 (also referred to as hot area HA08, e.g. comprising the sequence set forth in SEQ ID NO: 6).

According to one embodiment, the target region of p21 mRNA is a region spanning nucleic acids 168-240 corresponding to SEQ ID NO: 1 (also referred to as hot area HA01, e.g. comprising the sequence set forth in SEQ ID NO: 7).

According to one embodiment, the target region of p21 mRNA is a region spanning nucleic acids 944-1065 corresponding to SEQ ID NO: 1 (also referred to as hot area HA05, e.g. comprising the sequence set forth in SEQ ID NO: 8).

According to one embodiment, the target region of p21 mRNA is a region spanning nucleic acids 475-683 corresponding to SEQ ID NO: 1 (also referred to as hot area HA03, e.g. comprising the sequence set forth in SEQ ID NO: 9).

According to one embodiment, the target region of p21 mRNA is a region spanning nucleic acids 797-933 corresponding to SEQ ID NO: 1 (also referred to as hot area HA04, e.g. comprising the sequence set forth in SEQ ID NO: 10).

According to one embodiment, the target region of p21 mRNA is a region spanning nucleic acids 290-372 corresponding to SEQ ID NO: 1 (also referred to as hot area HA02, e.g. comprising the sequence set forth in SEQ ID NO: 11).

According to one embodiment, the target region of p21 mRNA is a region spanning nucleic acids 2233-2250 corresponding to SEQ ID NO: 1 (also referred to as hot area HA10, e.g. comprising the sequence set forth in SEQ ID NO: 12).

According to one embodiment, the target region of p21 mRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence homology or identity to the sequence set forth in SEQ ID NOs: 3-12. According to a specific embodiment, the target region of p21 mRNA comprises a sequence that is comparable (e.g. identical) to the sequence set forth in SEQ ID NOs: 3-12.

As used herein, "sequence identity" or "identity" in the context of two nucleic acid sequences includes reference to the residues in the two sequences which are the same when aligned.

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences of the invention and not over portions thereof.

The degree of homology or identity between two or more sequences can be determined using various known sequence comparison tools. Following is a non-limiting description of such tools which can be used along with some embodiments of the invention.

When starting with a polynucleotide sequence and comparing to other polynucleotide sequences the EMBOSS-6.0.1 Needleman-Wunsch algorithm (available from emboss (dot)sourceforge(dot)net/apps/cvs/emboss/apps/needle(dot) html) can be used.

According to some embodiment, determination of the degree of homology further requires employing the Smith-Waterman algorithm (for protein-protein comparison or nucleotide-nucleotide comparison).

The term "RNA silencing molecule" refers to a non-coding RNA molecule, i.e. an RNA sequence that is not translated into an amino acid sequence and does not encode a protein, capable of mediating RNA silencing or RNA interference (RNAi).

The term "RNA silencing" or "RNAi" refers to a cellular regulatory mechanism in which the RNA silencing molecule mediates, in a sequence specific manner, co- or post-transcriptional inhibition of gene expression or translation.

As mentioned, the RNA silencing molecule of the invention is capable of mediating cleavage of p21 mRNA. The term "mediating cleavage" refers to direct catalytic activity (i.e. by the RNA silencing molecule) or indirect catalytic activity (i.e. by an enzyme recruited by the RNA silencing molecule) which leads to cleavage and RNA interference of the p21 mRNA.

According to one embodiment, the RNA silencing molecule is a catalytically active molecule.

According to one embodiment, the RNA silencing molecule is synthetic. As used herein "synthetic" refers to a non-natural molecule.

Following is a detailed description on RNA silencing molecules that can be used according to specific embodiments of the present invention including, for example, DNAzymes, Ribozymes, antisense, siRNA, shRNA and miRNA molecules.

DNAzyme (also referred to as a "DNA enzyme" or "deoxyribozyme")—as used herein refers to a DNA molecule that has complementarity in a substrate binding domain or region to a ribonucleic acid (RNA) substrate and is capable of catalyzing a modification (such as a cleavage) of the nucleic acid substrate. Typically, the complementarity functions to allow sufficient hybridization of the DNAzyme molecule to the substrate at a target region to allow the intermolecular cleavage of the substrate to occur thereby functionally inactivating it. The cleavage can occur via two optional mechanisms: (i) intrinsic catalytic activity of the DNAzyme (ii) recruitment of RNAse H to the hybridization site, leading to cleavage of the target RNA.

The term "nucleic acid" as used herein generally refers to a molecule (single-stranded or double-stranded oligomer or polymer) of DNA or RNA or a derivative, mimic or analog thereof, comprising a nucleobase. A nucleobase includes, for example, a naturally occurring purine or pyrimidine base found in DNA (e.g., an adenine "A", a guanine "G", a thymine "T", or a cytosine "C") or a naturally occurring purine or pyrimidine base found in RNA (e.g., an adenine "A", a guanine "G", an uracil "U" or a cytosine "C"). The term "nucleic acid" encompasses the terms "oligonucleotide" and "polynucleotide" and "nucleotides", each as a subgenus of the term "nucleic acid". The term "nucleic acid" further includes nucleic acids derived from synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions, as further discussed herein below.

The DNAzyme typically comprises a pair of binding arms which are complementary to binding regions on the nucleic acid substrate (e.g. p21 mRNA). Each binding arm of the DNAzyme comprises a number of nucleotides to permit sufficient bonding between the DNAzyme and its substrate to facilitate DNAzyme activity (i.e. cleavage of the p21 substrate at the target cleavage site). The binding arms may be the same or different lengths. Furthermore, the binding arms may comprise modified nucleotides, including modified bases, backbone, sugars and/or linkages to the extent that such modifications do not have an adverse effect on binding activity of the DNAzyme to the substrate (e.g. p21 mRNA). Such modifications are discussed below.

For example, each binding arm may comprise 5-25 nucleotides, 5-10 nucleotides, 10-15 to nucleotides, 15-20 nucleotides or 20-25 nucleotides (e.g. deoxyribonucleotides or ribonucleotides). According to one embodiment, each binding arm comprises at least about 5, 6, 7, 8, 9, 10, 11, 12, 13, 14, 15, 16, 17, 18, 19, 20, 21, 22, 23, 24 or 25 nucleotides (e.g. deoxyribonucleotides or ribonucleotides). According to a specific embodiment, each binding arm comprises at least about 8-10 nucleotides, e.g. 9 nucleotides (e.g. deoxyribonucleotides or ribonucleotides).

According to a specific embodiment, each of the binding arms of the DNAzyme molecule comprises no more than 6, 7, 8, 9, 10, 11, 12, 13, 14 or 15 nucleotides (e.g. deoxyribonucleotides or ribonucleotides).

As mentioned, the DNAzyme targets a nucleic acid-based substrate comprising binding regions which are essentially complementary to the binding arms of the DNAzyme, and which hybridize with the binding arms of the DNAzyme. The binding regions need not be fully complementary with the binding arms of the DNAzyme, provided that they hybridize sufficiently with the DNAzyme such that the catalytic activity of the DNAzyme is not adversely affected (e.g. exhibit at least about 70%, 80%, 85%, 90%, 95%, 97% or 99% complementarity). Typically, the cleavage site is within a target region of the substrate situated between the binding regions. The terminal 5'- and 3' ends of the target region are each linked to a binding region at the appropriate corresponding terminus (e.g. 5' to 3') of the binding arm.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, binding with specificity by substrate binding domains of a DNAzyme of some embodiments of the invention such that the catalytic domain of the DNAzyme is brought in to close enough proximity with a target sequence to permit catalytic cleavage of the target sequence. The degree of complementarity between the substrate binding domains of the DNAzyme and the target region of a RNA (e.g. a p21 mRNA) can vary, but no more than by what is required in order to permit the DNAzyme to cleave or mediate cleavage (e.g. by RNase H) of the target region. Determination of binding free energies for nucleic acid molecules to determine percent complementarity is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). The terms "100% complementary". "fully complementary", and "perfectly complementary" indicate that all of the contiguous residues of a nucleic acid sequence can hydrogen bond with the same number of contiguous residues in a second nucleic acid sequence.

The DNAzyme additionally comprises a catalytic domain (also referred to as catalytic core) between the binding arms, generally in the form of a loop, which includes single-stranded DNA, and may optionally include double-stranded regions. The terminal 5'- and 3' ends of the catalytic domain are each linked to a binding arm at the appropriate corresponding terminus of the binding arm (e.g. 5' to 3'). The catalytic region may incorporate modified nucleotides, including modified bases, backbone, sugars and/or linkages to the extent that such modifications do not have an adverse effect on catalytic activity (i.e. cleavage activity) of the DNAzyme, such modifications are discussed below.

The size of the catalytic domain in each DNAzyme may include, for example, 5-100 nucleotides, e.g. 5-10 nucleotides, 10-20 nucleotides, 20-30 nucleotides, 30-40 nucleotides, 40-50 nucleotides, 50-75 nucleotides or 75-100 nucleotides (e.g. deoxyribonucleotides or ribonucleotides). According to one embodiment, the catalytic domain comprises at least about 5, 10, 15, 20, 25, 30, 35, 40, 45 or 50 nucleotides (e.g. deoxyribonucleotides or ribonucleotides). According to a specific embodiment, the catalytic domain comprises at least about 10, It, 12, 13, 14, 15, 16, 17, 18, 19, 20, 21, 22, 23, 24, 25, 30, 35, 40, 45 or 50 nucleotides (e.g. deoxyribonucleotides or ribonucleotides).

According to a specific embodiment, the catalytic domain of the DNAzyme molecule comprises no more than 14, 15, 16, 17, 18, 19, 20, 21, 22, 23, 24, 25, 30, 35, 40, 45 or 50 nucleotides (e.g. deoxyribonucleotides or ribonucleotides).

Exemplary DNAzyme catalytic domains which may be used in accordance with some embodiments of the invention, include, but are not limited to, the catalytic cores of lanthanide-dependent DNAzymes such as Ce13d, Lu12 and Tm7; the catalytic cores of magnesium-dependent DNAzymes such as 17E and 10-23, 8-17: the catalytic cores of uranyl-specific DNAzymes such as 39E and EHg0T; the catalytic cores of lead-dependent DNAzymes such as GR5; and functionally equivalent DNAzyme catalytic cores derived from any of these which exhibit a high degree of sequence identity, e.g. at least about 80%, 85%, 90%, 95% or 99%. The term "functionally equivalent" refers to DNAzyme catalytic cores which retain the ability to cleave the DNAzyme substrate or to recruit RNase H. Additional catalytic cores of DNAzymes which may be used in accordance with some embodiments of the invention include e.g. Bipartite I and Bipartite II (discussed in Feldman and Sen. *Journal of molecular biology* (2001) 313(2): 283-294, incorporated herein by reference), 10MD5 and I-R3 (discussed in Hollenstein, *Molecules* (2015) 20(11): 20777-20804, and in Zhou et al. *Theranostics*. 2017; 7(4): 1010-1025, both incorporated herein by reference).

According to one embodiment, the DNAzyme is a 10-23 type DNAzyme (i.e. comprises the 10-23 catalytic core).

The term "10-23" refers to a general DNAzyme model (discussed in detail in Sontoro and Joyce, PNAS (1997) 94 (9):4262-4266, incorporated herein by reference). DNAzymes of the 10-23 model typically have a catalytic domain of 15 nucleotides, which are flanked by two substrate binding domains. The catalytic domain of 10-23 DNAzymes typically comprises the sequence ggctagctacaacga (SEQ ID NO: 128). The DNAzyme 10-23 typically cleaves mRNA strands that contain an unpaired purine-pyrimidine pair. The length of the substrate binding domains of 10-23 DNAzymes is variable and may be of either equal length or variable length. According to one embodiment, the length of the substrate binding domains ranges between 6 and 14 nucleotides. e.g. between 8 and 12 nucleotides (e.g. 7, 8, 9, 10, 11, 12 nucleotides, e.g. 9 nucleotides).

According to one embodiment, the DNAzyme is a 8-17 type DNAzyme (i.e. comprises the 8-17 catalytic core).

The term "8-17" refers to a general DNAzyme model (discussed in detail in Sontoro and Joyce, PNAS (1997) 94 (9):4262-4266, incorporated herein by reference). DNAzymes of the 8-17 model typically have a catalytic domain of 14 nucleotides, which are flanked by two substrate binding domains. The catalytic domain of 8-17 DNAzymes typically comprises the sequence TCCGAGCCGGACGA (SEQ ID NO: 129). The length of the substrate binding domains of 8-17 DNAzymes is variable and may be of either equal length or variable length. According to one embodiment, the length of the substrate binding domains ranges between 6 and 14 nucleotides, e.g. between 8 and 12 nucleotides (e.g. 7, 8, 9, 10, 11, 12 nucleotides, e.g. 8 nucleotides).

According to one embodiment, the DNAzyme catalytic domain comprises the 16.2-11 catalytic core: GTGACCCCUUG (SEQ ID NO: 130): the 9-86 catalytic core: UCAUGCAGCGCGUAGUGUC (SEQ ID NO: 131): the 12-91 catalytic core: UGAUGCAGCGCAUGUGUC (SEQ ID NO: 132); the FR17_6 catalytic core: AAGCAGUUAAGAC (SEQ ID NO: 133) or the Bipartite I or Bipartite II catalytic core:

(SEQ ID NO: 134)
AAGGAGGTAGGGGTTCCGCTCC.

According to one embodiment, the DNAzyme is an inducible DNAzyme. Exemplary inducible DNAzymes are MNAzymes (discussed in detail in Mokany et al., *Journal of the American Chemical Society* (2010) 132(3): 1051-1059, incorporated herein by reference). Specifically, MNAzymes are multicomponent complexes that produce amplified "output" signals in response to specific "input" signals. Multiple oligonucleotide partzymes assemble into active MNAzymes only in the presence of an input assembly facilitator such as a target nucleic acid. Once formed, MNAzymes catalytically modify a generic substrate, generating an amplified output signal that heralds the presence of the target while leaving the target intact.

According to a specific embodiment, the DNAzyme molecule comprises 20-80 nucleotides, e.g. 20-70 nucleotides, e.g. 20-60 nucleotides, e.g. 20-50 nucleotides, e.g. 20-40 nucleotides, e.g. 20-30 nucleotides, e.g. 30-50 nucleotides, e.g. 30-40 nucleotides (e.g. deoxyribonucleotides or ribonucleotides). According to a specific embodiment, the DNAzyme molecule comprises at least about 20, 25, 30, 31, 32, 33, 34, 35, 36, 37, 38, 39, 40, 45, 50, 55, 60, 65, 70 or 75 nucleotides (e.g. deoxyribonucleotides or ribonucleotides).

According to a specific embodiment, the DNAzyme molecule comprises no more than 20-80 nucleotides, e.g. 20-70 nucleotides, e.g. 20-60 nucleotides, e.g. 20-50 nucleotides, e.g. 20-40 nucleotides, e.g. 20-30 nucleotides, e.g. 30-50 nucleotides, e.g. 30-40 nucleotides (e.g. deoxyribonucleotides or ribonucleotides). According to a specific embodiment, the DNAzyme molecule comprises no more than e.g. 30, 31, 32, 33, 34, 35, 36, 37, 38, 39, 40, 41, 42, 43, 44, 45, 50, 55, 60, 65, 70, 75 or 80 nucleotides (e.g. deoxyribonucleotides or ribonucleotides).

In some embodiments, one or more mutations or modifications within the catalytic domain of the DNAzyme molecule can be carried out to increase the catalytic activity of the DNAzyme molecule (e.g. by insertion, deletion, substitution or point mutation of nucleic acids). It is to be understood that any mutation or modification, e.g., within the substrate binding domain sequences or catalytic domain sequence, must not adversely impact the molecule's ability to induce catalysis (e.g. cleave) the specific substrate, i.e. p21.

According to a specific embodiment, the modification comprises the insertion, deletion, substitution or point mutation of 1-10 nucleotides, e.g. 1-8 nucleotides, e.g. 1-6 nucleotides, e.g. 1-5 nucleotides, e.g. 1-4 nucleotides, e.g. 1-3 nucleotides, or e.g. 1-2 nucleotides in the catalytic domain of the DNAzyme.

According to a specific embodiment, the modification comprises the insertion, deletion, substitution or point mutation of 1, 2, 3, 4, 5, 6, 7, 8, 9, 10 nucleotides. e.g. 1 or 2 nucleotides, in the catalytic domain of the DNAzyme.

Additionally or alternatively, the DNAzyme molecule may be modified to alter the length of the substrate binding domains of the DNAzyme molecule. The substrate binding domains of the DNAzyme molecule have binding specificity for and associate with a complementary sequence of bases within a target region of a substrate nucleic acid sequence (as discussed above). Methods of altering the length of the recognition domains are known in the art and include direct synthesis and PCR, for example.

Alteration of the length of the recognition domains of a DNAzyme molecule can have a desirable effect on the binding specificity of the DNAzyme molecule. For example, an increase in the length of the substrate binding domains can increase binding specificity between the DNAzyme molecule and the complementary base sequences of a target region in a substrate polynucleotide (i.e. p21). In addition, an increase in the length of the substrate binding domains can also increase the affinity with which the DNA molecule binds to the polynucleotide substrate. In various embodiments, these altered substrate binding domains in the DNAzyme molecule confer increased binding specificity and affinity between the DNAzyme molecule and its substrate (i.e. p21), however, it may decrease catalytic efficiency of the DNAzyme. Therefore, one of skill in the art will appreciate that alteration of the length of the recognition domains is a balance of optimal binding and catalytic activity.

According to a specific embodiment, the modification comprises the addition of 1-10 nucleotides, e.g. 1-8 nucleotides, e.g. 1-6 nucleotides, e.g. 1-5 nucleotides, e.g. 1-4 nucleotides, e.g. 1-3 nucleotides, or e.g. 1-2 nucleotides to the substrate binding domain (i.e. binding arm) of the DNAzyme.

According to a specific embodiment, the modification comprises the addition of 1, 2, 3, 4, 5, 6, 7, 8, 9, 10 nucleotides, e.g. 1 or 2 nucleotides, to the substrate binding domain (i.e. binding arm) of the DNAzyme.

Additionally or alternatively, the substrate binding domains of the DNAzyme molecule may be modified to improve binding to the p21 mRNA target. Accordingly, the modification may comprise the insertion, deletion, substitution or point mutation of 1, 2, 3, 4, 5, 6, 7, 8, 9, 10 nucleotides, e.g. 1 or 2 nucleotides, in the substrate binding domain of the DNAzyme According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in any one of SEQ ID NOs: 15-123.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in SEQ ID NO: 18.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in SEQ ID NO: 19.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in SEQ ID NO: 20.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in SEQ ID NO: 21.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in SEQ ID NO: 22.

According to one embodiment, the DNAzyme molecule comprises a nucleic acid sequence set forth in any one of SEQ ID NOs: 15-123.

According to a specific embodiment, the DNAzyme molecule comprises a nucleic acid sequence set forth in SEQ ID NO: 18.

According to a specific embodiment, the DNAzyme molecule comprises a nucleic acid sequence set forth in SEQ ID NO: 19.

According to a specific embodiment, the DNAzyme molecule comprises a nucleic acid sequence set forth in SEQ ID NO: 20.

According to a specific embodiment, the DNAzyme molecule comprises a nucleic acid sequence set forth in SEQ ID NO: 21.

According to a specific embodiment, the DNAzyme molecule comprises a nucleic acid sequence set forth in SEQ ID NO: 22.

Ribozyme (also called "an RNA enzyme" or "catalytic RNA")—as used herein refers to a short (e.g. less than 200 bases) RNA molecule acting as an enzyme or a complex molecule comprising the RNA molecule. The ribozyme typically has a three-dimensional structure, which performs a chemical reaction and has a property of self-clearing or cleaving a target RNA. Such ribozymes may include a hammerhead ribozyme, a VS ribozyme and a hairpin ribozyme.

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Antisense—Antisense (ASO) is a single stranded RNA designed to prevent or inhibit expression of a gene by specifically hybridizing to its mRNA. Antisense molecules typically comprise 8-20 oligonucleotides (e.g. 12- to 16-mer).

Two types of ASOs have been used in clinical trials. "morpholino" ASOs that impair mRNA translation into protein, and "gapmer" ASOs responsible for mRNA destruction through the recruitment of the RNase H enzyme that specifically cleaves RNA within the RNA:DNA duplex.

Design of antisense molecules which can be used to efficiently downregulate p21 must be affected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)]. Such algorithms have been successfully used to implement an antisense approach in cells.

In addition, several approaches for designing and predicting efficiency of specific oligonucleotides using an in vitro system were also published (Matveeva et al., Nature Biotechnology 16: 1374-1375 (1998)].

Thus, the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Exemplary antisense molecules which can be used according to some embodiments of the invention are those set forth in SEQ ID NOs: 143-150.

DsRNA, siRNA and shRNA—The presence of long dsR-NAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392: Paddison P. J., et al., Proc. Natl Acad. Sci. USA. 2002:99:1443-1448; Tran N., et al., FEBS Lett. 2004:573: 127-134].

According to an embodiment of the invention, the long dsRNA are specifically designed not to induce the interferon and PKR pathways for down-regulating gene expression. For example, Shinagwa and Ishii [Genes & Dev. 17 (11): 1340-1345, 2003] have developed a vector, named pDE-CAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is suggested to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the p21 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi (dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites within the hot areas of p21 mRNA (e.g. p21 hot areas HA01-10) are preferably selected for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

An exemplary siRNA which can be used according to some embodiments of the invention is the siRNA set forth in SEQ ID NOs: 141-142.

It will be appreciated that, and as mentioned hereinabove, the RNA silencing agent of some embodiments of the invention need not be limited to those molecules containing only RNA, but further encompasses chemically-modified nucleotides and non-nucleotides.

miRNA and miRNA mimics—According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression, miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding.

Moreover, sufficient base pairing at the 3' can compensate for insufficient pairing at the 5' (Brennecke et al. 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Preparation of miRNAs mimics can be effected by any method known in the art such as chemical synthesis or recombinant methods.

Regardless of the RNA silencing molecule used, RNA silencing is preferably affected by cleavage of p21 mRNA.

As mentioned, the cleavage can occur via two optional mechanisms: (i) intrinsic catalytic activity of the RNA silencing molecule, e.g. DNAzyme or Ribozyme: or (ii) by recruitment of RNAse H or RISC complex to the hybridization site, leading to cleavage of the target RNA (e.g. by antisense, siRNA, miRNA).

According to one embodiment, the RNA silencing molecule (e.g. DNAzyme molecule) is capable of specifically cleaving a p21 mRNA sequence as set forth in any one of SEQ ID NOs: 3-12 (e.g. p21 hot areas HA01-10).

According to one embodiment, the RNA silencing molecule is capable of mediating cleavage (e.g. by RNase H or by RISC) of a p21 mRNA sequence as set forth in any one of SEQ ID NOs: 3-12 (e.g. p21 hot areas HA01-10).

According to one embodiment, silencing of the p21 mRNA (e.g. cleavage of the p21 mRNA) results in down-regulation of mRNA and/or protein expression levels.

According to one embodiment, down regulating p21 expression level refers to the absence of p21 mRNA and/or protein, as detected by RT-PCR or Western blot/Immunofluorescent staining, respectively.

According to other embodiment, down regulating p21 expression level refers to a decrease in the level of p21 mRNA and/or protein, as detected by RT-PCR or Western blot/Immunofluorescent staining, respectively. The reduction may be by at least a 10%, at least 20%, at least 30%, at least 40%, at least 50%, at least 60%, at least 70%, at least 80%, at least 90%, at least 95% or at least 99% reduction, as compared to the expression level of p21 prior to the treatment.

Down regulation of expression may be either transient or permanent.

Various modifications to RNA silencing molecules (e.g. DNAzyme molecules) can be made to enhance the utility of these molecules. Such modifications can enhance affinity for the nucleic acid target, increase activity, increase specificity, increase stability and decrease degradation (e.g. in the presence of nucleases), increase shelf-life, enhance half-life and/or improve introduction of such RNA silencing molecules (e.g. DNAzyme molecules) to the target site (for example, to enhance penetration of cellular membranes, confer the ability to recognize and bind to targeted cells, and enhance cellular uptake), as discussed in further detail below.

According to one embodiment, the RNA silencing molecule (e.g. DNAzyme molecule) comprises a modification selected from an insertion, deletion, substitution or point mutation of a nucleic acid, as long as the molecule retains at least about 80%, 85%, 90%, 95%, 99% or 100% of its the biological activity (i.e. silencing activity, e.g. mediating catalytic activity on the p21 substrate).

It will be appreciated that insertions, deletions, substitutions or point mutations can be generated using methods that produce random or specific alterations. These mutations or modifications can, for example, change the length of, or alter the nucleotide sequence of, a loop, a spacer region or the substrate binding domain (e.g. binding arm of the DNAzyme as discussed above) or add one or more non-nucleotide moieties to the molecule to, for example, increase stability and/or decrease degradation.

The RNA silencing molecule (e.g. DNAzyme molecule) of the invention is optimally stable within cells until translation of the target RNA has been inhibited long enough to reduce the levels of the undesirable protein. This period of time varies between hours to days depending upon the cell type and state (e.g. senescence). Although DNAzyme molecules as described herein are considered advantageous over RNA based molecules in that DNAzymes are less sensitive to degradation, in some embodiments it is desirable to further increase stability and nuclease resistance of the DNAzymes. Furthermore, when RNA based molecules are utilized, these may be modified to increase their stability and nuclease resistance.

According to one embodiment, the modification is selected from the group consisting of a nucleobase modification, a sugar modification, and an internucleotide linkage modification (e.g. phosphorus-modified internucleotide linkage), as is broadly described herein under.

According to one embodiment, the RNA silencing molecule (e.g. DNAzyme molecule) comprises one or more chemical modifications.

Any chemical modification can be applied to the RNA silencing molecule (e.g. DNAzyme molecule) of the invention as long as the molecule retains at least about 80%, 85%, 90%, 95%, 99% or 100% of its the biological activity (i.e. silencing activity. e.g. mediating catalytic activity on the p21 substrate).

According to one embodiment, the RNA silencing molecule (e.g. DNAzyme molecule) includes at least one base (e.g. nucleobase) modification or substitution.

As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine: xanthine; hypoxanthine; 2-aminoadenine; 6-methyl and other alkyl derivatives of adenine and guanine: 2-propyl and other alkyl derivatives of adenine and guanine: 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808: Kroschwitz. J. I., ed. (1990), "The Concise Encyclopedia Of Polymer Science And Engineering," pages 858-859, John Wiley & Sons; Englisch et al. (1991), "Angewandte Chemie." International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993). "Antisense Research and Applications," pages 276-278, CRC Press, Boca Raton), and are presently preferred base substitutions, even more particularly when combined with 2'-O-methoxyethyl sugar modifications. Additional base modifications are described in Deleavey and Damha, *Chemistry and Biology* (2012) 19: 937-954, incorporated herein by reference.

According to one embodiment, the modification is in the backbone (i.e. in the internucleotide linkage and/or the sugar moiety).

Sugar modification of nucleic acid molecules have been extensively described in the art (see PCT International Publication Nos. WO 92/07065. WO 93/15187, WO 98/13526, and WO 97/26270; U.S. Pat. Nos. 5,334,711; 5,716,824; and 5,627,053; Perrault et al., 1990: Pieken et al., 1991; Usman & Cedergren, 1992; Beigelman et al., 1995; Karpeisky et al., 1998; Eamshaw & Gait, 1998; Verma & Eckstein. 1998; Burlina et al., 1997; all of which are incorporated herein by reference). Such publications describe general methods and strategies to determine the location of incorporation of sugar, base, and/or phosphate modifications and the like into nucleic acid molecules without modulating catalysis. Exemplary sugar modifications include, but are not limited to, 2'-modified nucleotide, e.g., a 2'-deoxy, 2'-fluoro (2'-F), 2'-deoxy-2'-fluoro, 2'-O-methyl (2'-O-Me), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-Fluoroarabinooligonucleotides (2'-F-ANA), 2'-O—N-methylacetamido (2'-O-NMA), 2'-NH2 or a locked nucleic acid (LNA). Additional sugar modifications are described in Deleavey and Damha, *Chemistry and Biology* (2012) 19: 937-954, incorporated herein by reference.

Thus, for example, oligonucleotides can be modified to enhance their stability and/or enhance biological activity by modification with nuclease resistant groups, for example, the RNA silencing molecule (e.g. DNAzyme molecule) of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), e.g. inclusion of nucleic acid analogues in which the ribose ring is "locked" by a methylene bridge connecting the 2'-0 atom and the 4'-C atom, ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to the target. The inclusion of pyranose sugars in the oligonucleotide backbone can also decrease endonucleolytic cleavage. The binding arms may further include peptide nucleic acid (PNA) in which the deoxyribose (or ribose) phosphate backbone in the DNA is replaced with a polyamide backbone, or may include polymer backbones, cyclic backbones, or acyclic backbones. The binding regions may incorporate sugar mimetics, and may additionally include protective groups, particularly at terminal ends thereof, to prevent undesirable degradation (as discussed below).

Exemplary internucleotide linkage modifications include, but are not limited to, phosphorothioate, chiral phosphorothioate, phosphorodithioate, phosphotriester, aminoalkyl phosphotriester, methyl phosphonate, alkyl phosphonate (including 3'-alkylene phosphonates), chiral phosphonate, phosphinate, phosphoramidate (including 3'-amino phosphoramidate), aminoalkylphosphoramidate, thionophosphoramidate, thionoalkylphosphonate, thionoalkylphosphotriester, boranophosphate (such as that having normal 3'-5' linkages, 2'-5' linked analogues of these, and those having inverted polarity wherein the adjacent pairs of nucleoside units are linked 3'-5' to 5'-3' or 2'-5' to 5'-2'), boron phosphonate, phosphodiester, phosphonoacetate (PACE), morpholino, amidate carbamate, carboxymethyl, acetamidate, polyamide, sulfonate, sulfonamide, sulfamate, formacetal, thioformacetal, alkylsilyl, substitutions, peptide nucleic acid (PNA) and/or threose nucleic acid (TNA). Various salts, mixed salts, and free acid forms of the above modifications can also be used. Additional internucleotide linkage modifications are described in Deleavey and Damha. *Chemistry and Biology* (2012) 19: 937-954; and Hunziker & Leumann, 1995 and De Mesmaeker et al., 1994, both incorporated herein by reference.

According to a specific embodiment, the modification comprises modified nucleoside triphosphates (dN*TPs).

According to one embodiment, the modification comprises an edge-blocker oligonucleotide.

According to a specific embodiment, the edge-blocker oligonucleotide comprises a phosphate, an inverted dT and an amino-C7.

According to a specific embodiment, the modification comprises an inverted deoxythymidine (dT) positioned in at least one terminal end of the DNAzyme molecule. For example, an inverted dT can be incorporated at the 3-end of an oligo, leading to a 3'-3' linkage which inhibits both degradation by 3' exonucleases and extension by DNA polymerases.

According to one embodiment, the RNA silencing molecule (e.g. DNAzyme molecule) is modified to comprise one or more protective group, e.g. 5' and/or 3'-cap structures.

As used herein, the phrase "cap structure" is meant to refer to chemical modifications that have been incorporated at either terminus of the oligonucleotide (see e.g., U.S. Pat. No. 5,998,203, incorporated by reference herein). These terminal modifications protect the nucleic acid molecule from exonuclease degradation, and can help in delivery and/or localization within a cell. The cap modification can be present at the 5'-terminus (5'-cap) or at the 3'-terminal (3'-cap), or can be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide: acyclic 3,5-dihydroxypentyl nucleotide, 3'-3'-inverted nucleotide moiety; 3'-3'-inverted abasic moiety; 3'-2'-inverted nucleotide moiety: 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In some embodiments, the 3'-cap is selected from a group comprising inverted deoxynucleotide, such as for example inverted deoxythymidine, 4',5'-methylene nucleotide: 1-(beta-D-erythrofuranosyl) nucleotide; 4'-thio nucleotide, carbocyclic nucleotide; 5'-amino-alkyl phosphate; 1,3-diamino-2-propyl phosphate: 3-aminopropyl phosphate; 6-aminohexyl phosphate; 1,2-aminododecyl phosphate; hydroxypropyl phosphate: 1,5-anhydrohexitol nucleotide: L-nucleotide; alpha-nucleotide; modified base nucleotide; phosphorodithioate; threo-pentofuranosyl nucleotide: acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety: 5'-phosphoramidate; 5'-phosphorothioate; 1,4-butanediol phosphate; 5'-amino; bridging and/or non-bridging 5'- to phosphoramidate, phosphorothioate and/or phosphorodithioate, bridging or non-bridging methylphosphonate and 5'-mercapto moieties (see generally Beaucage & Iyer, 1993; incorporated by reference herein).

A RNA silencing molecule (e.g. DNAzyme molecule) can be further modified by including a 3' cationic group, or by inverting the nucleoside at the terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

According to one embodiment, the 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the RNA silencing molecule (e.g. DNAzyme molecule) includes a modification that improves targeting. Examples of modifications that target RNA silencing molecule (e.g. DNAzymes) to particular cell types include carbohydrate sugars such as galactose. N-acetylgalactosamine, mannose; vitamins such as folates; other ligands such as RGDs and RGD mimics; and small molecules including naproxen, ibuprofen or other known protein-binding molecules (further discussed herein below).

According to one embodiment, the RNA silencing molecule (e.g. DNAzyme molecule) of the invention can be constructed using chemical synthesis and/or enzymatic ligation reactions using procedures known in the art (as discussed in detail below). For example, the polynucleotide can be chemically synthesized using naturally occurring nucleotides or variously modified nucleotides designed to increase the biological stability of the molecules or to increase the physical stability of the duplex formed between the polynucleotide and target nucleic acids. e.g., phosphorothioate derivatives and acridine substituted nucleotides can be used (as discussed in detail hereinabove).

The RNA silencing molecule (e.g. DNAzyme molecule) designed according to the teachings of the present invention can be generated according to any oligonucleotide synthesis method known in the art, including both enzymatic syntheses and solid-phase syntheses. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

According to one embodiment, chemical synthesis can be achieved by the diester method, triester method, polynucleotides phosphorylase method and by solid-phase chemistry. These methods are discussed in further detail below.

Diester Method: The diester method was the first to be developed to a usable state. The basic step is the joining of two suitably protected deoxynucleotides to form a dideoxynucleotide containing a phosphodiester bond.

Triester Method: The main difference between the diester and triester methods is the presence in the latter of an extra protecting group on the phosphate atoms of the reactants and products. The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method: This is an enzymatic method of DNA synthesis that can be used to synthesize many useful oligonucleotides. Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods: Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers. Equipment and reagents for executing solid-phase synthesis are commercially available from, for example, Applied Biosystems.

Phosphoramidite chemistry has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally to anchored at one end to a suitable solid support) to form the oligonucleotide product.

Recombinant Methods: Recombinant methods for producing nucleic acids in a cell are well known to those of skill in the art and can be implemented in cases where the RNA silencing molecule (e.g. DNAzyme molecule) does not comprise chemical modifications. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Maryland; Perbal, B. (1988), "A Practical Guide to Molecular Cloning," John Wiley & Sons, New York: and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

According to one embodiment, the RNA silencing molecule (e.g. DNAzyme molecule) is attached to a heterologous moiety that is selected to improve stability, increase half-life (e.g. in the serum or bronchalveolar lavage fluid (BALF)), distribution, cellular uptake, crossing of the blood brain barrier (BBB) or to target the RNA silencing molecule (e.g. DNAzyme molecule) to a cell of interest. Thus, the RNA silencing molecule (e.g. DNAzyme molecule) may be modified to include a non-nucleotide moiety, as discussed in detail below.

As used herein the phrase "heterologous moiety" refers to a sequence which does not form an intrinsic part of the RNA silencing molecule (e.g. DNAzyme molecule). Preferably, the heterologous moiety does not affect the biological activity of the RNA silencing molecule (e.g. DNAzyme), i.e. silencing activity, e.g. mediating catalytic activity on the p21 substrate.

According to one embodiment, the heterologous moiety is a proteinaceous moiety.

According to one embodiment, the heterologous moiety is a non-proteinaceous moiety.

According to one embodiment, the heterologous moiety is a cell-targeting moiety.

As used herein, the expression "cell-targeting moiety" refers to any substance that binds to a molecule expressed or presented on the target cell of interest, preferably in a specific manner, e.g. not expressed/presented on other cell types or expressed/presented at higher levels than in other cell types. According to a specific embodiment, the molecule expressed or presented on the target cell of interest is a polypeptide, e.g. receptor. This binding specificity allows the delivery of the RNA silencing molecule (e.g. DNAzyme molecule), which is attached to the cell-targeting moiety, to the cell, tissue or organ that expresses or presents the molecule (e.g. polypeptide, glycoprotein, receptor, ligand). In this way, a RNA silencing molecule (e.g. DNAzyme) attached to a cell-targeting moiety will be directed specifically to the target cells when administered to a subject (e.g. human) or contacted in vitro with a population of cells of different types.

The phrase "target cell" or "target cell of interest" refers to a cell that expresses a target RNA (e.g. p21 mRNA) and into which a RNA silencing molecule (e.g. DNAzyme molecule) is intended to be introduced. A target cell is, in some embodiments, a cell in a subject. According to a specific embodiment, the cell is a senescent cell. According to a specific embodiment, the cell is a cancerous cell.

The term "senescent cell" as used herein refers to a cell that exhibits cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes. The term senescent cell includes a cell which has entered senescence or is at the onset of senescence. i.e. a pre-senescent cell.

The term "cancerous cell" or "cancer cell" as used herein refers to cells associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within a subject (e.g. solid tumor), alternatively, cancer cells may circulate in the blood stream or in the lymphatic system as independent cells, for example, leukemic cells or lymphoma cells, respectively (e.g. non-solid tumor such as a hematologic malignancy), or may be dispersed throughout the body (e.g. metastasis).

A cell-targeting moiety according to the present invention may show a Kd for the target (the molecule expressed or presented on the target cell of interest, e.g. polypeptide. e.g. receptor, expressed on the senescent cell) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M or greater.

According to one embodiment, the cell-targeting moiety is a synthetic component.

According to one embodiment, the cell-targeting moiety is a nanoparticle capable of binding an antigen, a receptor or other protein, or non-proteinaceous membrane compounds of a target cell. A wide range of nanocarriers for nucleic acid drug delivery may be used in accordance with the present invention, including but not limited to, cationic polymers (for example, polyethylenimine), dendrimers, CPPs (for example, MPG-8, PepFect6. RVG-9R, and Xentry-KAL A), calcium phosphate nanoparticles, exosomes, and lipid nanoparticles (LNPs), as discussed in Roberts et al. *Nature Reviews Drug Discovery* (2020), incorporated herein by reference.

According to one embodiment, the cell-targeting moiety is a sugar (for example, N-acetylgalactosamine (GalNAc)).

According to one embodiment, the cell-targeting moiety is an affinity binding moiety. i.e. any naturally occurring or artificially produced molecule or composition which binds to a specific molecule (e.g. antigen) with a higher affinity than to a non-specific molecule (e.g. antigen).

It should be noted that the affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66) using e.g. a captured or immobilized monoclonal antibody (MAb) format to minimize contribution of avidity, and can be calculated using, e.g., a dissociation constant, Kd, such that a lower Kd reflects a higher affinity.

An affinity binding moiety typically has a binding affinity ($K_D$) of at least about 2 to about 200 M (i.e. as long as the binding is specific i.e., no background binding).

According to a specific embodiment, the affinity binding moiety is an aptamer or a lectin.

According to a specific embodiment, the affinity binding moiety is an antibody or an antibody fragment.

The term "antibody" as used in this invention includes intact molecules as well as functional fragments thereof, such as Fab, Fab', F(ab')2, Fv, linear antibodies, scFv antibodies, and multispecific antibodies formed from antibody fragments that are capable of binding to the antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule: (3) (Fab')2, the fragment of the antibody that can be obtained by treating whole antibody with the enzyme pepsin without subsequent reduction: F(ab')2 is a dimer of two Fab' fragments held together by two disulfide bonds: (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; (6) CDR peptide is a peptide coding for a single complementarity-determining region (CDR): and (7) Single domain antibodies (also called nanobodies), a genetically engineered single monomeric variable antibody domain which selectively binds to a specific antigen. Nanobodies have a molecular weight of only 12-15 kDa, which is much smaller than a common antibody (150-160 kDa).

According to one embodiment, the cell-targeting moiety binds to a senescent cell-specific cell surface polypeptide (e.g. marker of senescence with extracellular epitope/s). Exemplary senescent cell specific cell surface polypeptides include, but are not limited to, HSP90B1, DNAJB4, PI4K2A, DBN1, PRKCSH, SPTBN1. NPM1, ITGA3. CD58/ICAM1, ARMCX-3, B2MG, DCR2, DEP1, LANCL1, NOTCH3, PLD3, VPS26A, NTAL, EBP50, STX4, VAMP3, CD9, NOTCH1, OXIDIZED FORM OF MEMBRANE-BOUND VIMENTIN, TNFRSF10B, PLAUR, TSPAN2, ACTN1, ARL4C, OSBPL3, PHLDA3, THBS1, DPP4, REEP5, SQRDL, STOM, CAV1, SVIL, MGST1, WFS1, PTGS1, MBOAT7, PCYOX1, CNN1, F3, STIM1, SYNGR1, SLC6A15, THBD, TFPI2, NRG1, FLRT3, VAPB, SLC20A1, NTSR1, GPR68, ECSCR, NIM1, MCCC1, OSMR, TMEMI32A, TNC, PCCA, L1CAM, PCDH9, TGM2, ANPEP, CCT7, HK2.

According to one embodiment, the cell-targeting moiety binds to a cancer cell-specific cell surface polypeptide (e.g. tumor antigen). Exemplary tumor antigens include, but are not limited to, A33. BAGE, Bcl-2. B cell maturation antigen (BCMA), BCR-ABL, β-catenin, cancer testis antigens (CTA e.g. MAGE-1, MAGE-A2/A3 and NY-ESO-1). CA 125, CA 19-9, CA 50, CA 27.29(BR 27.29), CA 15-3, CD5, CDI 9, CD20, CD21, CD22, CD33, CD37, CD45, CD123, CEA, c-Met, CS-1, cyclin B1, DAGE, EBNA, EGFR, ELA2, ephrinB2, estrogen receptor, FAP, ferritin, folate-binding protein, GAGE, G250/CA IX, GD-2, GM2, gp75, gp100 (Pmel 17), HA-1, HA-2, HER-2/neu, HM1.24, HPV E6, HPV E7, hTERT, Ki-67, LRP, mesothelin, mucin-like cancer-associated antigen (MCA), MUC1, p53, PR1, PRAME, PRTN3, RHAMM (CD168), WT-1.

According to one embodiment, the RNA silencing molecule (e.g. DNAzyme molecule) of some embodiments of the invention comprises at least one cell-penetrating moiety.

As used herein the term "cell-penetrating moiety" refers to a compound which mediates transfer of a substance (e.g. RNA silencing molecule, e.g. DNAzyme) from an extracellular space to an intracellular compartment of a cell (e.g. senescent cell). Cell-penetrating moieties shuttle a linked substance (e.g., an RNA silencing molecule, e.g. a DNAzyme molecule) into the cytoplasm or to the cytoplasmic space of the cell membrane.

Cell-penetrating moieties include, without being limited to, lipidic moieties (i.e. naturally occurring or synthetically produced lipids) such as a cholesterol moiety (Letsinger et al, Proc. Natl. Acid. Sci. USA, 199, 86, 6553-6556), cholic acid (Manoharan et al, Biorg. Med. Chem. Let., 1994 4 1053-1060), a thioether, e.g., beryl-S-tritylthiol (Manoharan et al, Ann. N.Y. Acad. Sci., 1992, 660, 306-309; Manoharan et al, Biorg. Med. Chem. Let., 1993, 3, 2765-2770), a thiocholesterol (Oberhauser et al, Nucl. Acids Res., 1992, 20, 533-538), an aliphatic chain, e.g., dodecandiol or undecyl residues (Saison-Behmoaras et al, EMBO J, 1991, 10, 11 11-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al, Tetrahedron Lett., 1995, 36, 3651-3654; Shea et al, Nucl. Acids Res., 1990, 18, 3777-3783), a polyamine or a polyethylene glycol chain (Manoharan et al., Nucleosides and Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), an octa-decylamine or hexylamino-carbonyloxycholesterol moiety (Crooke et al., J. Pharmacol. Exp. Ther., 1996, 277, 923-937), a steroid, a sphingosine, a ceramide, or a fatty acid moiety. The fatty acid moiety can be, e.g., any fatty acid which contains at least eight carbons. For example, the fatty acid can be, e.g., a nonanoyl (C.sub.9); capryl (C.sub.10); undecanoyl (C.sub.11); lauroyl (C.sub.12); tridecanoyl (C.sub.13): myristoyl (C.sub.14); pentadecanoyl 0.30 (C.sub.15); palmitoyl (C.sub.16); phytanoyl (methyl substituted C.sub.16): heptadecanoyl (C.sub.17); stearoyl (C.sub.18); nonadecanoyl (C.sub.19); arachidoyl (C.sub.20): heniecosanoyl (C.sub.21); behenoyl (C.sub.22); trucisanoyl (C.sub.23); or a lignoceroyl (C.sub.24) moiety. The cell-penetrating moiety can also include multimers (e.g., a composition containing more than one unit) of octyl-glycine, 2-cyclohexylalanine, or benzolylphenylalanine. The cell-penetrating moiety contains an unsubstituted or a halogen-substituted (e.g., chloro) biphenyl moiety. Substituted biphenyls are associated with reduced accumulation in body tissues, as compared to compounds with a non-substituted biphenyl. Reduced accumulation in bodily tissues following administration to a subject is associated with decreased adverse side effects in the subject.

According to one embodiment, the cell-penetrating moiety is a peptide (CPP). Suitable peptides typically include short (typically less than 30 amino acids) amphipathic or cationic peptide fragments that are typically derived from naturally occurring protein translocation motifs, as in the case of HIV-TAT (transactivator of transcription protein). Penetratin 1 (homeodomain of the *Drosophila* Antennapedia protein) and Transportan (a chimeric peptide consisting of part of the galanin neuropeptide fused to the wasp venom, mastoparan), or are based on polymers of basic amino acids (e.g. arginine and lysine). Additional examples are provided in Roberts et al. *Nature Reviews Drug Discovery* (2020), incorporated herein by reference.

It will be appreciated that the cell-targeting moiety may be used for cell penetration and likewise the cell-penetrating moiety may be used for cell targeting. Thus, it is to be understood that the moieties discussed herein above may be used interchangeably.

The RNA silencing molecule (e.g. DNAzyme molecule) and the heterologous moiety (e.g. cell-targeting moiety or the cell-penetrating moiety) may be coupled directly or indirectly via an intervening moiety or moieties, such as a linker, a bridge, or a spacer moiety or moieties.

According to one embodiment, the RNA silencing molecule (e.g. DNAzyme molecule) and the heterologous moiety (e.g. cell-targeting moiety or the cell-penetrating moiety) may be directly coupled. Alternatively, according to another embodiment, the moiety may be linked by a connecting group. The terms "connecting group", "linker". "linking group" and grammatical equivalents thereof are used herein to refer to an organic moiety that connects two parts of a compound.

The heterologous moiety (e.g. cell-targeting moiety or the cell-penetrating moiety) can be attached to any nucleotide in the RNA silencing molecule (e.g. DNAzyme molecule), but it can be preferably coupled through the 3' terminal nucleotide and/or 5' terminal nucleotide. An internal conjugate may be attached directly or indirectly through a linker to a nucleotide at a 2' position of the ribose group, or to another suitable position.

Thus, the heterologous moiety (e.g. cell-targeting moiety or the cell-penetrating moiety) can be attached to any nucleotide within the RNA silencing molecule (e.g. DNAzyme molecule) as long as the silencing activity (e.g.

mediating catalytic activity) of the RNA silencing molecule (e.g. DNAzyme) is not compromised.

Any of the above described moieties (e.g. cell-targeting moiety or the cell-penetrating moiety) may be selected by the skilled person taking into consideration the target tissue, the target cell, the administration route, the pathway that the RNA silencing molecule (e.g. DNAzyme) is expected to follow, etc.

According to one embodiment, when the moiety (e.g. cell-targeting moiety or the cell-penetrating moiety) is a peptide or peptide product, it may be subjected to in-vitro modification (e.g., PEGylation, lipid modification, etc.) so as to confer the peptide's amino acid sequence with stability (e.g., against protease activities) and/or solubility (e.g., within a biological fluid such as blood, digestive fluid) while preserving its biological activity and prolonging its half-life.

When the RNA silencing molecule (e.g. DNAzyme molecule) is coupled to a heterologous moiety, synthesis can be carried out using standard procedures in organic synthesis. The skilled person will appreciate that the exact steps of the synthesis will depend on the exact structure of the molecule which has to be synthesized. For instance, if the molecule is attached to the heterologous moiety through its 5' end, then the synthesis is usually carried out by contacting an amino-activated oligonucleotide and a reactive activated heterologous moiety.

According to one embodiment, the RNA silencing molecule (e.g. DNAzyme) is coupled to a heterologous moiety and to a protecting group (e.g. the heterologous moiety is coupled to the 5' end of the RNA silencing molecule, e.g. DNAzyme, and the protecting group to the 3' end, or vice versa).

According to one embodiment, there is provided a method of eradicating a senescent cell or a cancer cell with the composition of matter of some embodiments of the invention.

The RNA silencing molecule (e.g. DNAzyme molecules) of the invention are to be provided to the cells i.e., target cells (e.g. senescent cells or cancer cells) of the present invention in vivo (i.e., inside the organism or the subject), in vitro or ex vivo (e.g., in a tissue culture). It will be appreciated that the RNA silencing molecule may be provided directly to the target cells, or alternatively may be administered to a tissue or organ comprising the target cells, or to a subject in need of eradication of senescent cells or cancer cells.

The prior art teaches of a number of delivery strategies which can be used to efficiently deliver oligonucleotides into a wide variety of cell types [see, for example, Jääskelainen et al. *Cell Mol Biol Lett*. (2002) 7(2):236-7; Gait, *Cell Mol Life Sci*. (2003) 60(5):844-53: Martino et al. *J Biomed Biotechnol*. (2009) 2009:410260: Grijalvo et al. *Expert Opin Ther Pat*. (2014) 24(7):801-19: Falzarano et al, *Nucleic Acid Ther*. (2014) 24(1):87-100: Shilakari et al. *Biomed Res Int*. (2014) 2014: 526391, Prakash et al. *Nucleic Acids Res*. (2014) 42(13):8796-807 and Asseline et al. *J Gene Med*. (2014) 16(7-8):157-65].

According to one embodiment, the present techniques relate to introducing the RNA silencing molecules using transient DNA or DNA-free methods (such as RNA transfection).

According to one embodiment, the RNA silencing molecule (e.g. DNAzyme, antisense molecule) is delivered as a "naked" oligonucleotide, i.e. without the additional delivery vehicle. According to one embodiment, the "naked" oligonucleotide comprises a chemical modification to facilitate its tissue delivery (e.g. utilizing inverted nucleotides, phosphorothioate linkages, or integration of locked nucleic acids, as discussed above).

Any method known in the art for RNA or DNA transfection can be used in accordance with the present teachings, such as, but not limited to microinjection, electroporation, lipid-mediated transfection e.g. using liposomes, or using cationic molecules or nanomaterials (discussed below, and further discussed in Roberts et al. *Nature Reviews Drug Discovery* (2020) 19: 673-694, incorporated herein by reference).

According to one embodiment, and as mentioned above, in cases where the RNA silencing molecule (e.g. DNAzyme molecule) does not comprise a chemical modification it may be administered to the target cell (e.g. senescent cell) as part of an expression construct. In this case, the RNA silencing molecule (e.g. DNAzyme molecule) is ligated in a nucleic acid construct (also referred to herein as an "expression vector") under the control of a cis-acting regulatory element (e.g. promoter) capable of directing an expression of the RNA silencing molecule (e.g. DNAzyme) in the target cells (e.g. senescent cell) in a constitutive or inducible manner.

The expression constructs of the present invention may also include additional sequences which render it suitable for replication and integration in eukaryotes (e.g., shuttle vectors). Typical cloning vectors contain transcription and translation initiation sequences (e.g., promoters, enhances) and transcription and translation terminators (e.g., polyadenylation signals). The expression constructs of the present invention can further include an enhancer, which can be adjacent or distant to the promoter sequence and can function in up regulating the transcription therefrom. Polyadenylation sequences can also be added to the expression constructs of the present invention in order to increase the efficiency of expression.

In addition to the embodiments already described, the expression constructs of the present invention may typically contain other specialized elements intended to increase the level of expression of cloned nucleic acids or to facilitate the identification of cells that carry the RNA silencing molecule (e.g. DNAzyme). The expression constructs of the present invention may or may not include a eukaryotic replicon.

The nucleic acid construct may be introduced into the target cells (e.g. senescent cells or cancer cells) of the present invention using an appropriate gene delivery vehicle/method (transfection, transduction, etc.) and an appropriate expression system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464, 764 and 5,487,992 for positive-negative selection methods.

Additionally or alternatively, lipid-based systems may be used for the delivery of constructs or RNA silencing molecule (e.g. DNAzyme molecules) into the target cells (e.g. senescent cells or cancer cells) of the present invention. Lipid bases systems include, for example, liposomes, lipoplexes and lipid nanoparticles (LNPs).

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M. Lasic D D, Chem Phys Lipids, 1993 September: 64(1-3):35-43]. Any method known in the art can be used to incorporate a polynucleotide agent (e.g. RNA silencing molecule, e.g. DNAzyme molecule) into a liposome. For example, the polynucleotide agent (e.g. RNA silencing molecule, e.g. DNAzyme molecule) may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa 19$^{th}$ ed., (1995)] and those described by Kulkami et al., [J. Microencapsul. 1995, 12 (3) 229-46].

Furthermore, lipid nanoparticles (LNPs), also known as stable nucleic acid lipid particles, may be used in accordance with the present teachings. These are typically liposomes that contain ionizable lipid, phosphatidylcholine, cholesterol and PEG-lipid conjugates, as discussed in Roberts et al. *Nature Reviews Drug Discovery* (2020), incorporated herein by reference.

The lipid bases systems (e.g. liposomes) used in the methods of the present invention may cross the blood barriers. Thus, according to an embodiment the lipid bases systems (e.g. liposomes) of the present invention do not comprise a blood barrier targeting polysaccharide (e.g. mannose) in their membrane portion. In order to determine lipid bases systems (e.g. liposomes) that are especially suitable in accordance with the present invention a screening assay can be performed such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804.

For in vivo therapy, the composition of matter of some embodiments of the invention comprising a RNA silencing molecule (e.g. DNAzyme molecule) is administered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the RNA silencing molecule (e.g. DNAzyme molecule) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include systemic, oral, rectal, transmucosal, especially transnasal, intestinal or parenteral delivery, including intramuscular, subcutaneous and intramedullary injections as well as intrathecal, direct intraventricular, intracardiac. e.g., into the right or left ventricular cavity, into the common coronary artery, intravenous, intraperitoneal, intranasal, intratumoral or intraocular injections.

According to a specific embodiment, the composition is for pulmonary route of administration.

According to a specific embodiment, the composition is for inhalation mode of administration. Exemplary inhalers which can be used in accordance with some embodiments of the invention include pressurized metered-dose inhalers (pMDIs), breath-actuated metered dose inhalers (bMDIs), dry powder inhalers (DPIs, single or multidose), and soft mist inhalers.

According to a specific embodiment, the composition is for intranasal administration.

According to a specific embodiment, the composition is for intracerebroventricular administration.

According to a specific embodiment, the composition is for intrathecal administration.

According to a specific embodiment, the composition is for intratumoral administration.

According to a specific embodiment, the composition is for oral administration.

According to a specific embodiment, the composition is for local injection.

According to a specific embodiment, the composition is for systemic administration.

According to a specific embodiment, the composition is for intravenous administration.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose: and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form. e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the present invention include compositions wherein the active ingredients are contained in an amount effective to achieve the intended purpose. More specifically, a therapeutically effective amount means an amount of active ingredients (e.g. RNA silencing molecule, e.g. DNAzyme molecule) effective to prevent, alleviate or ameliorate symptoms of a disorder (e.g., senescent cell-related condition or cancer) or prolong the survival of the subject being treated.

According to an embodiment of the present invention, administration of the RNA silencing molecule (e.g. DNAzyme molecule) has a senolytic effect (i.e. induces death of a senescent cell).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that animal models exist by which the RNA silencing molecule (e.g. DNAzyme molecules) of the present invention may be tested prior to human treatment. For example, animal models for testing senolytic agents include mice with pulmonary fibrosis induced by solubilized bleomycin, and guinea pigs developing a condition similar to human osteoarthritis, as discussed in Kirkland and Tchkonia, *Exp Gerontol*. (2015) 68: 19-25, incorporated herein by reference. Furthermore, animal models for testing anti-cancer drugs are well known in the art and are discussed in Chavan, *International Journal of Pharmaceutical Sciences and Research* (2013) 4(1):19-28, incorporated herein by reference.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, there is provided an article of manufacture comprising the composition of matter of some embodiments of the invention, being packaged in a packaging material and identified in print, in or on the packaging material for use in the treatment of senescence-associated disease or disorder, a cancer or a fibrotic disease or disorder.

It will be appreciated that the therapeutic compositions of the invention may comprise, in addition to the RNA silencing molecule (e.g. DNAzyme molecule), other known medications for the treatment of senescence, e.g. senolytic agents (e.g., senolytic drugs). Exemplary senolytic agents which can be used in accordance with some embodiments of the invention include, but are not limited to, Dasatinib, Quercetin, Piperlongumine, Tocotrienols, Navitoclax, Bcl2-family inhibitors such as ABT-263 and ABT-737, PF-573228, JFD00244, Ouabain, Bufalin, Digoxin. K-Strophanthin, Strophanthidin, Cyclosporine, Tyrphostin AG879, Cantharidin, Diphenyleneiodonium chloride, Rottlerin, 2,3-Dimethow-1,4-naphthoquinone, LY-367,265, Rotenone, Idarubicin, Dequalinium chloride, Vincristine, Atorvastatin calcium, Fluvastatin sodium, Lovastatin, Pitavastatin calcium, Simvastatin, Nitazoxanide, Nitrofurazone, Temsirolimus, Eltrombopag, Adapalene, Azacyclonol, Enoxacin, Raltegravir, NSC 677249, Defactinib and HSP90 inhibitors (e.g. 17-DMAG and 17-AAG) (as discussed in U.S. Patent Application No. 2020/0121620, incorporated herein by reference).

It will be appreciated that the therapeutic compositions of the invention may comprise, in addition to the RNA silencing molecule (e.g. DNAzyme molecule), chemotherapeutic agents which may be affected concomitantly or separately to eliminate cancer cells such as those which have been pushed to senescence, and/or to eliminate or reduce certain side effects produced by senescent cells such as inflammation, promotion of cancer growth, promotion of metastasis and other side effects of chemotherapy, and/or to reduce or eliminate precancerous lesions. Non-limiting examples of chemotherapeutic agents include, but are not limited to, platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, idarubicin, actinomycin, bleomycin, mitonmcin, mitoxantrone, plicamycin, etc.), anti-angiogenic agents (e.g. thalidomide or pomalidomide, e.g. Pomalyst and Imnovid), and other agents such as Palbociclib (e.g. Ibrance®), Lenalidomide (e.g. Revlimid®) or Lurbinectedin (e.g. Zepzelca®), and combinations thereof.

Additionally or alternatively, the therapeutic compositions of the invention may comprise, in addition to the RNA silencing molecule (e.g. DNAzyme molecule), biological therapy e.g., immunotherapy (e.g. antibody immunotherapy), cytokines/chemokines, hormonal therapy, which may be affected concomitantly or separately to eliminate senescence cells, cancer cells and/or to eliminate or reduce certain side effects produced by senescent cells such as inflammation, promotion of cancer growth, promotion of metastasis and other side effects of chemotherapy, and/or to reduce or eliminate precancerous lesions.

Any of the above described compositions may be packed together or separately (e.g. in a single container or in separate containers): e.g., RNA silencing molecule (e.g. DNAzyme) packed separately from the chemotherapeutic agent or senolytic agent; or RNA silencing molecule (e.g. DNAzyme) and the chemotherapeutic agent or senolytic agent in a single container.

According to another aspect of the present invention, there is provided a method of treating a senescence-associated disease or disorder in a subject in need thereof, the method comprising administering to the subject a therapeutically effective amount of the composition of matter of some embodiments of the invention, thereby treating the senescence-associated disease or disorder.

According to another aspect of the present invention, there is provided a therapeutically effective amount of the composition of matter of some embodiments of the invention for use in treating a senescence-associated disease or disorder in a subject in need thereof.

According to another aspect of the present invention, there is provided a method of treating a cancer in a subject in need thereof, the method comprising administering to the subject a therapeutically effective amount of the composition of matter of some embodiments of the invention, thereby treating the cancer.

According to another aspect of the present invention, there is provided a therapeutically effective amount of the composition of matter of some embodiments of the invention for use in treating cancer in a subject in need thereof.

According to another aspect of the present invention, there is provided a method of treating a fibrotic disease or disorder in a subject in need thereof, the method comprising administering to the subject a therapeutically effective amount of the composition of matter of some embodiments of the invention, thereby treating the fibrotic disease or disorder.

According to another aspect of the present invention, there is provided a therapeutically effective amount of the composition of matter of some embodiments of the invention for use in treating a fibrotic disease or disorder in a subject in need thereof.

The term "treating" refers to inhibiting, preventing or arresting the development of a pathology (disease, disorder or condition) and/or causing the reduction, remission, or regression of the pathology. Those of skill in the art will understand that various methodologies and assays can be used to assess the development of a pathology, and similarly, various methodologies and assays may be used to assess the reduction, remission or regression of a pathology.

As used herein, the term "subject" or "subject in need thereof" includes mammals, such as human beings, male or female, at any age which suffers from the pathology or is at risk to develop the pathology.

The term "senescence-associated disease or disorder" refers to any disease or condition in which senescent cells are involved in the pathogenesis of the disease, resistance to treatment, or side effects associated with a disease.

Exemplary senescence-associated disease or disorder include, but are not limited to, inflammatory or autoimmune diseases or disorders (e.g. osteoarthritis (OA), osteoporosis, oral mucositis, inflammatory bowel disease, kyphosis and herniated intervertebral disc), neurological diseases or disorders (e.g. Alzheimers disease, Parkinson's disease, Huntington's disease, dementia, ataxia, mild cognitive impairment, macular degeneration and motor neuron dysfunction, e.g. amyotrophic lateral sclerosis (ALS)), metabolic diseases or disorder (e.g. diabetes, diabetic ulcer, metabolic syndrome, non-alcoholic fatty liver disease (NAFLD) and obesity), pulmonary diseases or disorder (e.g. chronic obstructive pulmonary disease (COPD), idiopathic pulmonary fibrosis (IPF), pulmonary fibrosis, chronic obstructive pulmonary disease, asthma, cystic fibrosis, emphysema, bronchiectasis, hyperoxic lung damage, and age-related loss of pulmonary function), eye diseases or disorders (e.g. macular degeneration, glaucoma, cataracts, presbyopia and vision loss), age-related diseases or disorders (e.g. renal disease, renal failure, frailty, hearing loss, muscle fatigue, age-related muscle loss, skin conditions, skin wound healing, liver fibrosis, pancreatic fibrosis, oral submucosa fibrosis, sarcopenia, age-related intervertebral disc disease, and age-related cognitive dysfunction), renal diseases or disorders (e.g. renal dysfunction, urinary incontinence), hepatic diseases or disorders (e.g. hepatic steatosis, cirrhosis, primary biliary cirrhosis, idiopathic non-alcoholic steatohepatitis (NASH)), dermatological diseases or disorders (e.g. eczema, psoriasis, hyperpigmentation, nevi, rashes, atopic dermatitis, urticaria, diseases and disorders related to photosensitivity or photoaging, rhytides, pruritis, dysesthesia, eczematous eruptions, eosinophilic dermatosis, reactive neutrophilic dermatosis, pemphigus, pemphigoid, immunobullous dermatosis, fibrohistocytic proliferations of skin, cutaneous lymphomas and cutaneous lupus), cardiac disease or disorder (e.g. cardiac dysfunction), vascular disease or disorder (e.g. vascular hyporeactivity/calcification, arteriovenous (AV) fistula), cardiovascular diseases or disorders (e.g. atherosclerosis) or other diseases or disorders such as pre-eclampsia, progeria, obesity-related neuropsychiatric dysfunction or prostatic hypertrophy.

According to a specific embodiment, the cell senescence is associated with drug-induced senescence (e.g. chemotherapy, e.g. chemotherapy complications).

According to a specific embodiment, the cell senescence is associated with irradiation-induced senescence (e.g. irradiation therapy, e.g. radiation complications).

According to a specific embodiment, the cell senescence is associated with transplantation of a cell, tissue or organ (e.g. bone marrow transplant or solid-organ transplant, e.g. transplant related complications such as graft rejection or graft versus host disease).

According to a specific embodiment, the cell senescence is associated with chronic wounds, such as non-healing chronic wounds.

According to a specific embodiment, the cell senescence is associated with environmental factors (e.g. smoking e.g. tobacco, radiation, pollution).

According to a specific embodiment, the cell senescence is associated with healthspan and/or lifespan.

Those of skill in the art will understand that various methodologies and assays can be used to assess the efficiency of treatment, for example, by detecting the levels of senescent cells in biological samples (e.g. blood, serum, cerebrospinal fluid (CSF), tissue sample) by using senescence associated markers such as, senescence-associated β-galactosidase, p16INK4a, p21, PAI-1, or one or more senescence associated secretory phenotype (SASP) factors (IL-8, IL-1alpha, IL-1beta, IL-6, MMP10, MCP1, CXCL1, MMP1, STC1, GDF15, MMP9, CCL5. TNF, TGF-beta, SERPINE1), or by assessing the levels of senescent cell biomarkers including, e.g. DEP1, NTAL, EBP50, STX4, VAMP3, ARMCX-3, LANCL1, B2MG, PLD3 and VPS26A, using well known methodologies (e.g. RT-PCR, FACS, ELISA, or immunostaining).

According to one embodiment, an efficient senolytic treatment is determined when there is a decrease of at least about 10%, 20%, 30%, 40%, 50%, 60%, 70%, 80%, 90% or 100% or more in the number of senescent cells, as compared to the number of senescent cells in the subject being treated but prior to the treatment.

According to a specific embodiment, the disease is a fibrotic disease or disorder.

The term "fibrotic disease or disorder", also referred to as "fibrosis" or "fibro proliferative disease", as used herein refers to the formation of excess fibrous connective tissue in a reparative process upon injury or damage. Scarring is a result of continuous fibrosis that obliterates the affected organs or tissues architecture. As a result of abnormal reparative processes, which do not clear the formed scar tissue, fibrosis progresses further. Fibrosis can be found in various tissues, including the heart, the lungs, the liver, the skin, blood vessels and the kidneys.

An individual may be identified as having fibrosis by determining if a subject has organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP) and decreased levels of C-terminal telopeptide of Type I Collagen (CTP or CITP), increased collagen deposition and impaired cardiac function measured by various noninvasive imaging techniques, impaired renal function measured by increased proteinurea and albuminurea, decreased glomerular filtration rate, doubling of plasma creatinine levels.

Exemplary fibrotic diseases include, but are not limited to, pulmonary fibrosis, (e.g. idiopathic pulmonary fibrosis (IPF), sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapours, radiation-induced lung fibrosis, drug-induced lung fibrosis, e.g. drug-induced interstitial lung disease, autoimmune lung fibrosis (also referred to as connective tissue disease-related) or pulmonary hypertension), liver fibrosis (e.g., liver fibrosis resulting from a chronic liver disease, hepatitis B virus infection, hepatitis C virus infection, hepatitis D virus infection, schistosomiasis, alcoholic liver disease or non-alcoholic steatohepatitis, non-alcoholic fatty liver disease, obesity, diabetes, protein malnutrition, coronary artery disease, auto-immune hepatitis, cystic fibrosis, alpha-1-antitrypsin deficiency, liver cirrhosis, primary biliary cirrhosis, drug reaction and exposure to toxins, or bridging fibrosis), kidney fibrosis (e.g. progressive kidney disease, chronic kidney disease), pancreatic fibrosis, cardiac fibrosis (e.g. associated with various cardiovascular diseases, myocardial fibrosis, endomyocardial fibrosis), scleroderma or systemic sclerosis, oral submucosa fibrosis, intestinal fibrosis (e.g. Crohn's disease), eosinophilic esophagitis, hypereosinophilic syndromes (HES), Loeffler's endomyocarditis or skin fibrosis (e.g. scarring, hypertrophic scarring, keloid scarring, dermal fibrotic disorder, psoriasis or scleroderma. Scarring may be derived from a burn, a trauma, a surgical injury, a radiation or an ulcer. The ulcer can be a diabetic foot ulcer, a venous leg ulcer or a pressure ulcer).

According to a specific embodiment, the fibrosis is pulmonary fibrosis. Pulmonary fibrosis can result from different factors including, for example, drugs (e.g. amiodarone, nitrofurantoin, chemotherapy, methotrexate, or other drugs known to affect the lungs), radiation (e.g. prior or current radiation treatment to the chest), environmental factors (e.g. exposure to mold, animals), and occupational factors (e.g. exposure to dusts, fibers, fumes, or vapors such as asbestos, coal and silica). Lung fibrosis can also be autoimmune related (e.g. associated with joint inflammation) or idiopathic.

According to one embodiment, the fibrosis is organ fibrosis related to tissue injury including, but not limited to, fibrosis associated with cardiovascular disease, fibrosis associated with pulmonary disease, fibrosis associated with a kidney disease, and fibrosis that has occurred following an organ transplant, such as a kidney, lung, heart or liver transplant.

According to one embodiment, the fibrosis is associated with a chronic damage or injury.

According to one embodiment, an efficient anti-fibrotic treatment is determined when there is a decrease of at least about 10%, 20%, 30%, 40%, 50%, 60%, 70%, 80%, 90% or 100% or more in the number of fibrotic cells, or in the fibrotic tissue mass, as compared to the number of fibrotic cells, or fibrotic tissue mass, in the subject being treated but prior to the treatment.

Those of skill in the art will understand that various methodologies and assays can be used to assess the efficiency of anti-fibrotic treatment, e.g. imaging and blood tests (as discussed above).

According to one embodiment, the senescence-associated disease or disorder is associated with a cancerous disease.

According to one embodiment, the senescence-associated disease or disorder comprises an inflammation, precancerous lesions, promotion of cancer growth and/or of metastasis.

According to one embodiment, the cancer is therapy-resistant cancer (e.g. resistant to chemotherapy, radiation therapy, phototherapy/photodynamic therapy, or a combination thereof).

According to a specific embodiment, the cell senescence is associated with oncogene-induced senescence.

According to one embodiment, the cancer is not associated with cell senescence.

Types of cancerous diseases amenable to treatment by the methods of some embodiments of the invention include benign tumors, warts, polyps, pre-cancers, malignant tumors/cancers and cancer metastasis.

Examples of cancer include but are not limited to, carcinoma, blastoma, sarcoma and lymphoma. More particular examples of such cancers include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma. Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma. B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia. B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, monoclonal gammopathy of undetermined significance (MGUS), nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome 11, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to a specific embodiment, the cancer is lung cancer.

According to one embodiment, treating a cancerous disease may be further effected by administering to the subject an additional medicament (or any combination of medicaments) for the treatment of the cancerous disease. Such medicaments may include, without being limited to, radiation therapy, chemotherapy, biological therapy. e.g., immunotherapy (e.g. antibody immunotherapy), phototherapy/photodynamic therapy, surgery, nutritional therapy, or combinations thereof. Such medicaments may be affected prior to, concomitantly with, or following the RNA silencing molecule (e.g. DNAzyme molecules) of some embodiments of the invention.

It will be appreciated that the use of the RNA silencing molecules (e.g. DNAzyme molecules) of some embodiments of the invention can reduce the amount of chemotherapy administered to a subject needed to achieve a therapeutic effect (i.e. elimination of cancer cells). Such a therapy is specifically beneficial in order to reduce harm to healthy cells.

According to one embodiment, an efficient anti-cancer treatment is determined when there is a decrease of at least about 10%, 20%, 30%, 40%, 50%, 60%, 70%, 80%, 90% or 100% or more in tumor mass or there is a halt in tumor growth, as compared to a subject not treated by the composition of the invention, or compared to the same subject being treated but prior to the treatment.

Those of skill in the art will understand that various methodologies and assays can be used to assess the efficiency of cancer treatment, e.g. CT scan, MRI, X-ray, ultrasound, blood tests etc.

According to one embodiment the RNA silencing molecules (e.g. DNAzyme molecules) of some embodiments of the invention may be administered to the subject as a single RNA silencing molecule (e.g. DNAzyme molecule) treatment. Alternatively, the RNA silencing molecules (e.g. DNAzyme molecules) of some embodiments of the invention may be administered to the subject in combination (e.g. 2, 3, 4, 5 or more RNA silencing molecules) in order to mediate cleavage of two or more target sites in p21 mRNA thereby increasing efficiency of RNA silencing. Such a determination is well within the capability of one of skill in the art.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to an p21 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York: Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes 1-III Cellis, J. E., ed. (1994): "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980): available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219: 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986): "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996): all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Cell Culture

Human IMR-90 fibroblasts were obtained from ATCC and grown at 5% oxygen. Cells were maintained in DMEM medium comprising 100 units per ml of penicillin, 100 mg/ml of streptomycin and 10% fetal bovine serum, mLFs were isolated according to standard procedures [Seluanov, A., et al. *J Vis Exp* (2010) (44):2033] and grown at 5% oxygen. Cells were maintained in EMEM medium comprising 100 units per ml of penicillin, 100 mg/ml of streptomycin and 15% fetal bovine serum. DNA damage induces senescence (DIS) was introduced by etoposide treatment (E1383, Sigma) at a concentration of 50 μM for IMR-90 and 16 μM for mLF, for 48 hours. Cells acquired the senescence phenotype 7 days post treatment.

Human BJ fibroblasts were obtained from ATCC and grown at 5% oxygen. The cells were maintained in EMEM medium comprising 100 units per ml of penicillin, 100 mg/ml of streptomycin, 10% fetal bovine serum. 1% Pyruvate, 1% L-Glutamine. DNA damage induced senescence (DIS) was induced by etoposide treatment (Sigma) at a concentration of 100 μM for a duration of 48 hours. Cells acquired the senescence phenotype 7 days post treatment.

Design of DNAzymes, siRNA and Antisense Oligonucleotides

DNAzymes, a double-stranded siRNA and antisense oligonucleotides were designed for the selected mRNA targets and were ordered from Integrated DNA Technologies Syntezza, USA. Control DNAzymes with scrambled arms were designed using an online software tool (GenScript®). A commercial p21-targeting siRNA was purchased (Dharmacon).

Viability Assay

Senescent human IMR-90 fibroblasts were plated in 24-well plates at 100,000 cells per well. Cells were transfected with 500 nM DNAzymes (as depicted in Tables 3A-B, below). The percentage of survival was determined based on quantification of remaining adherent cells using PrestoBlue® reagent (A13262, Life Technologies Ltd.) relative to control DNZ_Scramble (sequence. ATCTTCCTTggctagctacaacgaCGCCTCTCC, SEQ ID NO: 3) treated cells, 3-6 days following transfection.

Senescent BJ cells were plated in 24-well plates at 90,000 cells per well. Cells were transfected with different concentrations of DNAzymes, ASOs and siRNAs (as depicted in Tables 4 and 5, below) using Lipofectamine™ 2000 (11668-019, Invitrogen) according to manufacturer instructions. ASO and DNAzymes were used at a concentration of 1000 nM, and siRNAs were used at a concentration of 25 nM. Percentage of survival was determined based on quantification of remaining adherent cells using PrestoBlue® reagent (A13262, Life Technologies Ltd.) relative to control cells treated only with Lipofectamine™ 2000, 5 days following transfection.

mRNA Target Preparation

Total RNA was isolates from senescent IMR-90 cells using Nucleospin™ RNA kit (Macherey-Nagel™). cDNA was synthesized with gene-specific reverse primers using M-MLV Reverse Transcriptase (Promega), according to the manufacturer's protocol. To generate template for in vitro transcription (IVT) reaction, the cDNA was PCR amplified using KAPA Taq EXtra HotStart® ReadyMix PCR Kit (R&D). PCR product was run on 1.5% agarose TAEFgel, the correct band size was cut and DNA was cleaned using Wizardt SV Gel and PCR Clean-Up System kit (Promega). IVT was performed using HiScribe™ T7 High Yield RNA Synthesis Kit (NEB). Samples were then treated with DNase I (New England Biolabs) and incubated for 15 minutes at 37° C. WT product was run on 1.5% agarose TBE gel, the correct band size was cut and RNA was cleaned using QIAquick Gel Extraction Kit (Qiagen).

Total RNA was isolated from senescent BJ cells using Nucleospin™ RNA kit (Macherey-Nagel™, 740955.50). Complementary DNA was prepared using the M-MLV Reverse Transcriptase (Promega, M 1701), according to the manufacturer protocol. Quantitative real-time PCR was performed using the SYBR™ Green PCR master-mix (Applied Biosystems, 4309155) on a CFX96 Real-Time PCR System (Bio Rad).

TABLE 1

Primer list

| | | | |
|---|---|---|---|
| Human | T7 CDKN1A FORWARD | TAATACGACTCACTATAGATGTTGAGCTCTGGC ATAGAAGAGGCTGGTGGCTATTTTGTCCTTGG GCTGCCTGTTTTCAG (SEQ ID NO: 124) | CDNA + PCR |
| Human | CDKN1A REVERSE | TAAAGTCACTAAGAATCATTTATTGAGCACCT GCTGTATATTCAGCATTGTGGGAGGAGCTGTG AAAGACACAGAACAGT (SEQ ID NO: 125) | PCR |
| Mouse | cdkn1a_ REVERSE | AATCATCGAGAAGTATTTATTGAGCACCAGCT TTGGGGTCGGGTGTGAGGACTCGGGACAATGC AGG (SEQ ID NO: 126) | CDNA + PCR |
| Mouse | T7_cdkn1a_ FORWARD | TAATACGACTCACTATAGTGCAGCAGCCGAGA GGTGTGAGCCGCC (SEQ ID NO: 127) | PCR |
| Human | GAPDH Forward | TGGTATCGTGGAAGGACTCA (SEQ ID NO: 135) | RT-PCR |
| Human | GAPDH Reverse | CCAGTAGAGGCAGGGATGAT (SEQ ID NO: 136) | RT-PCR |
| Human | HPRT Forward | CCCTGGCGTCGTGATTAGTG (SEQ ID NO: 137) | RT-PCR |
| Human | HPRT Reverse | TCGAGCAAGACGTTCAGTCC (SEQ ID NO: 138) | RT-PCR |
| Human | On-site 1668 Forward | GCCCGTCTCAGTGTTGAGC (SEQ ID NO: 139) | RT-PCR |
| Human | On-site 1668 Reverse | GGAGCTGAGAGGGTACTGAAG (SEQ ID NO: 140) | RT-PCR |

In Vitro Cleavage Assay

RNA substrate was diluted with Molecular Biology Grade Water (Biological Industries) and used in in vitro cleavage assay. A 20 µl reaction system comprising RNA substrate (final concentration 500 nM), 2 µl 10× reaction buffer (50 mM Tris-HCl pH 7.4, 100 mM NaCl, 10 mM MgCl$_2$) and 1 µl DNAzyme (10 µM) (as depicted in Tables 3A-B, below) was mixed. Reactions were incubated at 37° C. for 60 min. 2×RNA L.D. (Thermo Fisher) was added to each sample. Samples were heated at 70° C. for 30 sec, centrifuged and loaded onto 1.5% agarose TBE gels.

Example 1

Targeting DNAzymes to p21 Hot Areas

A proprietary algorithm was developed to calculate the secondary and tertiary structure of an mRNA sequence target, determine which mRNA regions are hot areas for DNAzyme attack, and for design of optimal DNAzymes to cleave it. The human mRNA sequence for p21, set forth in SEQ ID NO: 1, is provided in FIG. 3. An algorithm-generated map of the p21 mRNA based on its structure was used to assign a score to regions on the mRNA that indicated their accessibility to a molecule of the size and structure of DNAzymes (FIG. 4). This map was used to generate a table of optimal potential cleavage areas (referred to as "hot spot areas" or "hot areas"—HA) for DNAzymes and designated these as p21HAs (Table 2, below). The table depicts ten hot areas from the highest to the lowest score. DNAzymes targeting hot areas and those targeting areas outside of the hot areas were designed, such as hot area 09 (Tables 3A-B, below), the DNAzyme number depicting the cleavage site position on the p21 mRNA as set forth in SEQ ID NO: 1. DNAzymes targeting these areas were more efficient than those targeting other areas as illustrated in FIGS. 5A-B. DNAzymes designed to cleave p21 mRNA in regions that are outside the hot areas, showed minimal, if any, cleavage (FIG. 5A). The cleavage by DNAzymes could be controlled by the dosage and incubation time as shown (FIG. 5B). This highlighted the potential benefit of DNAzyme treatments that can be dose optimized to obtain a maximal effect while controlling potential adverse effects.

TABLE 3A

DNAzyme sequences targeting areas at or surrounding HA09

| DNAzyme name | Sequence | SEQ ID NO |
|---|---|---|
| Scr A | ATCTTCCTTggctagctacaacgaCGCCTCTCC | 13 |
| Ser B | AGGAGAACAacagtaactggcgacGGGATGAGG | 14 |
| 1896 | CATCATATAggctagctacaacgaCCCTAACAC | 15 |
| 1903 | ACTCCCCCAggetagetacaacgaCATATACCC | 16 |
| 1911 | AAAGATCTAggctagctacaacgaTCCCCCATC | 17 |
| 1967 | TGGGGTGGAggctagctacaacgaGAGGAAGGT | 18 |
| 1976 | GGGGAGGGAggctagctacaacgaGGGGTGGAT | 19 |
| 1991 | AAAGTGCAAggctagctacaacgaGAACTGGGG | 20 |
| 2002 | CGCTGCTAAggctagctacaacgaCAAAGTGCA | 21 |
| 2021 | AATGTCTGAggctagctacaacgaTCCTTGTTC | 22 |

TABLE 2 p21 hot areas (p21HA) for mRNA silencing

| Hot area | Region | Region size | Score | Sequence (5' -> 3') | SEQ ID NO: |
|---|---|---|---|---|---|
| HA09 | 1947-2022 | 74 | 5 | ATCGTCCAGCGACCTTCCTCATCCACCCCATCCCTCCC CAGTTCATTGCACTTTGATTAGCAGCGGAACAAGGA | 3 |
| HA07 | 1455-1473 | 19 | 5 | ATACCCCCCTCTGTCTTGT | 4 |
| HA06 | 1089-1346 | 258 | 5 | ATACTATTTAAAGCCTCCTCATCCCGTGTTCTCCTTTTCCTCTCTCCCGGAGGTT GGGTGGGCCGGCTTCATGCCAGCTACTTCCTCCTCCCCACTTGTCCGCTGGGTG GTACCCTCTGGAGGGGTGTGGCTCCTTCCCATCGCTGTCACAGGCGGTTATGAA ATTCACCCCCTTTCCTGGACACTCAGACCTGAATTCTTTTTCATTTGAGAAGTAA ACAGATGGCACTTTGAAGGGGCCTCACCGAGTGGGGGCAT | 5 |
| HA08 | 1524-1890 | 367 | 5 | ATGGCCCCTCTGACCTGCACTGGGGAGCCCGTCTCAGTGTTGAGCCTTTTCCCTC TTTGGCTCCCCTGTACCTTTTGAGGAGCCCCAGCTACCCTTTTTCTCCAGCTGGG CTCTGCAATTCCCCTCTGCTGCTGTCCCTCCCCCTTGTCCTTTCCCTTCAGTACCC TCTCAGCTCCAGGTGGCTCTGAGGTGCCTGTCCCACCCCCACCCCCAGCTCAATG GACTGGAAGGGGAAGGGACACACAAGAAGAAGGGCACCCTAGTTCTACCTCAG GCAGCTCAAGCAGCGACCGCCCCCTCCTCTAGCTGTGGGGGTGAGGGTCCCATG TGGTGGCACAGGCCCCCTTGAGTGGGGTTATCTCTGTGT | 6 |
| HA01 | 168-240 | 73 | 4 | ATAGTCATTTCTTTGCTGCATGATCTGAGTTAGGTCACCAGACTTCTCTGAGCCC CAGTTTCCCCAGCAGTGT | 7 |
| HA05 | 944-1065 | 122 | 4 | ATTTGTGTTTTAATTTAAACACCTCCTCATGTACATACCCTGGCCGCCCCTG CCCCCCAGCCTCTGGCATTAGAATTATTTAAACAAAAACTAGGCGGTTGAAT GAGAGGTTCCTAAGAGT | 8 |
| HA03 | 475-683 | 209 | 4 | ATCCAGGAGGCCCGTGAGCGATGGAACTTCGACTTTGTCACCGAGACACCAC TGGAGGGTGACTTCGCCTGGGAGCGTGTGCGGGGCCTTGGCCTGCCCAAGCT CTACCTTCCCACGGGGCCCCGGCGAGGCCGGGATGAGTTGGGAGGAGGCAGG CGGCCTGGCACCTCACCTGCTCTGCTGCAGGGGACAGCAGAGGAAGACCATGT | 9 |
| HA04 | 797-933 | 137 | 3 | ATTTCTACCACTCCAAACGCCGGCTGATCTTCTCCAAGAGGAAGCCCTAAT CCGCCCACAGGAAGCCTGCAGTCCTGGAAGCGCGAGGGCCTCAAAGGCCC GCTCTACATCTTCTGCCTTAGTCTCAGTTTGTGTGT | 10 |
| HA02 | 290-372 | 83 | 3 | ATCCTCCCCTTCCTGGCCAACAAAGCTGCTGCAACCACAGGGATTTCTTCT GTTCAGGCGCCATGTCAGAACCGGCTGGGGAT | 11 |
| HA10 | 2233-2250 | 18 | 2 | GCACTGAAGTGCTTAGTG | 12 |

TABLE 3A-continued

DNAzyme sequences targeting areas at or surrounding HA09

| DNAzyme name | Sequence | SEQ ID NO |
|---|---|---|
| 2028 | ATCTTAAAAggctagctacaacgaGTCTGACTC | 23 |
| 2039 | CTACTGCCAggctagctacaacgaCATCTTAAA | 24 |
| 2045 | TAGCCTCTAggctagctacaacgaTGCCACCAT | 25 |

Of note, high case letters pertain to the two recognition arms of DNAzyme that bind the mRNA sequence and the low case letters pertain to the catalytic core which cleaves the target mRNA. Of note, DNAzymes 1967, 1976, 1991, 2002, 2021 target within "HA09".

TABLE 3B

DNAzyme sequences for different p21 hot areas

| Hot area | DNAzyme Name | sequence | SEQ ID NO: |
|---|---|---|---|
| HA01 | 168 | AAATGACTAggctagctacaacgaAGTTGGAAC | 26 |
| | 171 | AAGAAATGAggctagctacaacgaTATAGTTGG | 27 |
| | 187 | CTCAGATCAggctagctacaacgaGCAGCAAAG | 28 |
| | 190 | TAACTCAGAggctagctacaacgaCATGCAGCA | 29 |
| | 196 | GTGACCTAAggctagctacaacgaTCAGATCAT | 30 |
| | 201 | GTCTGGTGAggctagctacaacgaCTAACTCAG | 31 |
| | 239 | GCCCGTATAggctagctacaacgaACTGCTGGG | 32 |
| HA02 | 329 | AAGAAATCtccgagccggacgaTGTGGTTGC | 33 |
| | 332 | CAGAAGAAAggctagctacaacgaCCCTGTGGT | 34 |
| | 341 | GCGCCTGAAggctagctacaacgaAGAAGAAAT | 35 |
| | 371 | TGACGGACAggctagctacaacgaCCCCAGCCG | 36 |
| HA03 | 475 | CCTCCTGGAggctagctacaacgaGCAGCCCGC | 37 |
| | 479 | CGGGCctCtccgagccggacgaGGATGCAGC | 38 |
| | 480 | ACGGGccTtccgagccggacgaTGGATGCAG | 39 |
| | 488 | CATCGCTCAggctagctacaacgaGGGCCTCCT | 40 |
| | 511 | TCTCGGTGAggctagctacaacgaAAAGTCGAA | 41 |
| | 530 | AAGTCACCtccgagccggacgaCCAGTGGTG | 42 |
| | 533 | GCGAAGTCAggctagctacaacgaCCTCCAGTG | 43 |
| | 551 | CCCCGCACAggctagctacaacgaGCTCCCAGG | 44 |
| | 553 | GGCCCCGCAggctagctacaacgaACGCTCCCA | 45 |
| | 611 | CCCAACTCAggctagctacaacgaCCCGGCCTC | 46 |
| | 615 | TCCTCCCAAggctagctacaacgaTCATCCCGG | 47 |
| | 666 | TTCctctGtccgagccggacgaGTCCCctGC | 48 |
| | 680 | AGGTCCACAggctagctacaacgaGGGTCTTCCT | 49 |
| | 682 | ACAGGTCCAggctagctacaacgaATGGTCTTC | 50 |

TABLE 3B-continued

DNAzyme sequences for different p21 hot areas

| Hot area | DNAzyme Name | sequence | SEQ ID NO: |
|---|---|---|---|
| HA04 | 797 | TGGTAGAAAggctagctacaacgaCTGTCATGC | 51 |
| | 803 | TTGGAGTGGggctagctacaacgaAGAAATCTG | 52 |
| | 806 | CGTTTGGAGggctagctacaacgaGGTAGAAAT | 53 |
| | 823 | TGGAGAAGAggctagctacaacgaCAGCCGGCG | 54 |
| | 868 | CTTCCAGGAggctagctacaacgaTGCAGGCTT | 55 |
| | 905 | GGCAGAAGAggctagctacaacgaGTAGAGCGG | 56 |
| | 918 | AAACTGAGAggctagctacaacgaTAAGGCAGA | 57 |
| | 924 | ACACACAAAggctagctacaacgaTGAGACTAA | 58 |
| | 928 | TAAGACACAggctagctacaacgaAAACTGAGA | 59 |
| | 930 | ATTAAGACAggctagctacaacgaACAAACTGA | 60 |
| | 932 | TAATTAAGAggctagctacaacgaACACAAACT | 61 |
| HA05 | 944 | AAACACAAAggctagctacaacgaAATAATTAA | 62 |
| | 948 | ATTAAAACAggctagctacaacgaAAATAATAA | 63 |
| | 950 | AAATTAAAAggctagctacaacgaACAAATAAT | 64 |
| | 956 | GTGTTTAAAggctagctacaacgaTAAAACACA | 65 |
| | 972 | GTATGTACAggctagctacaacgaGAGGAGGTG | 66 |
| | 978 | GCCAGGGTAggctagctacaacgaGTACATGAG | 67 |
| | 1019 | TTTAAATAAggctagctacaacgaTCTAATGCC | 68 |
| | 1022 | TTGTTTAAAggctagctacaacgaAATTCTAAT | 69 |
| | 1028 | TAGTTTTTGggctagctacaacgaTTAAATAAT | 70 |
| | 1042 | CTCATTCAAggctagctacaacgaCGCCTAGTT | 71 |
| | 1047 | AACCTCTCAggctagctacaacgaTCAACCGCC | 72 |
| | 1054 | TCTTAGGAAggctagctacaacgaCTCTCATTC | 73 |
| | 1064 | TGCCCAGCAggctagctacaacgaTCTTAGGAA | 74 |
| HA06 | 1094 | GGCTTTAAAggctagctacaacgaAGTATTTCA | 75 |
| | 1109 | AACACGGGAggctagctacaacgaGAGGAGGCT | 76 |
| | 1141 | CCCACCCAAggctagctacaacgaCTCCGGGAG | 77 |
| | 1146 | GCCGGCCCAggctagctacaacgaCCAACCTCC | 78 |
| | 1159 | TAGCTGGCAggctagctacaacgaGAAGCCGGC | 79 |
| | 1186 | CCCAGCGGAggctagctacaacgaAAGTGGGGA | 80 |
| | 1195 | AGGGTACCAggctagctacaacgaCCAGCGGAC | 81 |
| | 1198 | CAGAGGGTAggctagctacaacgaCACCCAGCG | 82 |
| | 1213 | GGAGCCACAggctagctacaacgaCCCTCCAGA | 83 |
| | 1215 | AAGGAGCCAggctagctacaacgaACCCCTCCA | 84 |
| | 1228 | TGACAGCGAggctagctacaacgaGGGAAGGAG | 85 |
| | 1234 | CGCCTGTGAggctagctacaacgaAGCGATGGG | 86 |
| | 1244 | ATTTCATAAggctagctacaacgaCGCCTGTGA | 87 |

TABLE 3B-continued

DNAzyme sequences for different p21 hot areas

| Hot area | DNAzyme Name | sequence | SEQ ID NO: |
|---|---|---|---|
|  | 1247 | TGAATTTCAggctagctacaacgaAACCGCCTG | 88 |
|  | 1284 | GAAAAAGAAggctagctacaacgaTCAGGTCTG | 89 |
|  | 1294 | CTTCTCAAAggctagctacaacgaGAAAAAGAA | 90 |
|  | 1303 | ATCTGTTTAggctagctacaacgaTTCTCAAAT | 91 |
|  | 1311 | AAAGTGCCAggctagctacaacgaCTGTTTACT | 92 |
|  | 1337 | ATGCCCCAggctagctacaacgaTCGGTGAGG | 93 |
|  | 1345 | TTTTGATGAggctagctacaacgaGCCCCCACT | 94 |
| HA07 | 1472 | CTGCCTTCAggctagctacaacgaAAGACAGAG | 95 |
| HA08 | 1554 | ACACTGAGAggctagctacaacgaGGGCTCCCC | 96 |
|  | 1560 | GGCTCAACAggctagctacaacgaTGAGACGGG | 97 |
|  | 1562 | AAGGCTCAAggctagctacaacgaACTGAGACG | 98 |
|  | 1583 | ACAGGGGAggctagctacaacgaCAAAGAGGG | 99 |
|  | 1657 | GGGGAGGGAggctagctacaacgaAGCAGCAGA | 100 |
|  | 1702 | TCAGAGCCAggctagctacaacgaCTGGAGCTG | 101 |
|  | 1712 | GACAGGCAtccgagcggacgaTCAGAGCCA | 102 |
|  | 1713 | GGACAGGCAggctagctacaacgaCTCAGAGCC | 103 |
|  | 1715 | TGGGACAGGggctagctacaacgaACCTCAGAG | 104 |
|  | 1796 | TGAGCTGCtccgagccggacgaGAGGTAGAA | 105 |
|  | 1797 | TTGAGCTGtccgagcggacgaTGAGGTAGA | 106 |
|  | 1798 | CTTGAGCTGggctagctacaacgaCTGAGGTAG | 107 |
|  | 1801 | CTGCTTGAGggctagctacaacgaTGCCTGAGG | 108 |
|  | 1832 | TCACCCCCAggctagctacaacgaAGCTAGAGG | 109 |
|  | 1844 | CACATGGGAggctagctacaacgaCCTCACCCC | 110 |
|  | 1849 | GCCACCACAggctagctacaacgaGGGACCCTC | 111 |
|  | 1878 | CAGAGATAAggctagctacaacgaCCCACTCAA | 112 |
|  | 1881 | ACACAGAGAggctagctacaacgaAACCCCACT | 113 |
|  | 1887 | CCCCTAACAggctagctacaacgaAGAGATAAC | 114 |
|  | 1889 | TACCCCTAAggctagctacaacgaACAGAGATA | 115 |
| HA09 | 1950 | GTCGCTGGAggctagctacaacgaGATTTGAGG | 116 |
|  | 2002 | CGCTGCTAAggctagctacaacgaCAAAGTGCA | 117 |
|  | 2008 | TTGTTCCGtccgagccggacgaGCTAATCAA | 118 |
|  | 2021 | AATGTCTGAggctagctacaacgaTCCTTGTTC | 119 |

TABLE 3B-continued

DNAzyme sequences for different p21 hot areas

| Hot area | DNAzyme Name | sequence | SEQ ID NO: |
|---|---|---|---|
| HA10 | 2233 | CAGGACACAggctagctacaacgaGGGGAGCCG | 120 |
|  | 2237 | GAACCAGGAggctagctacaacgaACATGGGGA | 121 |
|  | 2243 | AAACGGGAAggctagctacaacgaCAGGACACA | 122 |
|  | 2249 | GTGGAGAAAggctagctacaacgaGGGAACCAG | 123 |

Of note, high case letters pertain to the two recognition arms of DNAzyme that bind the mRNA sequence and the low case letters pertain to the catalytic core which cleaves the target mRNA Furthermore, incubation of p21 targeting DNAzymes with senescent cells displayed senolytic activity. Specifically, cleavage of the p21 mRNA by DNAzymes in senescent human lung fibroblasts (IMR-90) lead to reduced viability of these cells (FIG. 6). The most efficient DNAzymes were those designed against the algorithm-deduced "Hot spot Areas", these showed a marked senolytic activity of approximately 30% (FIG. 6). Taken together, these results illustrated that silencing molecules targeting p21 mRNA hot areas, such as DNAzymes, can be developed for therapy for specific downregulation of p21, such as for senolytics.

Example 2

Targeting DNAzymes to p21 Hot Areas

The present inventors further examined RNA silencing using antisense oligonucleotides (ASOs) and siRNA molecule targeting hot areas and those targeting areas outside of the hot areas (i.e. designated "cold areas"). Such molecules were designed based on the cleavage site position on the p21 mRNA as set forth in (see Tables 4 and 5, below).

TABLE 4

Antisense oligonucleotides targeting different p21 hot and cold areas

| Location from 5' | Region | Sequence | SEQ ID NO: |
|---|---|---|---|
| 192 | Hot Area 1 | AGTCTGGTGACCTAACTCAG | 143 |
| 324 | Hot Area 2 | AACAGAAGAAATCCCTGTGG | 144 |
| 575 | Hot Area 3 | CCCCGTGGGAAGGTAGAGCT | 145 |
| 801 | Hot Area 4 | GCCGGCGTTTGGAGTGGTAG | 146 |
| 1023 | Hot Area 5 | CCGCCTAGTTTTTGTTTAAA | 147 |
| 1162 | Hot Area 6 | GGGGAGGAGGAAGTAGCTGG | 148 |
| 1756 | Hot Area 8 | TTCTTCTTGTGTGTCCCTTC | 149 |
| 1999 | Hot Area 9 | CTTGTTCCGCTGCTAATCAA | 150 |
| 4 | Cold Area 1 | TCTTCTATGCCAGAGCTCAA | 151 |
| 243 | Cold Area 2 | ATACTCCCCACATAGCCCGT | 152 |
| 374 | Cold Area 3 | GCCGCATGGGTTCTGACGGA | 153 |
| 703 | Cold Area 4 | CCTGAGCGAGGCACAAGGGT | 154 |

TABLE 4-continued

Antisense oligonucleotides targeting different p21 hot and cold areas

| Location from 5' | Region | Sequence | SEQ ID NO: |
|---|---|---|---|
| 740 | Cold Area 4 | GTCTCCAGGTCCACCTGGGG | 155 |
| 1502 | Cold Area 8 | GGGCAGGCGGGGTGGTCTGC | 156 |
| 1891 | Cold Area 9 | TCCCCCATCATATACCCCTA | 157 |
| 2108 | Cold Area 10 | GGGGCTCAACGTTAGTGCCA | 158 |

TABLE 5 siRNA targeting p21 HA08

| Name | Type | Sequence |
|---|---|---|
| siRNA 1668 strand 1 | SIRNA | UGAGAGGGUACUGA AGGGAAAGGACAA (SEQ ID NO: 141) |
| SiRNA 1668 strand 2 | SIRNA | GUCCUUUCCCUUCA GUACCCUCUCA (SEQ ID NO: 142) |

As illustrated in FIG. 7, targeting p21 HA08 in BJ senescent fibroblasts was significantly more efficient in killing the senescent BJ cells compared to siRNA from a commercial source comprised of a pool of 4 sequences targeting different sites over the p21 mRNA. These results were further confirmed by measuring p21 mRNA levels in senescent BJ cells following transfection with siRNA. As illustrated in FIG. 8, a strong mRNA knock-down was exhibited by siRNA directed against HA08 as compared to the commercial siRNA targeting 4 other sites along p21 mRNA.

Similar results were illustrated for p21 mRNA levels in senescent BJ cells following transfection with ASOs directed against cold areas (CA) as compared to ASOs targeting hot areas (HA). The data illustrated reduced p21 mRNA expression by ASOs directed against hot areas compared to cold areas.

Taken together, these results illustrates that targeting the identified hot areas is beneficial for targeted down regulation using varied RNA silencing molecules.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A DNAzyme molecule comprising the nucleic acid sequence set forth in any one of SEQ ID NOs: 18, 19, 20, 21, or 22 or a DNAzyme molecule comprising the nucleic acid sequence at least 80% identical to the nucleic acid sequence set forth in any one of SEQ ID NOs: 18, 19, 20, 21, or 22.

2. The DNAzyme molecule of claim 1, wherein said DNAzyme molecule comprises no more than 70 nucleotides.

3. The DNAzyme molecule of claim 1, wherein the nucleic acid sequence of said DNAzyme molecule comprises at least one modification.

4. The DNAzyme molecule of claim 3, wherein the modification comprises an insertion, a deletion, a substitution, or a point mutation of at least one nucleic acid.

5. The DNAzyme molecule of claim 3, wherein said modification comprises a modification that increases the stability or prevents degradation of the DNAzyme molecule.

6. The DNAzyme molecule of claim 5, wherein said modification comprises an edge-blocker oligonucleotide.

7. The DNAzyme molecule of claim 5, wherein said modification comprises an inverted deoxythymidine (dT) positioned in at least one terminal end of the DNAzyme molecule.

8. The DNAzyme molecule of claim 5, wherein said modification comprises at least one protective group positioned in at least one terminal end of the DNAzyme molecule.

9. The DNAzyme molecule of 3, wherein said modification comprises a base modification, a sugar modification and/or an internucleotide linkage modification.

10. The DNAzyme molecule of claim 9, wherein said sugar modification is selected from the group consisting of a 2'-O-methyl (2'-O-Me), a 2'-O-methoxyethyl (2'-O-MOE), a 2'-fluoro (2'-F), a locked nucleic acid (LNA), and a 2'-Fluoroarabinooligonucleotides (FANA).

11. The DNAzyme molecule of claim 1, wherein said DNAzyme molecule is attached to a heterologous moiety.

12. DNAzyme molecule of claim 11, wherein the heterologous moiety comprises a cell-targeting moiety or a cell-penetrating moiety.

13. The DNAzyme molecule of claim 12, wherein the cell-targeting moiety is an affinity moiety.

14. The DNAzyme molecule of claim 13, wherein the affinity moiety binds to a senescent cell specific cell surface polypeptide or binds to a cancer cell specific cell surface polypeptide.

15. A pharmaceutical composition comprising the DNAzyme molecule of claim 1, and a pharmaceutically acceptable carrier.

* * * * *

SEQUENCE LISTING

```
Sequence total quantity: 158
SEQ ID NO: 1            moltype = DNA  length = 2378
FEATURE                 Location/Qualifiers
source                  1..2378
                        mol_type = other DNA
                        organism = Homo sapiens
SEQUENCE: 1
atgttgagct ctggcataga agaggctggt ggctattttg tccttgggct gcctgttttc   60
aggtgaggaa ggggatggta ggagacagga gacctctaaa gaccccagaa ataaaggatg  120
acaagcagag agccccgggc aggaggcaaa agtcctgtgt tccaactata gtcatttctt  180
tgctgcatga tctgagttag gtcaccagac ttctctgagc cccagtttcc ccagcagtgt  240
atacgggcta tgtggggagt attcaggaga cagacaactc actcgtcaaa tcctccccctt  300
cctggccaac aaagctgctg caaccacagg gatttcttct gttcaggcgc catgtcagaa  360
ccggctgggg atgtccgtca gaacccatgc ggcagcaagg cctgccgccg cctcttcggc  420
ccagtggaca gcgagcagct gagccgcgac tgtgatgcgc taatggcggg ctgcatccag  480
gaggcccgtg agcgatggaa cttcgacttt gtcaccgaga caccactgga gggtgacttc  540
gcctgggagc gtgtgcgggg ccttggcctg cccaagctct accttcccac ggggcccgg   600
cgaggccggg atgagttggg aggaggcagg cggcctggca cctcacctgc tctgctgcag  660
gggacagcag aggaagacca tgtggacctg tcactgtctt gtacccttgt gcctcgctca  720
ggggagcagg ctgaagggtc cccaggtgga cctggagact ctcagggtcg aaaacgggcgg  780
cagaccagca tgacagattt ctaccactcc aaacgccggc tgatcttctc caagaggaag  840
ccctaatccg cccacaggaa gcctgcagtc ctggaagcgc gagggcctca aagcccgct   900
ctacatcttc tgccttagtc tcagtttgtg tgtcttaatt attatttgtg ttttaattta  960
aacacctcct catgtacata ccctggccgc ccctgcccc ccagcctctg gcattagaat 1020
tatttaaaca aaaactaggc ggttgaatga gaggttccta agagtgctgg gcattttat  1080
tttatgaaat actatttaaa gcctcctcat cccgtgttct ccttttcctc tctcccggag 1140
gttggtggg ccggcttcat gccagctact tcctcctccc cacttgtccg ctgggtggta  1200
ccctctggag gggtgtggct ccttcccatc gctgtcacag gcggttatga aattcacccc 1260
ctttcctgga cactcagacc tgaattcttt ttcatttgag aagtaaacag atggcacttt 1320
gaaggggcct caccgagtgg gggcatcatc aaaaactttg gagtcccctc acctcctcta 1380
aggttgggca gggtgaccct gaagtgagca cagcctaggg ctgagctggg gacctggtac 1440
cctcctggct cttgataccc ccctctgtct tgtgaaggca gggggaaggt ggggtcctgg 1500
agcagaccac cccgcctgcc ctcatggccc ctctgacctg cactggggag cccgtctcag 1560
tgttgagcct ttccctctt tggctcccct gtaccttgtg aggagcccca gctacccttt 1620
```

-continued

```
ttctccagct gggctctgca attcccctct gctgctgtcc ctcccccttg tcctttccct 1680
tcagtaccct ctcagctcca ggtggctctg aggtgcctgt cccaccccca ccccagctc  1740
aatggactgg aaggggaagg gacacacaag aagaagggca ccctagttct acctcaggca 1800
gctcaagcag cgaccgcccc ctcctctagc tgtgggggtg agggtcccat gtggtggcac 1860
aggcccccct gagtggggtt atctctgtgt tagggtata tgatgggga gtagatcttt 1920
ctaggaggga gacactggcc cctcaaatcc tccagcgacc ttcctcatcc acccatccc  1980
tccccagttc attgcacttt gattagcagc ggaacaagga gtcagacatt ttaagatggt 2040
ggcagtagag gctatggaca gggcatgcca cgtgggctca tatggggctg ggagtagttg 2100
tctttcctgg cactaacgtt gagccctgg aggcactgaa gtgcttagtg tacttggagt 2160
attggggtct gaccccaaac accttccagc tcctgtaaca tactggcctg gactgttttc 2220
tctcggctcc ccatgtgtcc tggttccgt ttctccacct agactgtaaa cctctcgagg 2280
gcagggacca caccctgtac tgttctgtgt ctttcacagc tcctcccaca atgctgaata 2340
tacagcaggt gctcaataaa tgattcttag tgacttta                         2378

SEQ ID NO: 2          moltype = AA  length = 198
FEATURE               Location/Qualifiers
source                1..198
                      mol_type = protein
                      organism = Homo sapiens
SEQUENCE: 2
MWGVFRRQTT HSSNPPLPGQ QSCCNHRDFF CSGAMSEPAG DVRQNPCGSK ACRRLFGPVD  60
SEQLSRDCDA LMAGCIQEAR ERWNFDFVTE TPLEGDFAWE RVRGLGLPKL YLPTGPRRGR 120
DELGGGRRPG TSPALLQGTA EEDHVDLSLS CTLVPRSGEQ AEGSPGGPGD SQGRKRRQTS 180
MTDFYHSKRR LIFSKRKP                                              198

SEQ ID NO: 3          moltype = DNA  length = 74
FEATURE               Location/Qualifiers
misc_feature          1..74
                      note = nucleic acid sequence of p21 hot areas (p21HA) for
                      mRNA silencing
source                1..74
                      mol_type = other DNA
                      organism = synthetic construct
SEQUENCE: 3
atcgtccagc gaccttcctc atccacccca tccctcccca gttcattgca ctttgattag  60
cagcggaaca agga                                                    74

SEQ ID NO: 4          moltype = DNA  length = 19
FEATURE               Location/Qualifiers
misc_feature          1..19
                      note = nucleic acid sequence of p21 hot areas (p21HA) for
                      mRNA silencing
source                1..19
                      mol_type = other DNA
                      organism = synthetic construct
SEQUENCE: 4
ataccccct ctgtcttgt                                                19

SEQ ID NO: 5          moltype = DNA  length = 258
FEATURE               Location/Qualifiers
misc_feature          1..258
                      note = nucleic acid sequence of p21 hot areas (p21HA) for
                      mRNA silencing
source                1..258
                      mol_type = other DNA
                      organism = synthetic construct
SEQUENCE: 5
atactattta aagcctcctc atcccgtgtt ctccttttcc tctctcccgg aggttgggtg  60
ggccggcttc atgccagcta cttcctcctc cccacttgtc cgctgggtgg taccctctgg 120
aggggtgtgg ctccttccca tcgctgtcac aggcggttat gaaattcacc ccctttcctg 180
gacactcaga cctgaattct ttttcatttg agaagtaaac agatggcact ttgaagggc 240
ctcaccgagt gggggcat                                              258

SEQ ID NO: 6          moltype = DNA  length = 367
FEATURE               Location/Qualifiers
misc_feature          1..367
                      note = nucleic acid sequence of p21 hot areas (p21HA) for
                      mRNA silencing
source                1..367
                      mol_type = other DNA
                      organism = synthetic construct
SEQUENCE: 6
atggcccctc tgacctgcac tgggagccc gtctcagtgt tgagcctttt ccctctttgg  60
ctcccctgta ccttttgagg agccccagct acccttttc tccagctggg ctctgcaatt 120
cccctctgct gctgtcctc cccttgtc tttcccttca gtaccctctc agctccaggt 180
ggctctgagg tgcctgtccc accccaccc ccagctcaat ggactggaag ggaagggac  240
acacaagaag aagggcaccc tagttctacc tcaggcagct caagcagcga ccgcccctc  300
ctctagctgt gggggtgagg gtcccatgtg tggcacagg ccccccttgag tggggttatc 360
tctgtgt                                                           367
```

```
SEQ ID NO: 7              moltype = DNA   length = 73
FEATURE                   Location/Qualifiers
misc_feature              1..73
                          note = nucleic acid sequence of p21 hot areas (p21HA) for
                            mRNA silencing
source                    1..73
                          mol_type = other DNA
                          organism = synthetic construct
SEQUENCE: 7
atagtcattt ctttgctgca tgatctgagt taggtcacca gacttctctg agccccagtt  60
tccccagcag tgt                                                     73

SEQ ID NO: 8              moltype = DNA   length = 122
FEATURE                   Location/Qualifiers
misc_feature              1..122
                          note = nucleic acid sequence of p21 hot areas (p21HA) for
                            mRNA silencing
source                    1..122
                          mol_type = other DNA
                          organism = synthetic construct
SEQUENCE: 8
atttgtgttt taatttaaac acctcctcat gtacataccc tggccgcccc ctgccccca   60
gcctctggca ttagaattat ttaaacaaaa actaggcggt tgaatgagag gttcctaaga  120
gt                                                                 122

SEQ ID NO: 9              moltype = DNA   length = 209
FEATURE                   Location/Qualifiers
misc_feature              1..209
                          note = nucleic acid sequence of p21 hot areas (p21HA) for
                            mRNA silencing
source                    1..209
                          mol_type = other DNA
                          organism = synthetic construct
SEQUENCE: 9
atccaggagg cccgtgagcg atggaacttc gactttgtca ccgagacacc actggagggt  60
gacttcgcct gggagcgtgt gcggggcctt ggcctgccca agctctacct tcccacgggg  120
ccccggcgag gcgggatga gttggggagga ggcaggcggc ctggcacctc acctgctctg  180
ctgcagggga cagcagagga agaccatgt                                    209

SEQ ID NO: 10             moltype = DNA   length = 137
FEATURE                   Location/Qualifiers
misc_feature              1..137
                          note = nucleic acid sequence of p21 hot areas (p21HA) for
                            mRNA silencing
source                    1..137
                          mol_type = other DNA
                          organism = synthetic construct
SEQUENCE: 10
atttctacca ctccaaacgc cggctgatct tctccaagag gaagccctaa tccgcccaca  60
ggaagcctgc agtcctggaa gcgcgagggc ctcaaaggcc cgctctacat cttctgcctt  120
agtctcagtt tgtgtgt                                                 137

SEQ ID NO: 11             moltype = DNA   length = 83
FEATURE                   Location/Qualifiers
misc_feature              1..83
                          note = nucleic acid sequence of p21 hot areas (p21HA) for
                            mRNA silencing
source                    1..83
                          mol_type = other DNA
                          organism = synthetic construct
SEQUENCE: 11
atcctcccct tcctggccaa caaagctgct gcaaccacag ggatttcttc tgttcaggcg  60
ccatgtcaga accggctggg gat                                          83

SEQ ID NO: 12             moltype = DNA   length = 18
FEATURE                   Location/Qualifiers
misc_feature              1..18
                          note = nucleic acid sequence of p21 hot areas (p21HA) for
                            mRNA silencing
source                    1..18
                          mol_type = other DNA
                          organism = synthetic construct
SEQUENCE: 12
gcactgaagt gcttagtg                                                18

SEQ ID NO: 13             moltype = DNA   length = 33
FEATURE                   Location/Qualifiers
misc_feature              1..33
```

```
                          note      = DNAzyme sequences targeting areas at or surrounding
                                      HA09
               source     1..33
                          mol_type  = other DNA
                          organism  = synthetic construct
SEQUENCE: 13
atcttccttg gctagctaca acgacgcctc tcc                                          33

SEQ ID NO: 14          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 14
aggagaacaa cagtaactgg cgacgggatg agg                                          33

SEQ ID NO: 15          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 15
catcatatag gctagctaca acgaccctaa cac                                          33

SEQ ID NO: 16          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 16
actcccccag gctagctaca acgacatata ccc                                          33

SEQ ID NO: 17          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 17
aaagatctag gctagctaca acgatccccc atc                                          33

SEQ ID NO: 18          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 18
tggggtggag gctagctaca acgagaggaa ggt                                          33

SEQ ID NO: 19          moltype = DNA  length = 33
FEATURE                Location/Qualifiers
misc_feature           1..33
                          note      = DNAzyme sequences targeting areas at or surrounding
                                      HA09
               source     1..33
                          mol_type  = other DNA
                          organism  = synthetic construct
SEQUENCE: 19
ggggagggag gctagctaca acgaggggtg gat                                          33

SEQ ID NO: 20          moltype = DNA  length = 33
FEATURE                Location/Qualifiers
misc_feature           1..33
                          note      = DNAzyme sequences targeting areas at or surrounding
                                      HA09
```

```
source                   1..33
                         mol_type = other DNA
                         organism = synthetic construct
SEQUENCE: 20
aaagtgcaag gctagctaca acgagaactg ggg                                33

SEQ ID NO: 21            moltype = DNA  length = 33
FEATURE                  Location/Qualifiers
misc_feature             1..33
                         note = DNAzyme sequences targeting areas at or surrounding
                          HA09
source                   1..33
                         mol_type = other DNA
                         organism = synthetic construct
SEQUENCE: 21
cgctgctaag gctagctaca acgacaaagt gca                                33

SEQ ID NO: 22            moltype = DNA  length = 33
FEATURE                  Location/Qualifiers
misc_feature             1..33
                         note = DNAzyme sequences targeting areas at or surrounding
                          HA09
source                   1..33
                         mol_type = other DNA
                         organism = synthetic construct
SEQUENCE: 22
aatgtctgag gctagctaca acgatccttg ttc                                33

SEQ ID NO: 23            moltype = DNA  length = 33
FEATURE                  Location/Qualifiers
misc_feature             1..33
                         note = DNAzyme sequences targeting areas at or surrounding
                          HA09
source                   1..33
                         mol_type = other DNA
                         organism = synthetic construct
SEQUENCE: 23
atcttaaaag gctagctaca acgagtctga ctc                                33

SEQ ID NO: 24            moltype = DNA  length = 33
FEATURE                  Location/Qualifiers
misc_feature             1..33
                         note = DNAzyme sequences targeting areas at or surrounding
                          HA09
source                   1..33
                         mol_type = other DNA
                         organism = synthetic construct
SEQUENCE: 24
ctactgccag gctagctaca acgacatctt aaa                                33

SEQ ID NO: 25            moltype = DNA  length = 33
FEATURE                  Location/Qualifiers
misc_feature             1..33
                         note = DNAzyme sequences targeting areas at or surrounding
                          HA09
source                   1..33
                         mol_type = other DNA
                         organism = synthetic construct
SEQUENCE: 25
tagcctctag gctagctaca acgatgccac cat                                33

SEQ ID NO: 26            moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 26
aaatgactag gctagctaca acgaagttgg aac                                33

SEQ ID NO: 27            moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 27
```

```
aagaaatgag gctagctaca acgatatagt tgg                                33

SEQ ID NO: 28           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 28
ctcagatcag gctagctaca acgagcagca aag                                33

SEQ ID NO: 29           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 29
taactcagag gctagctaca acgacatgca gca                                33

SEQ ID NO: 30           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 30
gtgacctaag gctagctaca acgatcagat cat                                33

SEQ ID NO: 31           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 31
gtctggtgag gctagctaca acgactaact cag                                33

SEQ ID NO: 32           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 32
gcccgtatag gctagctaca acgaactgct ggg                                33

SEQ ID NO: 33           moltype = DNA   length = 31
FEATURE                 Location/Qualifiers
misc_feature            1..31
                        note = DNAzyme sequences for different p21 hot areas
source                  1..31
                        mol_type = other DNA
                        organism = synthetic construct
SEQUENCE: 33
aagaaatctc cgagccggac gatgtggttg c                                  31

SEQ ID NO: 34           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 34
cagaagaaag gctagctaca acgaccctgt ggt                                33

SEQ ID NO: 35           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
```

```
SEQUENCE: 35
gcgcctgaag gctagctaca acgaagaaga aat                                    33

SEQ ID NO: 36           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 36
tgacggacag gctagctaca acgaccccag ccg                                    33

SEQ ID NO: 37           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 37
cctcctggag gctagctaca acgagcagcc cgc                                    33

SEQ ID NO: 38           moltype = DNA  length = 31
FEATURE                 Location/Qualifiers
misc_feature            1..31
                        note = DNAzyme sequences for different p21 hot areas
source                  1..31
                        mol_type = other DNA
                        organism = synthetic construct
SEQUENCE: 38
cgggcctctc cgagccggac gaggatgcag c                                      31

SEQ ID NO: 39           moltype = DNA  length = 31
FEATURE                 Location/Qualifiers
misc_feature            1..31
                        note = DNAzyme sequences for different p21 hot areas
source                  1..31
                        mol_type = other DNA
                        organism = synthetic construct
SEQUENCE: 39
acgggccttc cgagccggac gatggatgca g                                      31

SEQ ID NO: 40           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 40
catcgctcag gctagctaca acgagggcct cct                                    33

SEQ ID NO: 41           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 41
tctcggtgag gctagctaca acgaaaagtc gaa                                    33

SEQ ID NO: 42           moltype = DNA  length = 31
FEATURE                 Location/Qualifiers
misc_feature            1..31
                        note = DNAzyme sequences for different p21 hot areas
source                  1..31
                        mol_type = other DNA
                        organism = synthetic construct
SEQUENCE: 42
aagtcacctc cgagccggac gaccagtggt g                                      31

SEQ ID NO: 43           moltype = DNA  length = 33
FEATURE                 Location/Qualifiers
misc_feature            1..33
                        note = DNAzyme sequences for different p21 hot areas
source                  1..33
                        mol_type = other DNA
```

```
                        organism = synthetic construct
SEQUENCE: 43
gcgaagtcag gctagctaca acgacctcca gtg                                    33

SEQ ID NO: 44           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 44
ccccgcacag gctagctaca acgagctccc agg                                    33

SEQ ID NO: 45           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 45
ggccccgcag gctagctaca acgaacgctc cca                                    33

SEQ ID NO: 46           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 46
cccaactcag gctagctaca acgacccggc ctc                                    33

SEQ ID NO: 47           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 47
tcctcccaag gctagctaca acgatcatcc cgg                                    33

SEQ ID NO: 48           moltype = DNA  length = 31
FEATURE                 Location/Qualifiers
misc_feature            1..31
                        note = DNAzyme sequences for different p21 hot areas
source                  1..31
                        mol_type = other DNA
                        organism = synthetic construct
SEQUENCE: 48
ttcctctgtc cgagccggac gagtcccctg c                                      31

SEQ ID NO: 49           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 49
aggtccacag gctagctaca acgaggtctt cct                                    33

SEQ ID NO: 50           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 50
acaggtccag gctagctaca acgaatggtc ttc                                    33

SEQ ID NO: 51           moltype = DNA  length = 33
FEATURE                 Location/Qualifiers
misc_feature            1..33
                        note = DNAzyme sequences for different p21 hot areas
source                  1..33
```

```
                            mol_type = other DNA
                            organism = synthetic construct
SEQUENCE: 51
tggtagaaag gctagctaca acgactgtca tgc                                33

SEQ ID NO: 52               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 52
ttggagtggg gctagctaca acgaagaaat ctg                                33

SEQ ID NO: 53               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 53
cgtttggagg gctagctaca acgaggtaga aat                                33

SEQ ID NO: 54               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 54
tggagaagag gctagctaca acgacagccg gcg                                33

SEQ ID NO: 55               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 55
cttccaggag gctagctaca acgatgcagg ctt                                33

SEQ ID NO: 56               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 56
ggcagaagag gctagctaca acgagtagag cgg                                33

SEQ ID NO: 57               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 57
aaaactgagag gctagctaca acgataaggc aga                               33

SEQ ID NO: 58               moltype = DNA   length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 58
acacacaaag gctagctaca acgatgagac taa                                33

SEQ ID NO: 59               moltype = DNA   length = 33
FEATURE                     Location/Qualifiers
misc_feature                1..33
                            note = DNAzyme sequences for different p21 hot areas
```

```
source                      1..33
                            mol_type = other DNA
                            organism = synthetic construct
SEQUENCE: 59
taagacacag gctagctaca acgaaaactg aga                              33

SEQ ID NO: 60               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 60
attaagacag gctagctaca acgaacaaac tga                              33

SEQ ID NO: 61               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 61
taattaagag gctagctaca acgaacacaa act                              33

SEQ ID NO: 62               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 62
aaacacaaag gctagctaca acgaaataat taa                              33

SEQ ID NO: 63               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 63
attaaaacag gctagctaca acgaaaataa taa                              33

SEQ ID NO: 64               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 64
aaattaaaag gctagctaca acgaacaaat aat                              33

SEQ ID NO: 65               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 65
gtgtttaaag gctagctaca acgataaaac aca                              33

SEQ ID NO: 66               moltype = DNA  length = 33
FEATURE                     Location/Qualifiers
misc_feature                1..33
                            note = DNAzyme sequences for different p21 hot areas
source                      1..33
                            mol_type = other DNA
                            organism = synthetic construct
SEQUENCE: 66
gtatgtacag gctagctaca acgagaggag gtg                              33

SEQ ID NO: 67               moltype = DNA  length = 33
FEATURE                     Location/Qualifiers
misc_feature                1..33
```

```
                           note = DNAzyme sequences for different p21 hot areas
source                     1..33
                           mol_type = other DNA
                           organism = synthetic construct
SEQUENCE: 67
gccagggtag gctagctaca acgagtacat gag                                        33

SEQ ID NO: 68              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 68
tttaaataag gctagctaca acgatctaat gcc                                        33

SEQ ID NO: 69              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 69
ttgtttaaag gctagctaca acgaaattct aat                                        33

SEQ ID NO: 70              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 70
tagtttttgg gctagctaca acgattaaat aat                                        33

SEQ ID NO: 71              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 71
ctcattcaag gctagctaca acgacgccta gtt                                        33

SEQ ID NO: 72              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 72
aacctctcag gctagctaca acgatcaacc gcc                                        33

SEQ ID NO: 73              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 73
tcttaggaag gctagctaca acgactctca ttc                                        33

SEQ ID NO: 74              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 74
tgcccagcag gctagctaca acgatcttag gaa                                        33

SEQ ID NO: 75              moltype = DNA  length = 33
FEATURE                    Location/Qualifiers
```

```
misc_feature            1..33
                        note = DNAzyme sequences for different p21 hot areas
source                  1..33
                        mol_type = other DNA
                        organism = synthetic construct
SEQUENCE: 75
ggctttaaag gctagctaca acgaagtatt tca                                    33

SEQ ID NO: 76           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 76
aaacacgggag gctagctaca acgagaggag gct                                   33

SEQ ID NO: 77           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 77
cccacccaag gctagctaca acgactccgg gag                                    33

SEQ ID NO: 78           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 78
gccggcccag gctagctaca acgaccaacc tcc                                    33

SEQ ID NO: 79           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 79
tagctggcag gctagctaca acgagaagcc ggc                                    33

SEQ ID NO: 80           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 80
cccagcggag gctagctaca acgaaagtgg gga                                    33

SEQ ID NO: 81           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 81
agggtaccag gctagctaca acgaccagcg gac                                    33

SEQ ID NO: 82           moltype = DNA  length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 82
cagagggtag gctagctaca acgacaccca gcg                                    33

SEQ ID NO: 83           moltype = DNA  length = 33
```

```
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 83
ggagccacag gctagctaca acgaccctcc aga                                         33

SEQ ID NO: 84           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 84
aaggagccag gctagctaca acgaacccct cca                                         33

SEQ ID NO: 85           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 85
tgacagcgag gctagctaca acgagggaag gag                                         33

SEQ ID NO: 86           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 86
cgcctgtgag gctagctaca acgaagcgat ggg                                         33

SEQ ID NO: 87           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 87
atttcataag gctagctaca acgacgcctg tga                                         33

SEQ ID NO: 88           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 88
tgaatttcag gctagctaca acgaaaccgc ctg                                         33

SEQ ID NO: 89           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 89
gaaaaagaag gctagctaca acgatcaggt ctg                                         33

SEQ ID NO: 90           moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 90
cttctcaaag gctagctaca acgagaaaaa gaa                                         33
```

-continued

```
SEQ ID NO: 91          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 91
atctgtttag gctagctaca acgattctca aat                                33

SEQ ID NO: 92          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 92
aaagtgccag gctagctaca acgactgttt act                                33

SEQ ID NO: 93          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 93
atgcccccag gctagctaca acgatcggtg agg                                33

SEQ ID NO: 94          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 94
ttttgatgag gctagctaca acgagccccc act                                33

SEQ ID NO: 95          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 95
ctgccttcag gctagctaca acgaaagaca gag                                33

SEQ ID NO: 96          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 96
acactgagag gctagctaca acgagggctc ccc                                33

SEQ ID NO: 97          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 97
ggctcaacag gctagctaca acgatgagac ggg                                33

SEQ ID NO: 98          moltype = DNA   length = 33
FEATURE                Location/Qualifiers
misc_feature           1..33
                       note = DNAzyme sequences for different p21 hot areas
source                 1..33
                       mol_type = other DNA
                       organism = synthetic construct
SEQUENCE: 98
aaggctcaag gctagctaca acgaaactga g acg                              33
```

```
SEQ ID NO: 99              moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 99
acagggagg gctagctaca acgacaaaga ggg                                        33

SEQ ID NO: 100             moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 100
ggggagggag gctagctaca acgaagcagc aga                                       33

SEQ ID NO: 101             moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 101
tcagagccag gctagctaca acgactggag ctg                                       33

SEQ ID NO: 102             moltype = DNA  length = 31
FEATURE                    Location/Qualifiers
misc_feature               1..31
                           note = DNAzyme sequences for different p21 hot areas
source                     1..31
                           mol_type = other DNA
                           organism = synthetic construct
SEQUENCE: 102
gacaggcatc cgagccggac gatcagagcc a                                         31

SEQ ID NO: 103             moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 103
ggacaggcag gctagctaca acgactcaga gcc                                       33

SEQ ID NO: 104             moltype = DNA  length = 33
FEATURE                    Location/Qualifiers
misc_feature               1..33
                           note = DNAzyme sequences for different p21 hot areas
source                     1..33
                           mol_type = other DNA
                           organism = synthetic construct
SEQUENCE: 104
tgggacaggg gctagctaca acgaacctca gag                                       33

SEQ ID NO: 105             moltype = DNA  length = 31
FEATURE                    Location/Qualifiers
misc_feature               1..31
                           note = DNAzyme sequences for different p21 hot areas
source                     1..31
                           mol_type = other DNA
                           organism = synthetic construct
SEQUENCE: 105
tgagctgctc cgagccggac gagaggtaga a                                         31

SEQ ID NO: 106             moltype = DNA  length = 31
FEATURE                    Location/Qualifiers
misc_feature               1..31
                           note = DNAzyme sequences for different p21 hot areas
source                     1..31
                           mol_type = other DNA
                           organism = synthetic construct
SEQUENCE: 106
```
ttgagctgtc cgagccggac gatgaggtag a                                31

SEQ ID NO: 107          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 107
cttgagctgg gctagctaca acgactgagg tag                              33

SEQ ID NO: 108          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 108
ctgcttgagg gctagctaca acgatgcctg agg                              33

SEQ ID NO: 109          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 109
tcacccccag gctagctaca acgaagctag agg                              33

SEQ ID NO: 110          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 110
cacatgggag gctagctaca acgacctcac ccc                              33

SEQ ID NO: 111          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 111
gccaccacag gctagctaca acgagggacc ctc                              33

SEQ ID NO: 112          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 112
cagagataag gctagctaca acgacccact caa                              33

SEQ ID NO: 113          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 113
acacagagag gctagctaca acgaaacccc act                              33

SEQ ID NO: 114          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct

```
SEQUENCE: 114
cccctaacag gctagctaca acgaagagat aac                                33

SEQ ID NO: 115           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 115
tacccctaag gctagctaca acgaacagag ata                                33

SEQ ID NO: 116           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 116
gtcgctggag gctagctaca acgagatttg agg                                33

SEQ ID NO: 117           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 117
cgctgctaag gctagctaca acgacaaagt gca                                33

SEQ ID NO: 118           moltype = DNA  length = 31
FEATURE                  Location/Qualifiers
misc_feature             1..31
                         note = DNAzyme sequences for different p21 hot areas
source                   1..31
                         mol_type = other DNA
                         organism = synthetic construct
SEQUENCE: 118
ttgttccgtc cgagccggac gagctaatca a                                  31

SEQ ID NO: 119           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 119
aatgtctgag gctagctaca acgatccttg ttc                                33

SEQ ID NO: 120           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 120
caggacacag gctagctaca acgaggggag ccg                                33

SEQ ID NO: 121           moltype = DNA  length = 33
FEATURE                  Location/Qualifiers
misc_feature             1..33
                         note = DNAzyme sequences for different p21 hot areas
source                   1..33
                         mol_type = other DNA
                         organism = synthetic construct
SEQUENCE: 121
gaaccaggag gctagctaca acgaacatgg gga                                33

SEQ ID NO: 122           moltype = DNA  length = 33
FEATURE                  Location/Qualifiers
misc_feature             1..33
                         note = DNAzyme sequences for different p21 hot areas
source                   1..33
                         mol_type = other DNA
```

```
                        organism = synthetic construct
SEQUENCE: 122
aaacgggaag gctagctaca acgacaggac aca                                33

SEQ ID NO: 123          moltype = DNA   length = 33
FEATURE                 Location/Qualifiers
misc_feature            1..33
                        note = DNAzyme sequences for different p21 hot areas
source                  1..33
                        mol_type = other DNA
                        organism = synthetic construct
SEQUENCE: 123
gtggagaaag gctagctaca acgagggaac cag                                33

SEQ ID NO: 124          moltype = DNA   length = 80
FEATURE                 Location/Qualifiers
misc_feature            1..80
                        note = HUMAN T7 CDKN1A FORWARD PRIMER
source                  1..80
                        mol_type = other DNA
                        organism = synthetic construct
SEQUENCE: 124
taatacgact cactatagat gttgagctct ggcatagaag aggctggtgg ctattttgtc   60
cttgggctgc ctgttttcag                                               80

SEQ ID NO: 125          moltype = DNA   length = 80
FEATURE                 Location/Qualifiers
misc_feature            1..80
                        note = HUMAN T7 CDKN1A REVERSE PRIMER
source                  1..80
                        mol_type = other DNA
                        organism = synthetic construct
SEQUENCE: 125
taaagtcact aagaatcatt tattgagcac ctgctgtata ttcagcattg tgggaggagc   60
tgtgaaagac acagaacagt                                               80

SEQ ID NO: 126          moltype = DNA   length = 67
FEATURE                 Location/Qualifiers
misc_feature            1..67
                        note = "MOUSE cdkn1a_ REVERSE PRIMER
source                  1..67
                        mol_type = other DNA
                        organism = synthetic construct
SEQUENCE: 126
aatcatcgag aagtatttat tgagcaccag ctttggggtc gggtgtgagg actcgggaca   60
atgcagg                                                             67

SEQ ID NO: 127          moltype = DNA   length = 45
FEATURE                 Location/Qualifiers
misc_feature            1..45
                        note = "MOUSE T7_cdkn1a_FORWARD PRIMER
source                  1..45
                        mol_type = other DNA
                        organism = synthetic construct
SEQUENCE: 127
taatacgact cactatagtg cagcagccga gaggtgtgag ccgcc                   45

SEQ ID NO: 128          moltype = DNA   length = 15
FEATURE                 Location/Qualifiers
misc_feature            1..15
                        note = 10-23 DNAzyme catalytic seq
source                  1..15
                        mol_type = other DNA
                        organism = synthetic construct
SEQUENCE: 128
ggctagctac aacga                                                    15

SEQ ID NO: 129          moltype = DNA   length = 14
FEATURE                 Location/Qualifiers
misc_feature            1..14
                        note = 8-17 DNAzyme catalytic seq
source                  1..14
                        mol_type = other DNA
                        organism = synthetic construct
SEQUENCE: 129
tccgagccgg acga                                                     14

SEQ ID NO: 130          moltype = DNA   length = 12
FEATURE                 Location/Qualifiers
```

```
misc_feature            1..12
                        note = 16.2-11 DNAzyme catalytic core
source                  1..12
                        mol_type = other DNA
                        organism = synthetic construct
SEQUENCE: 130
gttccccagt tg                                                            12

SEQ ID NO: 131          moltype = RNA   length = 19
FEATURE                 Location/Qualifiers
misc_feature            1..19
                        note = 9-86 DNAzyme catalytic core
source                  1..19
                        mol_type = other RNA
                        organism = synthetic construct
SEQUENCE: 131
tcatgcagcg cgtagtgtc                                                     19

SEQ ID NO: 132          moltype = RNA   length = 19
FEATURE                 Location/Qualifiers
misc_feature            1..19
                        note = 12-91 DNAzyme catalytic core
source                  1..19
                        mol_type = other RNA
                        organism = synthetic construct
SEQUENCE: 132
atgatgcagc gcatgtgtc                                                     19

SEQ ID NO: 133          moltype = RNA   length = 13
FEATURE                 Location/Qualifiers
misc_feature            1..13
                        note = 12-91 DNAzyme catalytic core
source                  1..13
                        mol_type = other RNA
                        organism = synthetic construct
SEQUENCE: 133
aagcagttaa gac                                                           13

SEQ ID NO: 134          moltype = DNA   length = 22
FEATURE                 Location/Qualifiers
misc_feature            1..22
                        note = Bipartite I or II catalytic core
source                  1..22
                        mol_type = other DNA
                        organism = synthetic construct
SEQUENCE: 134
aaggaggtag gggttccgct cc                                                 22

SEQ ID NO: 135          moltype = DNA   length = 20
FEATURE                 Location/Qualifiers
misc_feature            1..20
                        note = GAPDH Forward primer
source                  1..20
                        mol_type = other DNA
                        organism = synthetic construct
SEQUENCE: 135
tggtatcgtg gaaggactca                                                    20

SEQ ID NO: 136          moltype = DNA   length = 20
FEATURE                 Location/Qualifiers
misc_feature            1..20
                        note = GAPDH Reverse primer
source                  1..20
                        mol_type = other DNA
                        organism = synthetic construct
SEQUENCE: 136
ccagtagagg cagggatgat                                                    20

SEQ ID NO: 137          moltype = DNA   length = 20
FEATURE                 Location/Qualifiers
misc_feature            1..20
                        note = HPRT Forward primer
source                  1..20
                        mol_type = other DNA
                        organism = synthetic construct
SEQUENCE: 137
ccctggcgtc gtgattagtg                                                    20

SEQ ID NO: 138          moltype = DNA   length = 20
```

```
FEATURE                 Location/Qualifiers
misc_feature            1..20
                        note = HPRT Reverse primer
source                  1..20
                        mol_type = other DNA
                        organism = synthetic construct
SEQUENCE: 138
tcgagcaaga cgttcagtcc                                                   20

SEQ ID NO: 139          moltype = DNA  length = 19
FEATURE                 Location/Qualifiers
misc_feature            1..19
                        note = On-site 1668 Forward primer
source                  1..19
                        mol_type = other DNA
                        organism = synthetic construct
SEQUENCE: 139
gcccgtctca gtgttgagc                                                    19

SEQ ID NO: 140          moltype = DNA  length = 21
FEATURE                 Location/Qualifiers
misc_feature            1..21
                        note = On-site 1668 Reverse primer
source                  1..21
                        mol_type = other DNA
                        organism = synthetic construct
SEQUENCE: 140
ggagctgaga gggtactgaa g                                                 21

SEQ ID NO: 141          moltype = RNA  length = 27
FEATURE                 Location/Qualifiers
misc_feature            1..27
                        note = siRNA 1668 strand 1
source                  1..27
                        mol_type = other RNA
                        organism = synthetic construct
SEQUENCE: 141
tgagagggta ctgaagggaa aggacaa                                           27

SEQ ID NO: 142          moltype = RNA  length = 25
FEATURE                 Location/Qualifiers
misc_feature            1..25
                        note = siRNA 1668 strand 2
source                  1..25
                        mol_type = other RNA
                        organism = synthetic construct
SEQUENCE: 142
gtcctttccc ttcagtaccc tctca                                             25

SEQ ID NO: 143          moltype = DNA  length = 20
FEATURE                 Location/Qualifiers
misc_feature            1..20
                        note = antisense oligonucleotides (ASOs)
source                  1..20
                        mol_type = other DNA
                        organism = synthetic construct
SEQUENCE: 143
agtctggtga cctaactcag                                                   20

SEQ ID NO: 144          moltype = DNA  length = 20
FEATURE                 Location/Qualifiers
misc_feature            1..20
                        note = antisense oligonucleotides (ASOs)
source                  1..20
                        mol_type = other DNA
                        organism = synthetic construct
SEQUENCE: 144
aacagaagaa atccctgtgg                                                   20

SEQ ID NO: 145          moltype = DNA  length = 20
FEATURE                 Location/Qualifiers
misc_feature            1..20
                        note = antisense oligonucleotides (ASOs)
source                  1..20
                        mol_type = other DNA
                        organism = synthetic construct
SEQUENCE: 145
ccccgtggga aggtagagct                                                   20
```

| | | |
|---|---|---|
| SEQ ID NO: 146<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 146<br>gccggcgttt ggagtggtag | | 20 |
| SEQ ID NO: 147<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 147<br>ccgcctagtt tttgtttaaa | | 20 |
| SEQ ID NO: 148<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 148<br>ggggaggagg aagtagctgg | | 20 |
| SEQ ID NO: 149<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 149<br>ttcttcttgt gtgtcccttc | | 20 |
| SEQ ID NO: 150<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 150<br>cttgttccgc tgctaatcaa | | 20 |
| SEQ ID NO: 151<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 151<br>tcttctatgc cagagctcaa | | 20 |
| SEQ ID NO: 152<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 152<br>atactcccca catagcccgt | | 20 |
| SEQ ID NO: 153<br>FEATURE<br>misc_feature<br><br>source | moltype = DNA   length = 20<br>Location/Qualifiers<br>1..20<br>note = antisense oligonucleotides (ASOs)<br>1..20<br>mol_type = other DNA<br>organism = synthetic construct | |
| SEQUENCE: 153<br>gccgcatggg ttctgacgga | | 20 |

```
SEQ ID NO: 154         moltype = DNA  length = 20
FEATURE                Location/Qualifiers
misc_feature           1..20
                       note = antisense oligonucleotides (ASOs)
source                 1..20
                       mol_type = other DNA
                       organism = synthetic construct
SEQUENCE: 154
cctgagcgag gcacaagggt                                                20

SEQ ID NO: 155         moltype = DNA  length = 20
FEATURE                Location/Qualifiers
misc_feature           1..20
                       note = antisense oligonucleotides (ASOs)
source                 1..20
                       mol_type = other DNA
                       organism = synthetic construct
SEQUENCE: 155
gtctccaggt ccacctgggg                                                20

SEQ ID NO: 156         moltype = DNA  length = 20
FEATURE                Location/Qualifiers
misc_feature           1..20
                       note = antisense oligonucleotides (ASOs)
source                 1..20
                       mol_type = other DNA
                       organism = synthetic construct
SEQUENCE: 156
gggcaggcgg ggtggtctgc                                                20

SEQ ID NO: 157         moltype = DNA  length = 20
FEATURE                Location/Qualifiers
misc_feature           1..20
                       note = antisense oligonucleotides (ASOs)
source                 1..20
                       mol_type = other DNA
                       organism = synthetic construct
SEQUENCE: 157
tcccccatca tataccccta                                                20

SEQ ID NO: 158         moltype = DNA  length = 20
FEATURE                Location/Qualifiers
misc_feature           1..20
                       note = antisense oligonucleotides (ASOs)
source                 1..20
                       mol_type = other DNA
                       organism = synthetic construct
SEQUENCE: 158
ggggctcaac gttagtgcca                                                20
```